US008101740B2

(12) United States Patent
Radu et al.

(10) Patent No.: US 8,101,740 B2
(45) Date of Patent: Jan. 24, 2012

(54) POSITRON EMISSION TOMOGRAPHY PROBES FOR IMAGING IMMUNE ACTIVATION AND SELECTED CANCERS

(75) Inventors: Caius G. Radu, Los Angeles, CA (US); Owen N. Witte, Los Angeles, CA (US); Evan David Nair-Gill, Los Angeles, CA (US); Nagichettiar Satyamurthy, Los Angeles, CA (US); Chengyi J. Shu, Los Angeles, CA (US); Johannes Czernin, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 546 days.

(21) Appl. No.: 12/234,478

(22) Filed: Sep. 19, 2008

(65) Prior Publication Data

US 2009/0105184 A1 Apr. 23, 2009

Related U.S. Application Data

(60) Provisional application No. 60/960,183, filed on Sep. 19, 2007, provisional application No. 61/064,963, filed on Apr. 4, 2008.

(51) Int. Cl.
*C07H 21/04* (2006.01)
(52) U.S. Cl. ............. 536/24.3; 514/43; 514/45; 514/49; 536/26.8; 536/27.1; 536/27.13
(58) Field of Classification Search .................. None
See application file for complete search history.

(56) References Cited

U.S. PATENT DOCUMENTS

| 5,811,073 | A | 9/1998 | Kassis et al. |
| 6,677,314 | B2 | 1/2004 | Klecker et al. |
| 2008/0056988 | A1 | 3/2008 | Conti et al. |

FOREIGN PATENT DOCUMENTS

WO 2008/100848 8/2008

OTHER PUBLICATIONS

Afar, D. et al., "Regulation of the oncogenic activity of BCR-ABL by a tightly bound substrate protein RIN1," Immunity, vol. 6, Jun. 1997, pp. 773-782.
Ahmed, M. et al., "BCR-ABL and constitutively active erythropoietin receptor (cEpoR) activate distinct mechanisms for growth factor-independence and inhibition of apoptosis in Ba/F3 cell line," Oncogene 16, 1998, pp. 489-496.
Alauddin, M. et al., "Biodistribution and pet imaging of [18F]-fluoroadenosine derivatives," Nucl Med Biol, 34(3), Apr. 2007, pp. 267-272.
Alauddin, M. et al., "A general synthesis of 2'-deoxy-2'[18F]fluoro-1-B-D-arabinofuranosyluracil and its 5-substituted nucleosides," J Label Compd Radiopharm 46, 2003, pp. 285-289.
Alauddin, M. et al., "Synthesis of [18F]-labeled adenosine analogues as potential PET imaging agents," J Label Compd Radiopharm 46, 2003, pp. 805-814.
Alauddin, M et al., "Synthesis of [18F]-labeled 2'-deoxy-2'-fluoro-5-methyl-1-B-D-arabinofuranosyluracil ([18F]-FMAU)," J Label Compd Radiopharm 45, 2002, pp. 583-590.
Baldwin, S. et al., "The equilibrative nucleoside transporter family, SLC29," Pflugers Arch—Eur J Physiol 447, 2004, pp. 735-743.
Becker, S. et al., "Kinetics of inflammation and sarcoma cell development in primary moloney sarcoma-virus-induced tumors," Int J Cancer 27, 1981, pp. 229-234.
Blasberg, R. et al., "Herpes simplex virus thymidine kinase as a marker/reporter gene for PET imaging of gene therapy," Q J Nucl Med 43, 1999, pp. 163-169.
Cheng, Z. et al., "A new strategy to screen molecular imaging probe uptake in cell culture without radiolabeling using matrix-assisted laser desorption/ionization time-of-flight mass spectrometry," The Journal of Nuclear Medicine, vol. 46, No. 5, May 2005, pp. 878-886.
Chow, P. et al., "A method of image registration for small animal, multi-modality imaging," Phys Med Biol 51, 2006, pp. 379-390.
Czernin, J. et al., "Positron emission tomography scanning: current and future applications," Annu Rev Med 53, 2002, pp. 89-112.
Dubey, P. et al., "Quantitative imaging of the T cell antitumor response by positron-emission tomography," PNAS, vol. 100, No. 3, Feb. 4, 2003, pp. 1232-1237.
Eriksson, S. et al., "Structure and function of cellular deoxyribonucleoside kinases," CMLS 59, 2002, pp. 1327-1346.
Fefer, A. et al., "Immunologic, virologic, and pathologic studies of regression of autochthonous moloney sarcoma virus-induced tumors in mice," Cancer Research 28, Aug. 1968, pp. 1577-1585.
Fox, C. et al., "Fuel feeds function: energy metabolism and the t-cell response," Nat Rev Immunol 5, Nov. 2005, pp. 844-852.
Frauwirth, K. et al., "Regulation of T lymphocyte metabolism," J Immunol 172, 2004, pp. 4661-4665.
Fyrberg, A. et al., "Cell cycle effect on the activity of deoxynucleoside analogue metabolising enzymes," Biochemical and Biophysical Research Communications 357, 2007, pp. 847-853.
Gambhir, S. et al., "A mutant herpes simplex virus type 1 thymidine kinase reporter gene shows improved sensitivity for imaging reporter gene expression with positron emission tomography," PNAS, vol. 97, No. 6, Mar. 14, 2000, pp. 2785-2790.
Gambhir, S. et al., "A tabulated summary of the FDG PET literature," J Nucl Med 42, 2001, pp. 1S-93S.
Garcia-Manteiga, J. et al., "Nucleoside transporter profiles in human pancreatic cancer cells: role of hCNT1 in 2',2'-difluorodeoxycytidine-induced cytotoxicity," Clinical Cancer Research, vol. 9, Oct. 15, 2003, pp. 5000-5008.
Gattinoni, L. et al., "Adoptive immunotherapy for cancer: building on success," Nature Reviews, vol. 6, May 2006, pp. 383-393.
Giovannetti, E. et al, "Cytotoxic activity of gemcitabine and correlation with expression profile of drug-related genes in human lymphoid cells," Pharmacological Research 55, 2007, pp. 343-349.
Gray, J. et al., "The concentrative nucleoside transporter family, SLC28," Pflugers Arch—Eur J Physiol 447, 2004, pp. 728-734.
Griffith, D. et al., "Nucleoside and nucleobase transport systems of mammalian cells," Biochimica et Biophysica Acta 1286, 1996, pp. 153-181.

(Continued)

*Primary Examiner* — Patrick Lewis
(74) *Attorney, Agent, or Firm* — Gates & Cooper LLP

(57) ABSTRACT

Compounds for use as PET probes and methods for synthesizing and using these, comprising [$^{18}$F]D-FAC and other cytosine and adenosine analogs.

41 Claims, 67 Drawing Sheets

OTHER PUBLICATIONS

Hamacher, K. et al., "Efficient stereospecific synthesis of no-carrier-added 2-[18F]-fluoro-2-deoxy-D-glucose using aminopolyether supported nucleophilic substitution," J Nucl Med 27, Feb. 1986, pp. 235-238.

Jordheim, L. et al., "Characterization of a gemcitabine-resistant murine leukemic cell line: reversion of in vitro resistance by a mononucleotide prodrug," Clinical Cancer Research, vol. 10, Aug. 15, 2004, pp. 5614-5621.

Jordheim, L. et al., "Review of recent studies on resistance to cytotoxic deoxynucleoside analogues," Biochimica et Biophysica Acta 1776, 2007, pp. 138-159.

Kanehisa, M. et al., "KEGG: Kyoto encyclopedia of genes and genomes," Nucleic Acids Research, vol. 28, No. 1, 2000, pp. 27-30.

Kelley, V. et al., "Interaction of mutant lpr gene with background strain influences renal disease," Clinical Immunology and Immunopathology 37, 1985, pp. 220-229.

Koehne, G. et al., "Serial in vivo imaging of the targeted migration of human HSV-TK-transduced antigen-specific lymphocytes," Nature Biotechnology, vol. 21, Apr. 2003, pp. 405-413.

Kroep, J. et al., "Pretreatment deoxycytidine kinase levels predict in vivo gemcitabine sensitivity," Molecular Cancer Therapeutics, vol. 1, Apr. 2002, pp. 371-376.

Le, L. et al., "Mice lacking the orphan G protein-coupled receptor G2A develop a late-onset autoimmune syndrome," Immunity, vol. 14, May 2001, pp. 561-571.

Li, C. et al., "Model-based analysis of oligonucleotide arrays: expression index computation and outlier detection," PNAS, vol. 98, No. 1, Jan. 2, 2001, pp. 31-36.

Liu, G. et al., "NetAffx: Affymetrix probesets and annotations," Nucleic Acids Research, vol. 31, No. 1, 2003, pp. 82-86.

Loening, A. et al., "AMIDE: A free software tool for multimodality medical image analysis," Molecular Imaging, vol. 2, No. 3, Jul. 2003, pp. 131-137.

Mangner, T. et al., "Synthesis of 2'-deoxy-2'-[18F]fluoro-B-D-arabinofuranosyl nucleosides, [18F]FAU, [18F]FMAU, [18F]FBAU and [18F]FIAU, as potential PET agents for imaging cellular proliferation," Nuclear Medicine and Biology 30, 2003, pp. 215-224.

Massoud, T. et al., "Molecular imaging in living subjects: seeing fundamental biological processes in a new light," Genes & Development 17, 2003, pp. 545-580.

McKay, L. et al., "Molecular control of immune/inflammatory responses: interactions between nuclear factor-kB and steroid receptor-signaling pathways," Endocrine Reviews 20(4), 1999, pp. 435-459.

Morse, H. et al., "Abnormalities induced by the mutant gene lpr: expansion of a unique lymphocyte subset," The Journal of Immunology, vol. 129, No. 6, Dec. 1982, pp. 2612-2615.

Nakano, Y. et al., "Gemcitabine chemoresistance and molecular markers associated with gemcitabine transport and metabolism in human pancreatic cancer cells," British Journal of Cancer 96, 2007, pp. 457-463.

Ogawa, M. et al., "18F-FDG accumulation in atherosclerotic plaques: immunohistochemical and PET imaging study," J Nucl Med 25, 2004, pp. 1245-1250.

Orr, R. et al., "2'-deoxycytidine kinase deficiency is a major determinant of 2-chloro-2'-deoxyadenosine resistance in lymphoid cell lines1," Clinical Cancer Research, vol. 1, Apr. 1995, pp. 391-398.

Overwijk, W. et al., "Tumor regression and autoimmunity after reversal of a functionally tolerant state of self-reactive CD8+ T cells," The Journal of Experimental Medicine, vol. 198, No. 4, Aug. 18, 2003, pp. 569-580.

Pankiewicz, K. et al., "Fluorinated nucleosides," Carbohydrate Research 327, 2000, pp. 87-105.

Pankiewicz, K. et al., "A synthesis of 9-(2-deoxy-2-fluro-B-D-arabinofuranosyl)adenine and hypoxanathine," J Org Chem 57, 1992, pp. 553-559.

Phelps, M., "Positron emission tomography provides molecular imaging of biological processes," PNAS, vol. 97, No. 16, Aug. 1, 2000, pp. 9226-9233.

Qi, J. et al., "High-resolution 3D Bayesian image reconstruction using the microPET small-animal scanner," Phys Med Biol 43, 1998, pp. 1001-1013.

Radu, C. et al., "Molecular imaging of lymphoid organs and immune activation by positron emission tomography with a new [18F]-labeled 2'-deoxycytidine analog," Nature Medicine, vol. 14, No. 7, Jul. 2008, pp. 783-788.

Radu, C. et al., "Positron emission tomography with computed tomography imaging of neuroinflammation in experimental autoimmune encephalomyelitis," PNAS, vol. 104, No. 6, Feb. 6, 2007, pp. 1937-1942.

Schepers, K. et al., "Differential kinetics of antigen-specific CD4+ and CD8+ T cell responses in the regression of retrovirus-induced sarcomas," J Immunol 169, 2002, pp. 3191-3199.

Sebastiani, V. et al., "Immunohistochemical and genetic evaluation of deoxycytidine kinase in pancreatic cancer: relationship to molecular mechanisms of gemcitabine resistance and survival," Clin Cancer Res 12(8), Apr. 15, 2006, pp. 2492-2497.

Shi, J. et al., "Association between single nucleotide polymorphisms in deoxycytidine kinase and treatment response among acute myeloid leukaemia patients," Pharmacogenetics 14, 2004, pp. 759-768.

Shields, A. et al., "Imaging proliferation in vivo with [F-18]FLT and positron emission tomography," Nature Medicine, vol. 4, No. 11, Nov. 1998, pp. 1334-1336.

Shipley, L. et al., "Metabolism and disposition of gemcitabine, an oncolytic deoxycytidine analog, in mice, rats, and dogs," Drug Metabolism and Disposition, vol. 20, No. 6, 1992, pp. 849-855.

Shu, C. et al., "Visualization of a primary anti-tumor immune response by positron emission tomography," PNAS, vol. 102, No. 48, Nov. 29, 2005, pp. 17412-17417.

Smal, C. et al., "Identification of in vivo phosphorylation sites on human deoxycytidine kinase," The Journal of Biological Chemistry, vol. 281, No. 8, Feb. 24, 2006, pp. 4887-4893.

Smal, C. et al., "Positive regulation of deoxycytidine kinase activity by phosphorylation of Ser-74 in B-cell chronic lymphocytic leukaemia lymphoocytes," Cancer Letters 253, 2007, pp. 68-73.

Su, H. et al., "Monitoring the antitumor response of naïve and memory CD8 T cells in RAG1 −/− mice by positron-emission tomography," The Journal of Immunology 176, 2006, pp. 4459-4467.

Sun, H. et al., "Imaging DNA synthesis in vivo with 18F-FMAU and PET," The Journal of Nuclear Medicine, vol. 46, No. 2, Feb. 2005, pp. 292-296.

Sun, H. et al., "Imaging DNA synthesis with [18F] FMAU and positron emission tomography in patients with cancer," Molecular Imaging vol. 32, No. 1, Jan. 2005, pp. 15-22.

Tann, C. et al., "Fluorocarbohydrates in synthesis," J Org Chem 50, 1985, pp. 3644-3647.

Tatsumi, M. et al., "Fluorodeoxyglucose uptake in the aortic wall at PET/CT: possible finding for active atherosclerosis," Radiology 229, 2003, pp. 831-837.

Ueno, H. et al., "Pharmacogenomics of gemcitabine: can genetic studies lead to tailor-made therapy?," British Journal of Cancer 97, 2007, pp. 145-151.

Van Der Wilt, C. et al., "The role of deoxycytidine kinase in gemcitabine cytotoxicity," Advances in Experimental Medicine and Biology 486, 2000, pp. 287-290.

Van Rompay, A. et al., "Substrate specificity and phosphorylation of antiviral and anticancer nucleoside analogues by human deoxyribonucleoside kinases and ribonucleoside kinases," Pharmacology & Therapeutics 100, 2003, pp. 119-139.

Verhoef, V. et al., "Identification of the mechanism of activation of 9-B-D-arabinofuranosyladenine in human lymphoid cells using mutants deficient in nucleoside kinases," Cancer Research 41, Nov. 1982, pp. 4478-4483.

Visser, G. et al., "A simplified synthesis of 18F-labelled cytosine- and uracil-nucleosides," Appl Radiat Isot, vol. 37, No. 10, 1986, pp. 1074-1076.

Visser, G. et al., "Synthesis and tumour-localizing properties of [18F]-5-fluorocytosine-arabinoside and [18F]-5-fluorocyclocytidine," Eur J Nucl Med 12, 1986, pp. 137-140.

COMPOUND #1

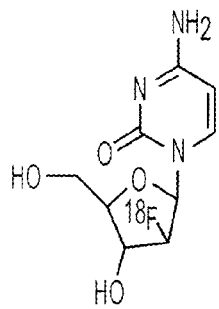

2'-Deoxy-2'-[$^{18}$F]fluoro-beta-D-arabinofuranosylcytosine
(D-$^{18}$F-FAC)

COMPOUND #2

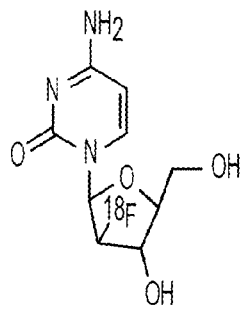

2'-Deoxy-2'-[$^{18}$F]fluoro-beta-L-arabinofuranosylcytosine
(L-$^{18}$F-FAC)

COMPOUND #3

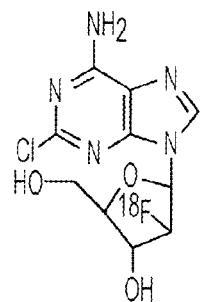

2-Chloro-9-(2-deoxy-2-[$^{18}$F]fluoro-beta-D-arabinofuranosyl)adenine
(2-$^{18}$F-CA)

COMPOUND #4

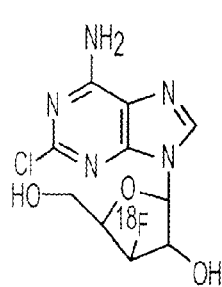

2-Chloro-9-(3-deoxy-3-[$^{18}$F]fluoro-beta-D-arabinofuranosyl)adenine
(3-$^{18}$F-CA)

COMPOUND #5

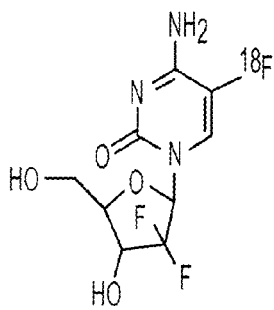

5-[$^{18}$F]Fluoro-2',2'-difluorodeoxycytidine

COMPOUND #6

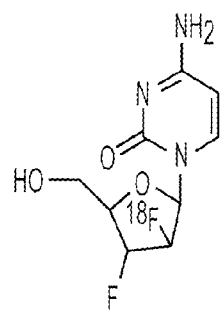

2',3'-Dideoxy-2'-[$^{18}$F]fluoro-3'-fluoro-beta-D-arabinofuranosyl cytosine

COMPOUND #7

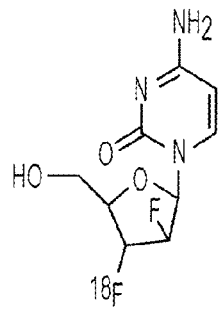

2',3'-Dideoxy-2'-fluoro-3'-[$^{18}$F]fluoro-beta-D-arabinofuranosyl cytosine

FIG. 2A-1

COMPOUND #8

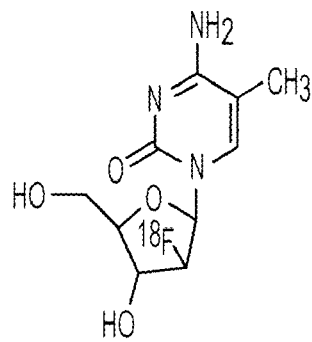

2'-Deoxy-2'-[$^{18}$F]fluoro-5-methyl-beta-D-arabinofuranosylcytosine (D-$^{18}$F-FMAC)

COMPOUND #9

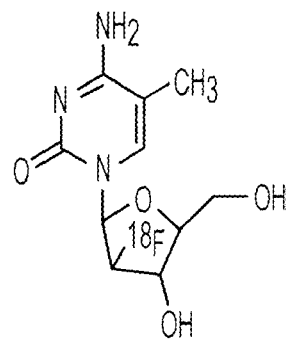

2'-Deoxy-2'-[$^{18}$F]fluoro-5-methyl-beta-L-arabinofuranosylcytosine (L-$^{18}$F-FMAC)

COMPOUND #10

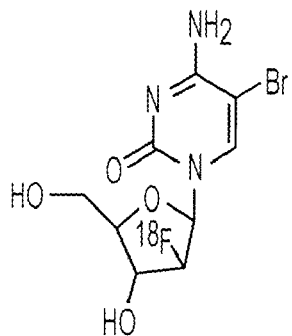

2'-Deoxy-2'-[$^{18}$F]fluoro-5-bromo-beta-D-arabinofuranosylcytosine (D-$^{18}$F-FBAC)

COMPOUND #11

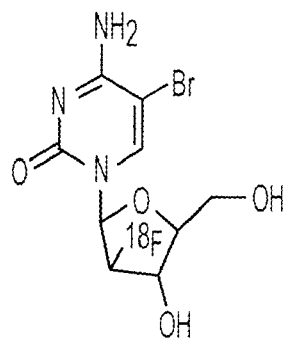

2'-Deoxy-2'-[$^{18}$F]fluoro-5-bromo-beta-L-arabinofuranosylcytosine (L-$^{18}$F-FBAC)

COMPOUND #12

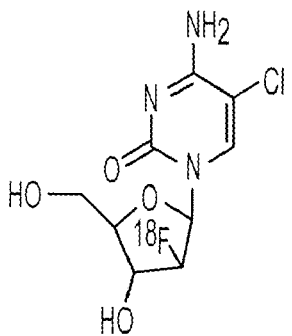

2'-Deoxy-2'-[$^{18}$F]fluoro-5-chloro-beta-D-arabinofuranosylcytosine (D-$^{18}$F-FCAC)

COMPOUND #13

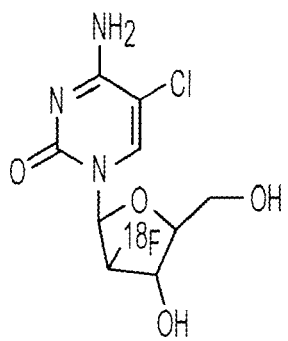

2'-Deoxy-2'-[$^{18}$F]fluoro-5-chloro-beta-L-arabinofuranosylcytosine (L-$^{18}$F-FCAC)

FIG. 2A-2

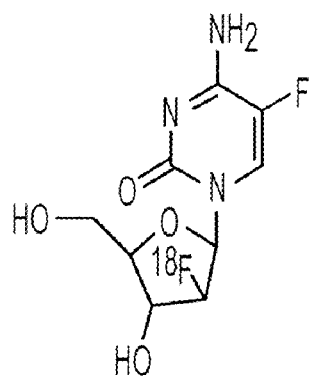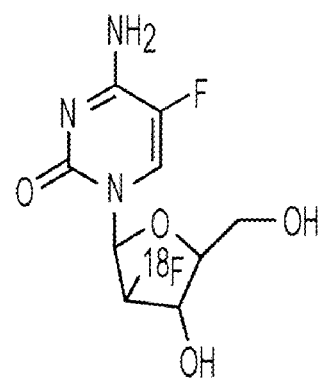
2'-Deoxy-2'-[$^{18}$F]fluoro-5-fluoro-beta-D-arabinofuranosylcytosine (D-$^{18}$F-FFAC)
2'-Deoxy-2'-[$^{18}$F]fluoro-5-fluoro-beta-L-arabinofuranosylcytosine (L-$^{18}$F-FFAC)
FIG. 2A-3

POSITRON EMISSION TOMOGRAPHY PROBES FOR IMAGING IMMUNE ACTIVATION AND SELECTED CANCERS

U.S. provisional patent application Ser. Nos. 60/960,183, filed Sep. 19, 2007, and 61/064,963, filed Apr. 4, 2008, are hereby incorporated by reference, and all benefits thereto are claimed, including the right of priority.

This invention was made with Government support of Grant number DE-FG02-06ER64249 awarded by the U.S. Department of Energy. The government has certain rights in this invention.

BACKGROUND OF THE INVENTION

The advent of molecular imaging approaches such as Positron Emission Tomography (PET) has enabled measurements of molecular and cellular mechanisms throughout the body in preclinical and clinical settings. Such measurements have widespread diagnostic utility and their use for evaluation of treatment responses and to assist drug development is expanding rapidly. Recent studies in mice have documented the feasibility of using PET to visualize immune responses. We and others have demonstrated that anti-tumor T cell immunity can be monitored using PET reporter gene imaging. Similar approaches may enable evaluation of T cell trafficking thus expanding to use in patients undergoing cancer immunotherapy. Nonetheless, development of novel probes that allow for direct measurements of immune function would significantly widen the utility of PET imaging. Various cell surface receptors and intracellular enzymes may potentially be imaged by PET using specialized probes. Recently, in a mouse model of autoimmune demyelination, we showed that a probe for glycolysis called [$^{18}$F]fluorodeoxyglucose ([$^{18}$F]FDG) enables PET-based monitoring of disease onset via distribution of the probe in organs and of immunosuppressive therapy. However, [$^{18}$F]FDG accumulates in non-lymphoid tissues including the heart, brain, and liver. This invention concerns the development of assays and novel probes to monitor biochemical cascades involved in fundamental cellular events such as proliferation, apoptosis, malignant transformation or lymphocyte activation.

SUMMARY

In an embodiment according to the invention, a PET probe includes a compound having a structure according to Formula IA and/or Formula IB,

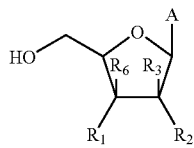

Formula IA

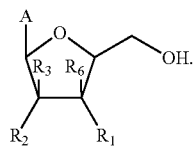

Formula IB $R_1$ can be H, OH, or F, $R_2$ can be H, OH, or F, $R_3$ can be H or F, and $R_6$ can be H or F. A can be selected from the group consisting of

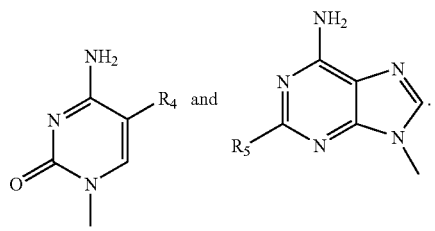

$R_4$ can be H, halogen, or alkyl from 1 to 6 carbons. $R_5$ can be H, halogen, or alkyl from 1 to 6 carbons. One or more of $R_1$, $R_2$, $R_3$, $R_4$, $R_5$, and $R_6$ can be a radioisotope, for example, $^{18}$F, $^{76}$Br and $^{124}$I. For example, A can be

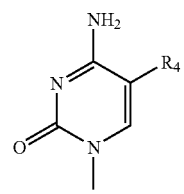

and $R_1$ can be OH or fluorine, $R_2$ can be hydrogen or fluorine, $R_3$ can be fluorine, $R_4$ can be H, F, Cl, Br, I, CH$_3$, or C$_2$H$_5$, and one or more of $R_1$, $R_2$, $R_3$, and $R_4$ can be $^{18}$F. For example, A can be

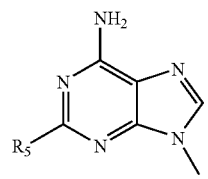

and $R_1$ can be OH or fluorine, $R_2$ can be hydrogen, $R_3$ can be fluorine, $R_5$ can be Cl, F, Br, I, CH$_3$, or C$_2$H$_5$, and at one or more of $R_1$, $R_2$, $R_3$, and $R_5$ can be $^{18}$F. For example, $R_4$ can be H, F, Cl, Br, or CH$_3$, $R_5$ can be Cl, $R_1$, $R_3$, $R_4$, and/or $R_6$ can be the radioisotope $^{18}$F. $R_2$ and $R_5$ can be not radioisotopes other than in a naturally occurring proportion. Some examples of PET probes according to the invention include the following:

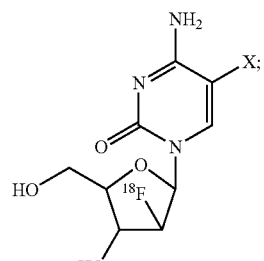

[$^{18}$F]D-FXAC
{D-$^{18}$F-FXAC;
2′-deoxy-2′-[$^{18}$F]fluoro-5-halo-
β-D-arabinofuranosylcytosine}

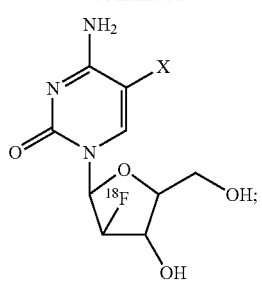

[¹⁸F]L-FXAC,
{L-¹⁸F-FXAC;
2′-deoxy-2′-[¹⁸F]fluoro-5-halo-
β-D-arabinofuranosylcytosine}

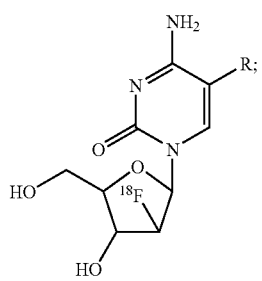

[¹⁸F]D-FRAC
{D-¹⁸F-FRAC;
2′-deoxy-2′-[¹⁸F]fluoro-5-alkyl-
β-D-arabinofuranosylcytosine}

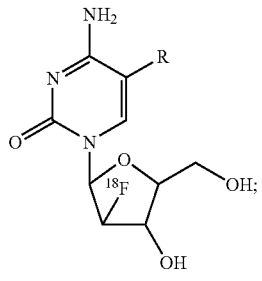

[¹⁸F]L-FRAC
{L-¹⁸F-FRAC;
2′-deoxy-2′-[¹⁸F]fluoro-5-alkyl-
β-L-arabinofuranosylcytosine}

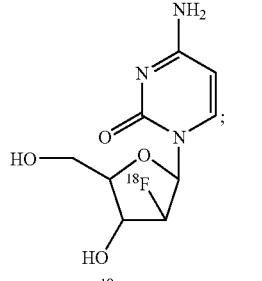

[¹⁸F]D-FAC
{D-¹⁸F-FAC;
2′-deoxy-2′-[¹⁸F]fluoro-
β-D-arabinofuranosylcytosine}

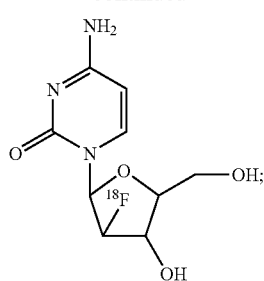

[¹⁸F]L-FAC
{L-¹⁸F-FAC; 2′-deoxy-2′-[¹⁸F]fluoro-
β-L-arabinofuranosylcytosine}

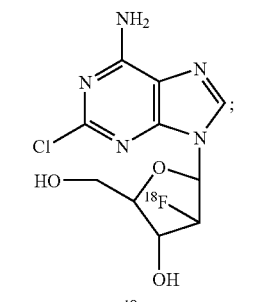

D-2-¹⁸F-CA
{2-chloro-9-(2-deoxy-2-[¹⁸F]fluoro-
β-D-arabinofuranosyl)adenine}

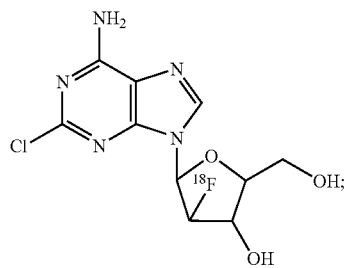

L-2-¹⁸F-CA
{2-chloro-9-(2-deoxy-2-[¹⁸F]fluoro-
β-L-arabinofuranosyl)adenine}

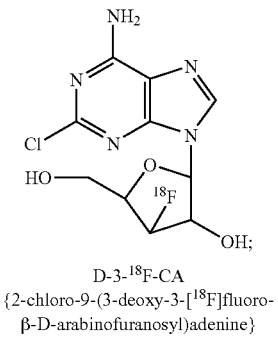

D-3-¹⁸F-CA
{2-chloro-9-(3-deoxy-3-[¹⁸F]fluoro-
β-D-arabinofuranosyl)adenine}

-continued

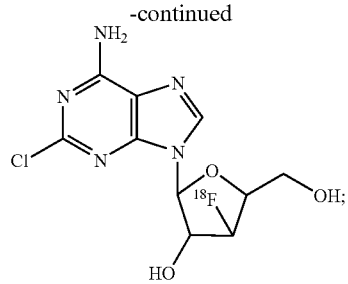

L-3-¹⁸F-CA
{2-chloro-9-(3-deoxy-3-[¹⁸F]fluoro-
β-L-arabinofuranosyl)adenine}

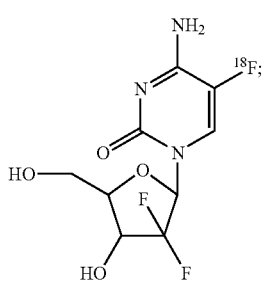

D-Compound #5
{2',2'-deoxy-2',2'-difluoro
β-D-arabinofuranosyl-
5-[¹⁸F]fluorocytosine;
isomer of 5-[¹⁸F]fluoro-
2',2'-difluorodeoxycytidine}

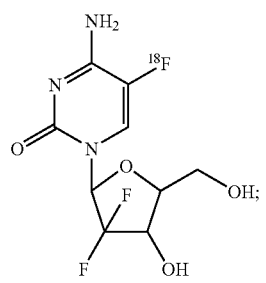

L-Compound #5
{2',2'-deoxy-2',2'-difluoro
β-L-arabinofuranosyl-
5-[¹⁸F]fluorocytosine;
isomer of 5-[¹⁸F]fluoro-
2',2'-difluorodeoxycytidine}

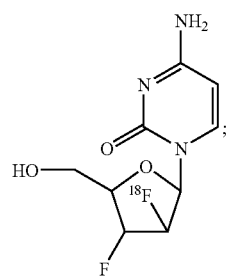

D-Compound #6
{2',3'-dideoxy-2'-[¹⁸F]fluoro-
3'-fluoro-β-D-arabinofuranosylcytosine}

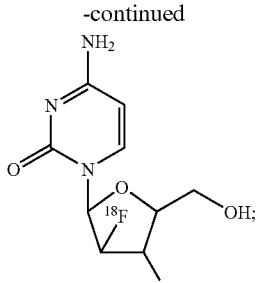

L-Compound #6
{2',3'-dideoxy-2'-[¹⁸F]fluoro-
3'-fluoro-β-L-arabinofuranosylcytosine}

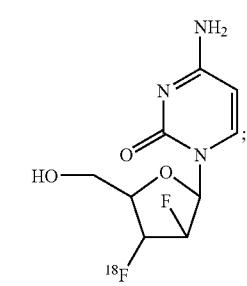

D-Compound #7
{2',3'-dideoxy-2'-fluoro-3'-[¹⁸F]fluoro-
β-D-arabinofuranosylcytosine}

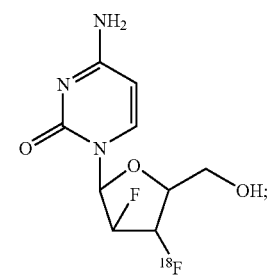

L-Compound #7
{2',3'-dideoxy-2'-fluoro-3'-[¹⁸F]fluoro-
β-L-arabinofuranosylcytosine}

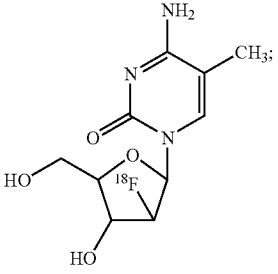

D-¹⁸F-FMAC
{2'-deoxy-2'-[¹⁸F]fluoro-5-methyl-
β-D-arabinofuranosylcytosine}

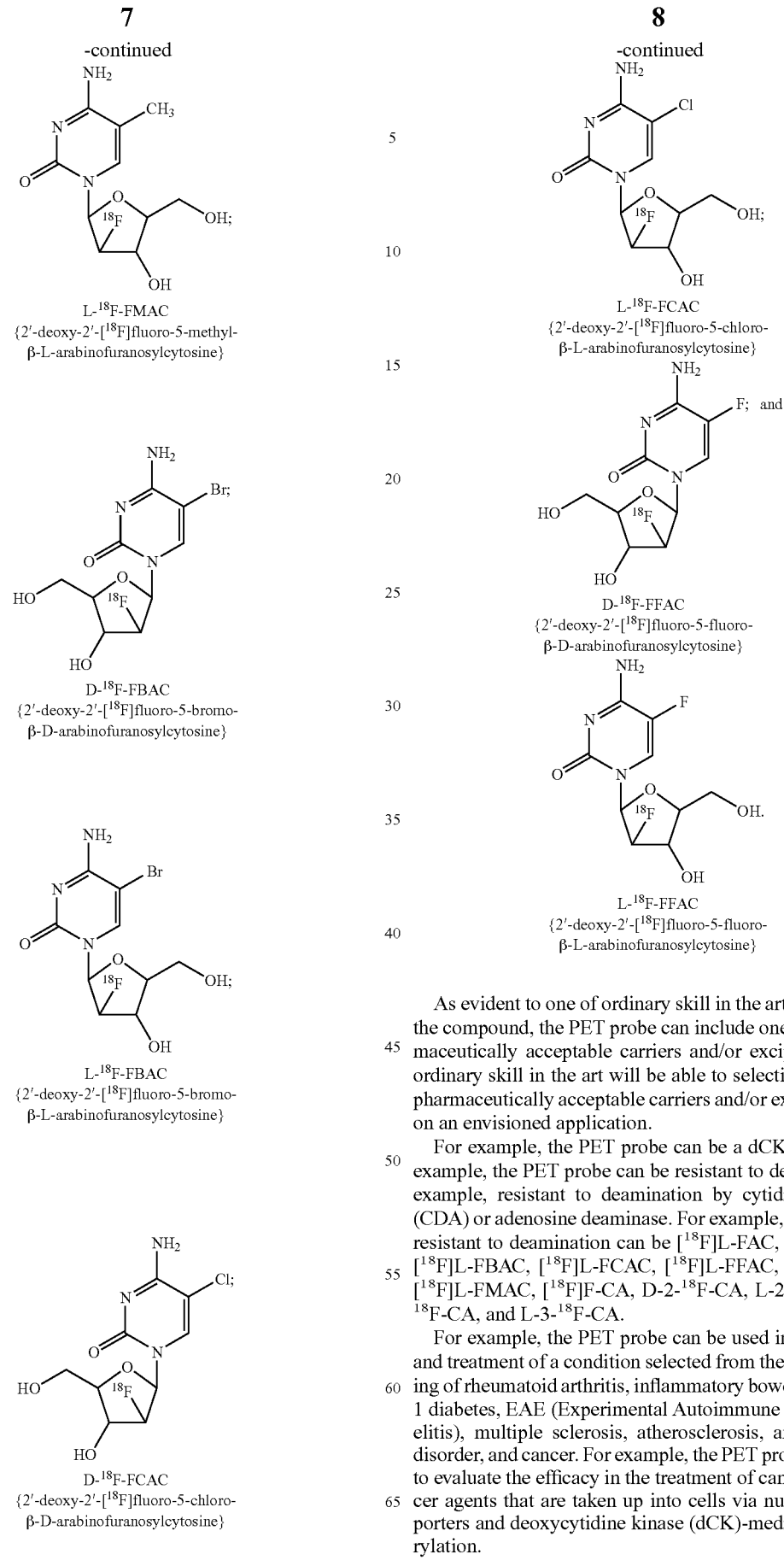

As evident to one of ordinary skill in the art, in addition to the compound, the PET probe can include one or more pharmaceutically acceptable carriers and/or excipients. One of ordinary skill in the art will be able to selection appropriate pharmaceutically acceptable carriers and/or excipients based on an envisioned application.

For example, the PET probe can be a dCK substrate. For example, the PET probe can be resistant to deamination, for example, resistant to deamination by cytidine deaminase (CDA) or adenosine deaminase. For example, the PET probe resistant to deamination can be [$^{18}$F]L-FAC, [$^{18}$F]L-FXAC, [$^{18}$F]L-FBAC, [$^{18}$F]L-FCAC, [$^{18}$F]L-FFAC, [$^{18}$F]L-FRAC, [$^{18}$F]L-FMAC, [$^{18}$F]F-CA, D-2-$^{18}$F-CA, L-2-$^{18}$F-CA, D-3-$^{18}$F-CA, and L-3-$^{18}$F-CA.

For example, the PET probe can be used in the diagnosis and treatment of a condition selected from the group consisting of rheumatoid arthritis, inflammatory bowel disease, type 1 diabetes, EAE (Experimental Autoimmune Encephalomyelitis), multiple sclerosis, atherosclerosis, an autoimmune disorder, and cancer. For example, the PET probe can be used to evaluate the efficacy in the treatment of cancer of anticancer agents that are taken up into cells via nucleoside transporters and deoxycytidine kinase (dCK)-mediated phosphorylation.

A method of synthesizing a PET probe according to the invention can include the following. 2-O-[(trifluoromethyl)sulfonyl]-1,3,5-tri-O-benzoyl-α-D-ribofuranose (an isomer of 5-benzoyloxymethyl-4,2-benzoyloxy-3-trifluoromethyl-sulfonatofuran) can be reacted with [$^{18}$F]fluoride ion. 2-deoxy-2-[$^{18}$F]fluoro-1,3,5-tri-O-benzoyl-α-D-arabinofuranose (an isomer of 5-benzoyloxymethyl-4,2-benzoyloxy-3-$^{18}$-fluorofuran) can be reacted with hydrogen bromide. 2-deoxy-2-[$^{18}$F]fluoro-3,5-di-O-benzoyl-α-D-arabinofuranosyl bromide (an isomer of 5-benzoyloxymethyl-4-benzoyloxy-3-$^{18}$-fluoro-2-bromofuran) can be reacted with 4-N-(trimethylsilyl)-2-O-(trimethylsilyl)pyrimidine-4-amine (i.e., N-(trimethylsilyl)-2-((trimethylsilyl)oxy)pyrimidin-4-amine). And, 1-(2'-deoxy-2'-[$^{18}$F]fluoro-3,5-di-O-benzoyl-β-D-arabinofuranosyl)cytosine (an isomer of 1-(4-benzoyloxymethyl-3-benzoyloxy-2-deoxy-2-$^{18}$fluoroarabinofuranosyl)cytosine) can be reacted with an alkoxide to form the PET probe. The alkoxide can be, for example, an alkali methoxide, e.g., sodium methoxide.

A method of synthesizing a PET probe according to the invention can include the following. 2-O-[(Trifluoromethyl)sulfonyl]-1,3,5-tri-O-benzoyl-α-L-ribofuranose can be reacted with [$^{18}$F]fluoride ion to form 2-deoxy-2-[$^{18}$F]fluoro-1,3,5-tri-O-benzoyl-α-L-arabinofuranose as a first radiolabeled intermediate. The first radiolabeled intermediate can be reacted with hydrogen bromide to form 2-deoxy-2-[$^{18}$F]fluoro-3,5-di-O-benzoyl-α-L-arabinofuranosyl bromide as a second radiolabeled intermediate. The second radiolabeled intermediate can be reacted with 4-N-(trimethylsilyl)-2-O-(trimethylsilyl)pyrimidine-4-amine to form 1-(2'-deoxy-2'-[$^{18}$F]fluoro-3,5-di-O-benzoyl-β-L-arabinofuranosyl)cytosine as a third radiolabeled intermediate. The third radiolabeled intermediate can be reacted with an alkoxide to form the [$^{18}$F]L-FAC PET probe.

A method of synthesizing an [$^{18}$F]-CA PET probe according to the invention can include the following. 2-chloroadenosine can be reacted with monomethoxytrityl chloride to form a first intermediate. The first intermediate can be reacted with trifyl chloride to form a second intermediate. And the second intermediate can be reacted with [$^{18}$F]fluoride ion to form the [$^{18}$F]-CA PET probe. For example, an [$^{18}$F]D-CA PET probe can be synthesized by reacting D-2-chloroadenosine and monomethoxytrityl chloride to form the first intermediate, which can be reacted with [$^{18}$F]fluoride ion to form the [$^{18}$F]D-CA PET probe. For example, an [$^{18}$F]L-CA PET probe can be synthesized by reacting L-2-chloroadenosine and monomethoxytrityl chloride to form the first intermediate, which can be reacted with [$^{18}$F]fluoride ion to form the [$^{18}$F]L-CA PET probe.

A method of synthesizing an [$^{18}$F]D-FXAC PET probe according to the present invention can include the following. 2-O-[(Trifluoromethyl)sulfonyl]-1,3,5-tri-O-benzoyl-α-D-ribofuranose can be reacted with [$^{18}$F]fluoride ion to form 2-deoxy-2-[$^{18}$F]fluoro-1,3,5-tri-O-benzoyl-α-D-arabinofuranose as a first radiolabeled intermediate. The first radiolabeled intermediate can be reacted with hydrogen bromide to form 2-deoxy-2-[$^{18}$F]fluoro-3,5-di-O-benzoyl-α-D-arabinofuranosyl bromide as a second radiolabeled intermediate. The second radiolabeled intermediate can be reacted with 5-halo-4-N-(trimethylsilyl)-2-O-(trimethylsilyl)pyrimidine-4-amine to form 5-halo-1-(2'-deoxy-2'-[$^{18}$F]fluoro-3,5-di-O-benzoyl-β-D-arabinofuranosyl)cytosine as a third radiolabeled intermediate. And the third radiolabeled intermediate can be reacted with an alkoxide to form the [$^{18}$F]D-FXAC PET probe 5-halo-1-(2'-deoxy-2'-[$^{18}$F]fluoro-β-D-arabinofuranosyl)cytosine. For example, halo can be fluoro, chloro, or bromo.

A method of synthesizing an [$^{18}$F]L-FXAC PET probe according to the present invention can include the following. 2-O-[(Trifluoromethyl)sulfonyl]-1,3,5-tri-O-benzoyl-α-L-ribofuranose can be reacted with [$^{18}$F]fluoride ion to form 2-deoxy-2-[$^{18}$F]fluoro-1,3,5-tri-O-benzoyl-α-L-arabinofuranose as a first radiolabeled intermediate. The first radiolabeled intermediate can be reacted with hydrogen bromide to form 2-deoxy-2-[$^{18}$F]fluoro-3,5-di-O-benzoyl-α-L-arabinofuranosyl bromide as a second radiolabeled intermediate. The second radiolabeled intermediate can be reacted with 5-halo-4-N-(trimethylsilyl)-2-O-(trimethylsilyl)pyrimidine-4-amine to form 5-halo-1-(2'-deoxy-2'-[$^{18}$F]fluoro-3,5-di-O-benzoyl-β-L-arabinofuranosyl)cytosine as a third radiolabeled intermediate. And the third radiolabeled intermediate can be reacted with an alkoxide to form the [$^{18}$F]L-FXAC PET probe 5-halo-1-(2'-deoxy-2'-[$^{18}$F]fluoro-β-L-arabinofuranosyl)cytosine. For example, halo can be fluoro, chloro, or bromo.

A method of synthesizing an [$^{18}$F]D-FRAC PET probe according to the present invention can include the following. 2-O-[(Trifluoromethyl)sulfonyl]-1,3,5-tri-O-benzoyl-α-D-ribofuranose can be reacted with [$^{18}$F]fluoride ion to form 2-deoxy-2-[$^{18}$F]fluoro-1,3,5-tri-O-benzoyl-α-D-arabinofuranose as a first radiolabeled intermediate. The first radiolabeled intermediate can be reacted with hydrogen bromide to form 2-deoxy-2-[$^{18}$F]fluoro-3,5-di-O-benzoyl-α-D-arabinofuranosyl bromide as a second radiolabeled intermediate. The second radiolabeled intermediate can be reacted with 5-(lower alkyl)-4-N-(trimethylsilyl)-2-O-(trimethylsilyl)pyrimidine-4-amine to form 5-(lower alkyl)-1-(2'-deoxy-2'-[$^{18}$F]fluoro-3,5-di-O-benzoyl-β-D-arabinofuranosyl)cytosine as a third radiolabeled intermediate. And the third radiolabeled intermediate can be reacted with an alkoxide to form the [$^{18}$F]D-FRAC PET probe 5-(lower alkyl)-1-(2'-deoxy-2'-[$^{18}$F]fluoro-β-D-arabinofuranosyl)cytosine. For example, a lower alkyl can be an alkyl having from 1 to 6 carbons. For example, the lower alkyl can be methyl, so that the synthesized PET probe is [$^{18}$F]D-FMAC.

A method of synthesizing an [$^{18}$F]L-FRAC PET probe according to the present invention can include the following. 2-O-[(Trifluoromethyl)sulfonyl]-1,3,5-tri-O-benzoyl-α-L-ribofuranose can be reacted with [$^{18}$F]fluoride ion to form 2-deoxy-2-[$^{18}$F]fluoro-1,3,5-tri-O-benzoyl-α-L-arabinofuranose as a first radiolabeled intermediate. The first radiolabeled intermediate can be reacted with hydrogen bromide to form 2-deoxy-2-[$^{18}$F]fluoro-3,5-di-O-benzoyl-α-L-arabinofuranosyl bromide as a second radiolabeled intermediate. The second radiolabeled intermediate can be reacted with 5-(lower alkyl)-4-N-(trimethylsilyl)-2-O-(trimethylsilyl)pyrimidine-4-amine to form 5-(lower alkyl)-1-(2'-deoxy-2'-[$^{18}$F]fluoro-3,5-di-O-benzoyl-β-L-arabinofuranosyl)cytosine as a third radiolabeled intermediate. And the third radiolabeled intermediate can be reacted with an alkoxide to form the [$^{18}$F]L-FRAC PET probe 5-(lower alkyl)-1-(2'-deoxy-2'-[$^{18}$F]fluoro-β-L-arabinofuranosyl)cytosine. For example, a lower alkyl can be an alkyl having from 1 to 6 carbons. For example, the lower alkyl can be methyl, so that the synthesized PET probe is [$^{18}$F]L-FMAC.

A method of imaging according to the invention can include the following. A PET probe can be contacted with biological material. PET imaging can be used to determine a local concentration of the PET probe in the biological material. And the local concentration of the PET probe can be correlated with a local immune response. The local immune response can be the accumulation of activated T lymphocytes, and the activated T lymphocytes can take up more PET probe per cell than non-activated T lymphocytes. A quantity of a PET probe, for example, [$^{18}$F]D-FAC, can be administered to an animal or human. For example, the PET probe can be a dCK substrate and/or resistant to deamination by an enzyme, e.g., cytidine deaminase (CDA) or adenosine deaminase.

PET imaging can be used to determine a local concentration of the PET probe in the animal or human, and the local concentration of the PET probe can be correlated with a local immune response or neoplastic tissue. For example, the local concentration of the PET probe can be correlated with abnormal activity in an organ or portion of the lymphatic system, for example, in a lymph node or in the spleen. For example, the local concentration of the PET probe can be correlated with a lymphoma lesion or with a malignant lymphoid disease. The animal or human can have a condition such as cancer, lymphadenopathy, melanoma, leukemia, glioma, an autoimmune disorder, a development disorder, viral infection, bacterial infection, parasitical infection, infection, a metabolic disease, inflammation, rheumatoid arthritis, inflammatory bowel disease, type 1 diabetes, Experimental Autoimmune Encephalomyelitis (EAE), multiple sclerosis, and/or atherosclerosis. The PET probe can be used in the diagnosis and/or treatment of such a condition. The animal or human can be undergoing a therapy such as cancer immunotherapy, immunotherapy, interferon therapy, vaccination, radiation therapy, chemotherapy, and/or antibiotic therapy. For example, the local concentration of the PET probe can be used to diagnose cancer and/or monitor cancer treatment.

A method of imaging according to the invention can include the following. A PET probe that is a dCK substrate resistant to deamination can be contacted with a biological material. For example, the PET probe can be cytosine or adenosine analog. PET imaging can be used to determine a local concentration of the PET probe in the biological material. The local concentration of the PET probe can be correlated with a local immune response or neoplastic tissue.

In a method according to the invention, the PET probe can be used to diagnose, treat, and/or monitor treatment of a condition, such as cancer, rheumatoid arthritis, inflammatory bowel disease, type 1 diabetes, EAE, multiple sclerosis, and atherosclerosis. The PET probe can be used to evaluate the efficacy in the treatment of cancer of an anticancer agent, e.g., cytarabine or 2'-difluorodeoxycytidine, that is taken up into cells via nucleoside transporters and deoxycytidine kinase (dCK)-mediated phosphorylation.

A method of predicting resistance to an oncolytic prodrug according to the invention can include the following. A PET probe, for example, [$^{18}$F]D-FAC, [$^{18}$F]L-FAC, [$^{18}$F]D-FXAC, [$^{18}$F]L-FXAC, [$^{18}$F]D-FFAC, [F]L-FFAC, [$^{18}$F]D-FCAC, [$^{18}$F]L-FCAC, [$^{18}$F]D-FBAC, [$^{18}$F]L-FBAC, [$^{18}$F]D-FRAC, [$^{18}$F]L-FRAC, [$^{18}$F]D-FMAC, [$^{18}$F]L-FMAC, $^{18}$F-CA, D-2-$^{18}$F-CA, L-2-$^{18}$F-CA, D-3-$^{18}$F-CA, or L-3-$^{18}$F-CA, can be contacted with a neoplasm. For example, the cells in the neoplasm can be leukemia, acute non-lymphocytic leukemia, acute lymphocytic leukemia, blast phase of chronic myelocytic leukemia, meningeal leukemia, pancreatic cancer, ovarian cancer, breast cancer, non-small cell lung cancer, B-cell chronic lymphocytic leukemia, hairy cell leukemia, relapsed acute lymphoblastic leukemia, or refractory acute lymphoblastic leukemia cells. For example, the representative neoplastic cells that express dCK can be L1210 murine leukemia cells and the representative neoplastic cells that do not express dCK can be L1210-10K murine leukemia cells. PET imaging can be used to determine a local concentration of the PET probe in the neoplasm. The local concentration of the PET probe can be compared with a baseline level. A local concentration of the PET probe substantially lower than the baseline level can be correlated with low dCK expression of the neoplasm. Low dCK expression of the neoplasm can be correlated with oncolytic nucleoside analog resistance. The baseline level can correspond, for example, to the mean of concentration of the PET probe in representative neoplastic cells that express dCK and concentration of the PET probe in representative neoplastic cells that do not express dCK. For example, the oncolytic prodrug can be cytosine arabinoside (Ara-C), fludarabine, cladribine, clofarabine, or gemcitabine.

In an embodiment according to the invention, a PET probe is a dCK substrate resistant to deamination by an enzyme, for example, cytidine deaminase (CDA) or adenosine deaminase. For example, the PET probe can be [$^{18}$F]L-FAC, [$^{18}$F]L-FXAC, [$^{18}$F]L-FBAC, [$^{18}$F]L-FCAC, [$^{18}$F]L-FFAC, [$^{18}$F]L-FRAC, [$^{18}$F]L-FMAC, [$^{18}$F]F-CA, D-2-$^{18}$F-CA, L-2-$^{18}$F-CA, D-3-$^{18}$F-CA, and L-3-$^{18}$F-CA.

BRIEF DESCRIPTION OF THE DRAWINGS

FIG. 1 is a diagram showing the identification of fluorinated deoxycytidine analogs retained in activated vs. naïve T lymphocytes and incorporated into DNA.

FIG. 2A presents the chemical structures of 15 compounds according to embodiments of the invention.

FIG. 5 shows the selectivity of [$^{18}$F]D-FAC for lymphoid organs.

FIG. 6 shows the increased [$^{18}$F]D-FAC retention in spleen and lymph nodes at the peak of the primary anti-tumor immune response.

FIG. 8 is a diagram showing micro-PET scans performed on BDC-2.5 T cell receptor transgenic mice to which [$^{18}$F] D-FAC has been administered.

FIG. 10 is a diagram showing the biodistribution of [$^{18}$F] D-FAC.

FIG. 12 is a shows [$^{18}$F]D-FAC microPET/CT imaging of human and murine malignancies.

FIG. 14 shows that deoxycytidine kinase (dCK) expression causes the retention of D-FAC.

FIG. 15 shows results of an in vivo study demonstrating that D-FAC can be used to predict resistance to widely used oncolytic prodrugs such as Gemcitabine and Ara-C.

FIG. 17 demonstrates that the intracellular accumulation (retention and phosphorylation) of [$^{18}$F]-CA and [$^{18}$F]L-FAC requires the expression of deoxycytidine kinase (dCK).

FIG. 18 shows the results of biodistribution studies of [$^{18}$F]L-FAC and [$^{18}$F]-CA in C57/BL6 mice.

FIG. 19 illustrates that [$^{18}$F]L-FAC is more resistant to deamination than [$^{18}$F]D-FAC according to in vivo studies in mice and data using human plasma.

FIG. 22 illustrates that [$^{18}$F]L-FAC can be used to predict gemcitabine resistance in vivo.

FIG. 25 illustrates that [$^{18}$F]L-FMAC is resistant to deamination.

FIG. 26 show [$^{18}$F]L-FMAC microPET images of lymphadenopathy in an animal model of systemic autoimmunity.

FIG. 30 presents PET/CT scans of a 56 year old human male with chronic pancreatitis.

DETAILED DESCRIPTION

Figure 1A:
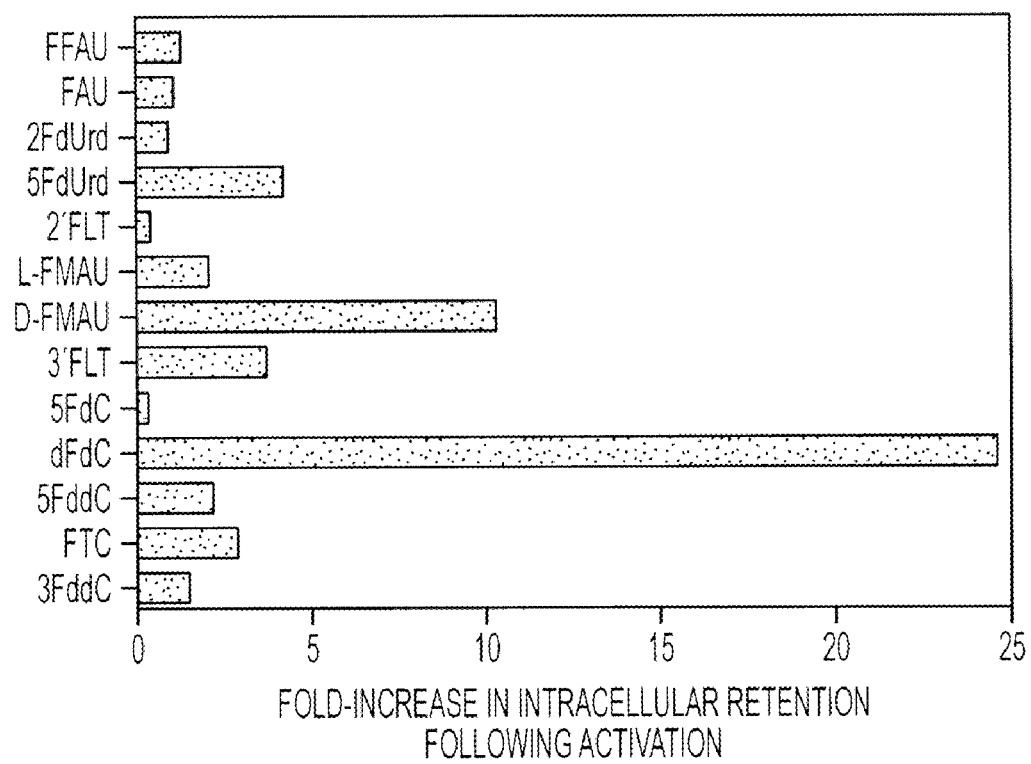
FIG. 1A shows the relative intracellular retention of several deoxycytidine analogs.
Figure 1B:
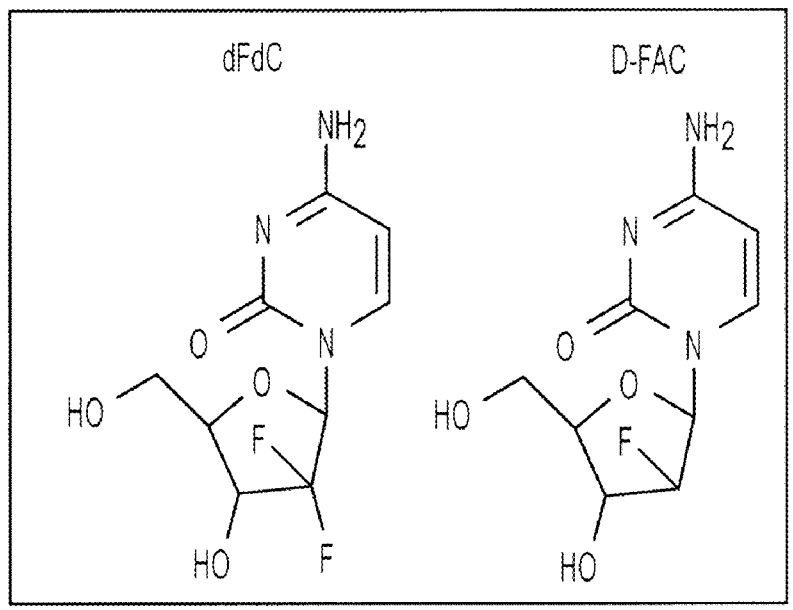
FIG. 1B shows the chemical structure of the dFdC and D-FAC compounds.
Figure 1C:
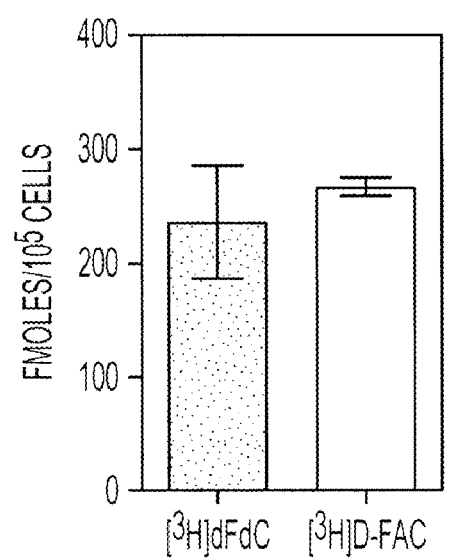
FIG. 1C shows the retention of [$^3$H] dFdC and [$^3$H]D-FAC by the activated mouse CD8+T cells.
Figure 1D:
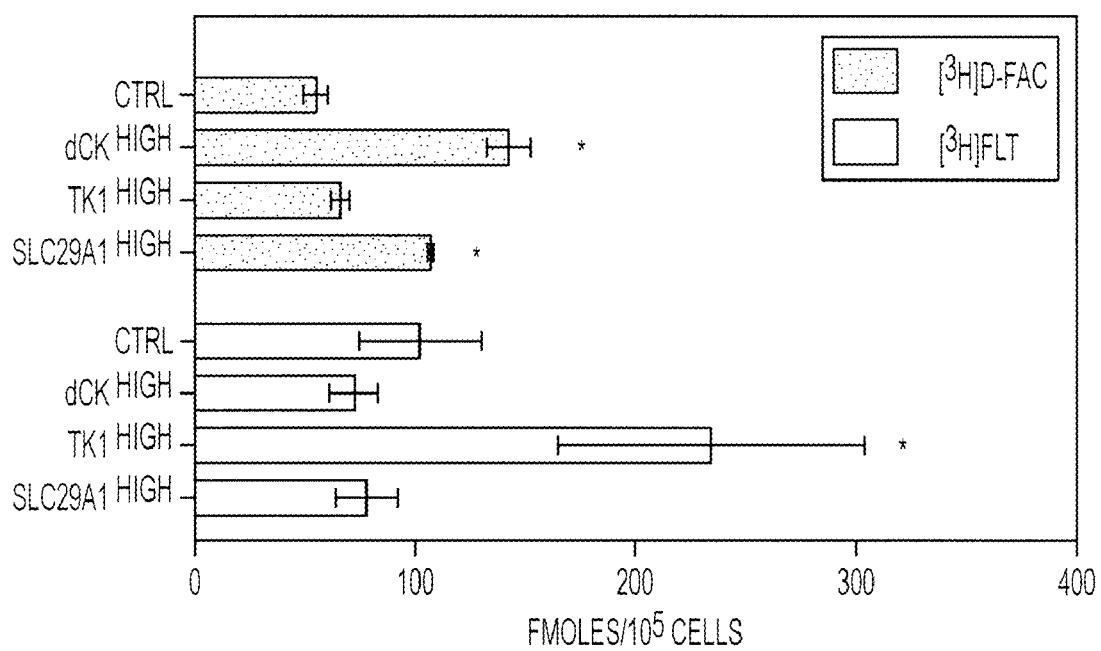
FIG. 1D shows the uptake of [$^3$H]D-FAC by cells.
Figure 1E:
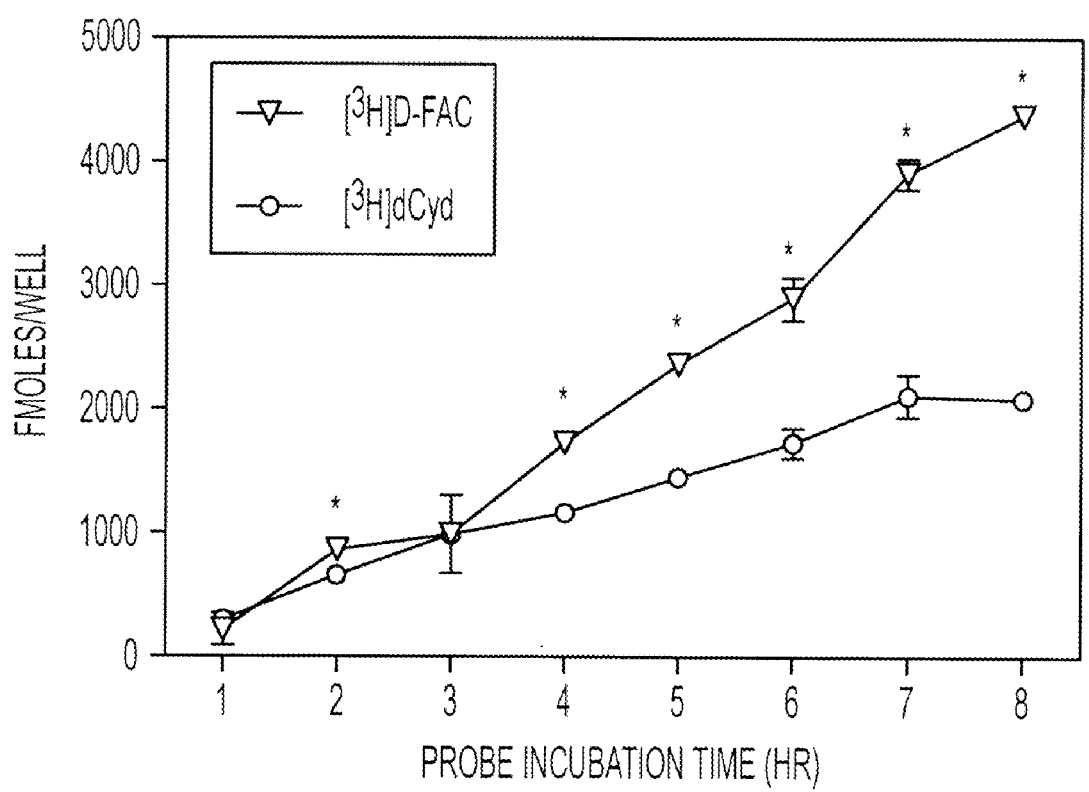
FIG. 1E shows incorporation of [$^3$H]D-FAC into the DNA of proliferating T cells.

Embodiments of the invention are discussed in detail below. In describing embodiments, specific terminology is employed for the sake of clarity. However, the invention is not intended to be limited to the specific terminology so selected. A person skilled in the relevant art will recognize that other equivalent parts can be employed and other methods developed without parting from the spirit and scope of the invention. All references cited herein are incorporated by reference as if each had been individually incorporated.

An objective of the work leading to the present invention, of which several embodiments are presented in this text, is the development of small molecule PET probes—other than 2-[$^{18}$F]fluoro-2-deoxy-D-glucose (herein, FDG) and such as, for example, 1-(2'-deoxy-2'-[$^{18}$F]fluoro-β-D-arabinofuranosyl)cytosine (herein, [$^{18}$F]D-FAC), [$^{18}$F]-CA, [$^{18}$F]L-FAC, [$^{18}$F]D-FMAC, [$^{18}$F]L-FMAC, [$^{18}$F]D-FBAC, [$^{18}$F]L-FBAC, [$^{18}$F]D-FCAC, [$^{18}$F]L-FCAC, [$^{18}$F]D-FFAC, [$^{18}$F]L-FFAC—that specifically target genes expressed during T lymphocyte activation or during malignant transformation. We have identified several chemical compounds that accumulate specifically in activated T lymphocytes and that can be labeled with the positron-emitting radioisotope [$^{18}$F]fluorine to generate PET probes for imaging the activation of lymphocytes in vitro and in vivo. These probes also enable the imaging of selected cancers and can be used to predict resistance to certain oncolytic nucleoside analogs.

In this text, when a compound is presented of which a substituent is stated to be a specific radioisotope or specified radioisotopes, it is to be understood that an agglomeration of more than one molecule of the compound that has one or more molecules in which the substituent is a different radioisotope or a stable isotope is encompassed. When a compound is presented of which a substituent is stated to not be a radioisotope, it is to be understood that an agglomeration of more than one molecule of the compound that has one or more molecules in which a substituent is a radioisotope, for example, a naturally occurring radioisotope that is represented in the agglomeration in a proportion found in nature, is encompassed.

In this text, when an enantiomer is discussed, the enantiomer of opposite handedness is also implied, unless the context indicates otherwise. The term [$^{18}$F]-CA implies either or both of the isomers 2-$^{18}$F-CA and 3-$^{18}$F-CA.

In another aspect, the present invention also relates to novel methods of synthesizing PET probes disclosed herein. In still another aspect, the present invention relates to methods of using PET probes in the diagnosis and treatment of diseases and conditions involving inflammation, e.g., rheumatoid arthritis, inflammatory bowel disease, type 1 diabetes, Experimental Autoimmune Encephalomyelitis (EAE), multiple sclerosis, atherosclerosis and cancer. As used herein, "treatment" comprises prevention, partial alleviation, or cure of the condition or disorder.

In another aspect, this invention relates to methods of evaluating the usage efficacy of particular classes of anticancer agents in the treatment of cancer such as those that are taken up into cells via nucleoside transporters and deoxycytidine kinase (dCK)-mediated phosphorylation. In an additional aspect, the present invention relates to methods of diagnosis and treatment of conditions that implicate cells with high deoxyribonucleoside salvage pathway activity, e.g., lymphocytes, bone marrow cells, and intestinal enterocytes. In another aspect, the present invention relates to compositions incorporating the compounds disclosed herein. In still another aspect, the present invention relates to kits comprising any embodiment of the present invention.

Monitoring immune function throughout the body using molecular imaging may significantly impact the diagnosis and treatment evaluation of immunological disorders. Positron Emission Tomography (PET) is a molecular imaging modality with numerous applications in cancer and other diseases. However, PET studies of immune function have been limited by a lack of specialized probes. Using a differential screening strategy, we identified PET probes for the deoxyribonucleotide salvage pathway. By way of reminder, these are probes other than 2-[$^{18}$F]fluoro-2-deoxy-D-glucose (herein, FDG). Examples of probes used are 1-(2'-deoxy-2'-[$^{18}$F]fluoro-β-D-arabinofuranosyl)cytosine (herein, [$^{18}$F]D-FAC), [$^{18}$F]-CA, [$^{18}$F]L-FAC, [$^{18}$F]D-FMAC, [$^{18}$F]L-FMAC, [$^{18}$F]D-FBAC, [$^{18}$F]L-FBAC, [$^{18}$F]D-FCAC, [$^{18}$F]L-FCAC, [$^{18}$F]D-FFAC and [$^{18}$F]L-FFAC.

The PET probes disclosed herein enabled lymphoid organ visualization by microPET that was sensitive to localized immune activation in mouse models of anti-tumor immunity. The PET probes disclosed herein also detected early changes of a lymphoid mass in systemic autoimmunity and allowed for evaluation of immunosuppressive therapy. These data support the use of PET probes disclosed herein for immune monitoring and suggest a wide range of clinical applications, including for treatment visualization of certain types of cancer.

Figure 9:
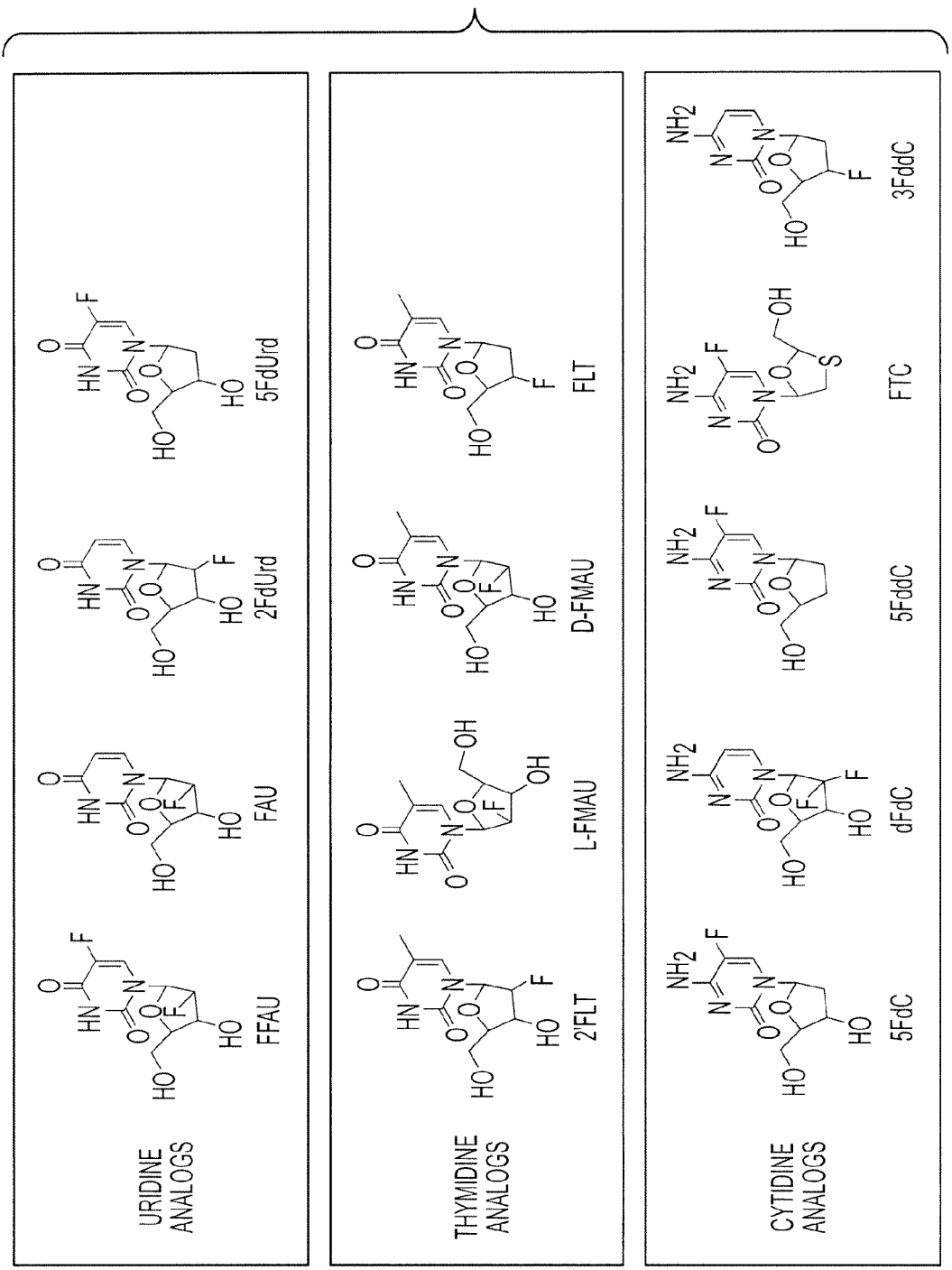
FIG. 9 shows the chemical structures of some of the fluorinated uridine, thymidine, and cytidine analogs discussed in this disclosure.

In order to identify candidates for PET probes that can distinguish between activated T cells and non-activated, naïve T cells, we conducted a radioactive uptake assay, the results of which are shown in FIG. 1. FIG. 1A shows the retention profiles for tested nucleoside analogs in activated and quiescent (naïve) T cells. These measurements were performed after incubating cells with radioactive compounds for 1 hr and performing successive washes to remove unincorporated probes. The structures and chemical formulas of tested compounds are shown in FIG. 9. Full names of the abbreviations for the compounds are provided in Table 1. The largest difference in probe retention by proliferating compared to naïve T cells was observed for 2',2'-difluorodeoxycytidine (dFdC) and was >20 fold (FIG. 1B). The results shown in FIG. 1 guided our design of [$^{18}$F]fluorine-radiolabeled PET probes analogous to 2'-deoxycytidine. For example, we identified compounds #1 through #15 (see FIG. 2A for chemical structures) as PET probe candidates useful for detecting activated T cells. FIG. 2A presents substrates of dCK labeled with the $^{18}$F positron emitting radioisotope.

TABLE 1

| URIDINE ANALOGS | |
|---|---|
| 2'-fluoro-2'-deoxy-5-fluorouracil-β-D-arabinofuranoside | FFAU |
| 1-(2-deoxy-2-fluoro-β-D-arabinofuranosyl)-uracil | FAU |
| 2'-fluoro-2-deoxyuridine | 2FdUrd |
| 5-fluoro-2-deoxyuridine | 5FdUrd |
| THYMIDINE ANALOGS | |
| 2'-fluoro-2'-deoxythymidine | 2'FLT |
| 1-(2-deoxy-2-fluoro-β-L-arabinofuranosyl)-5-methyluracil | L-FMAU |
| 1-(2-deoxy-2-fluoro-β-L-arabinofuranosyl)-5-methyluracil | D-FMAU |
| 3'-fluoro-3'-deoxythymidine | FLT |
| CYTIDINE ANALOGS | |
| 5-fluoro-2'-deoxycytidine | 5Fdc |
| 2',2'-difluorodeoxycytidine | dFdC |
| 5-fluoro-2,3-dideoxycytidine | 5FddC |
| (−)-β-2,3-dideoxy-5-fluoro-3-thiacytidine | FTC |
| 2,3-dideoxy-3-fluorocytidine | 3FddC |

Figure 3A:
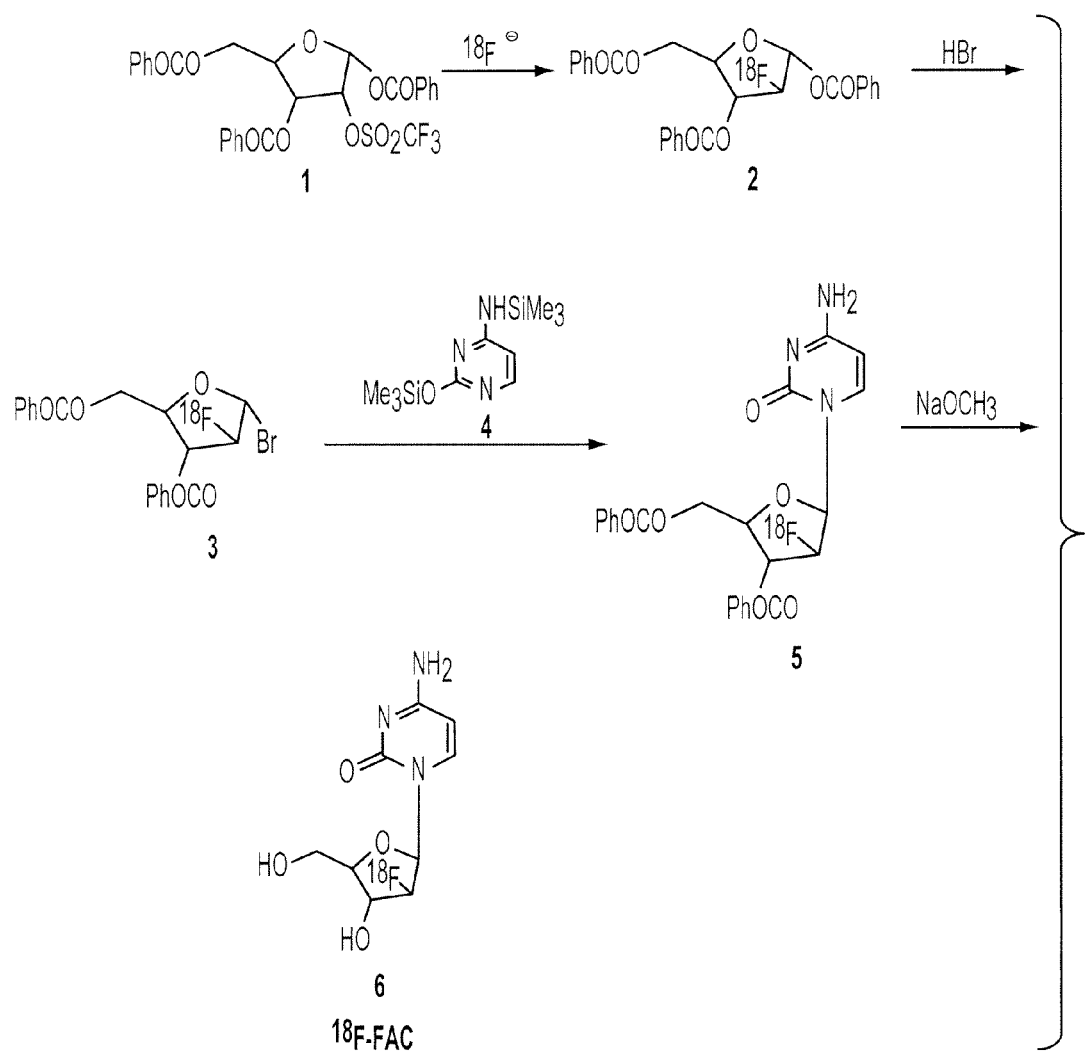
FIG. 3A presents the radiochemical synthesis of 1-(2'-deoxy-2'-[$^{18}$F]fluoroarabinofuranosyl)cytosine (herein, [$^{18}$F] D-FAC).

The synthesis of 1-(2'-deoxy-2'-[$^{18}$F]fluoro-β-D-arabinofuranosyl)cytosine (herein, [$^{18}$F]D-FAC) is illustrated in FIG. 3A. 2-O-[(Trifluoromethyl)sulfonyl]-1,3,5-tri-O-benzoyl-α-D-ribofuranose (1) can be reacted with [$^{18}$F]fluoride ion to produce 2-deoxy-2-[$^{18}$F]fluoro-1,3,5-tri-O-benzoyl-α-D-arabinofuranose (2) which can be reacted with hydrogen bromide to 2-deoxy-2-[$^{18}$F]fluoro-3,5-di-O-benzoyl-α-D-arabinofuranosyl bromide (3). The bromo compound 3 can be reacted with 4-N-(trimethylsilyl)-2-O-(trimethylsilyl)pyrimidine-4-amine (4) to produce 1-(2'-deoxy-2'-[$^{18}$F]fluoro-3,5-di-O-benzoyl-β-D-arabinofuranosyl)cytosine (5). The benzoyl-groups can be removed by reacting 5 with sodium methoxide to produce the PET probe, 1-(2'-deoxy-2'-[$^{18}$F]fluoro-β-D-arabinofuranosyl)cytosine (6).

Figure 3B:
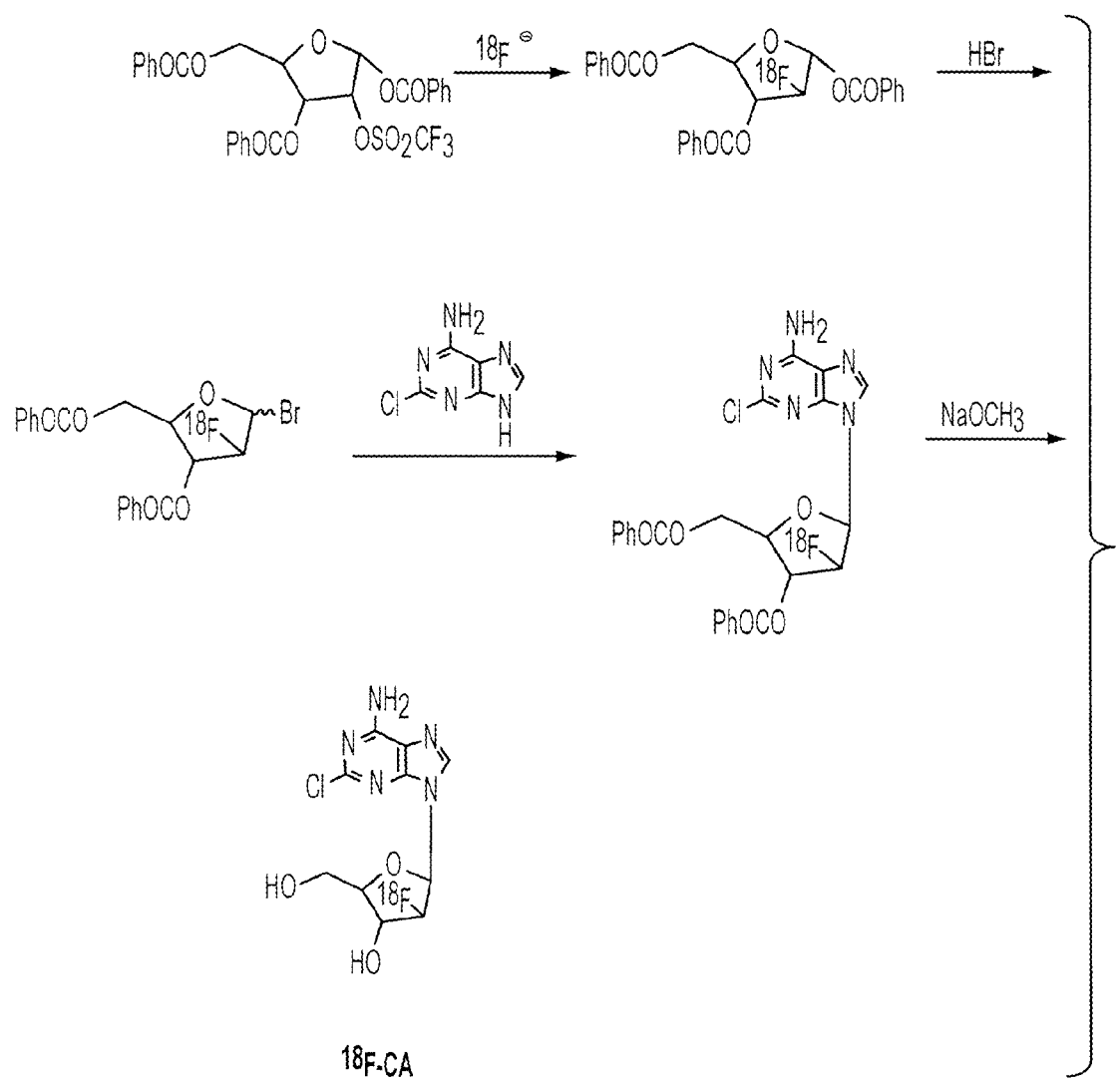
FIG. 3B presents the radiochemical synthesis of 2-chloro-9-(2-deoxy-2-[$^{18}$F]fluoro-β-D-arabinofuranosyl) adenine (herein, 2-$^{18}$F-CA).

The synthesis of 2-chloro-9-(2-deoxy-2-[$^{18}$F]fluoro-β-D-arabinofuranosyl)adenine (herein, 2-$^{18}$F-CA) is illustrated in FIG. 3B. 2-O-[(trifluoromethyl)sulfonyl]-1,3,5-tri-O-benzoyl-α-D-ribofuranose can be reacted with [$^{18}$F]fluoride ion to produce 2-deoxy-2-[$^{18}$F]fluoro-1,3,5-tri-O-benzoyl-α-D-arabinofuranose which can be reacted with hydrogen bromide to 2-deoxy-2-[$^{18}$F]fluoro-3,5-di-O-benzoyl-α-D-arabinofuranosyl bromide. The bromo compound can be reacted with 2-chloroadenine to produce 2-chloro-9-(4-benzoyloxymethyl-3-benzoyloxy-2-deoxy-2-[$^{18}$F]fluoro-β-Q-arabinofuranosyl)adenine. The benzoyl groups can be removed by reacting 2-chloro-9-(4-benzoyloxymethyl-3-benzoyloxy-2-deoxy-2-[$^{18}$F]fluoro-β-Q-arabinofuranosyl)adenine with sodium methoxide to produce the PET probe, 2-chloro-9-(2-deoxy-2-[$^{18}$F]fluoro-β-D-arabinofuranosyl)adenine.

Figure 4A:
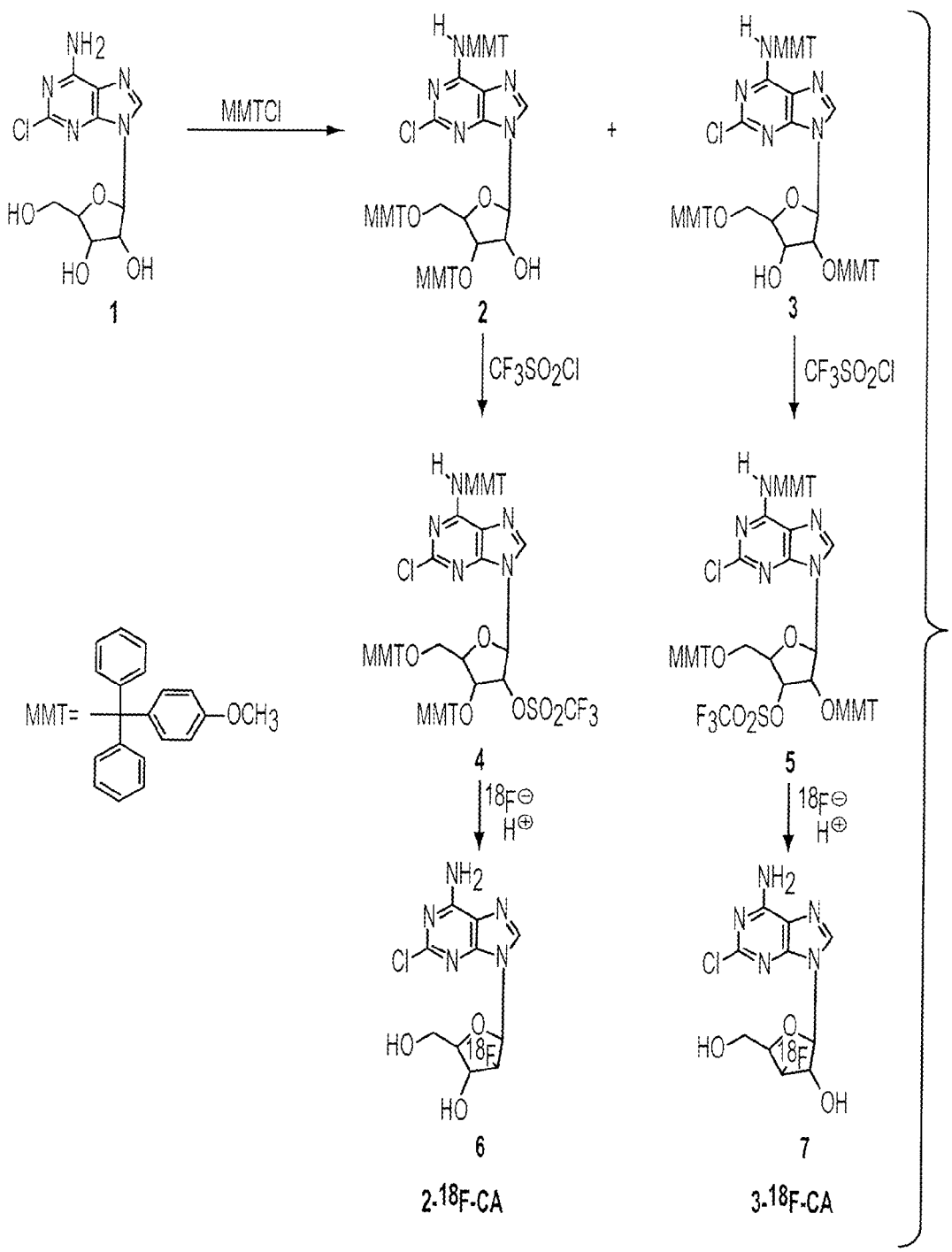
FIG. 4A through FIG. 4J present the radiochemical synthesis of 2-chloro-9-(2'-deoxy-2-[$^{18}$F]fluoro-β-D-arabinofuranosyl)adenine (herein, 2-[$^{18}$F]-CA), 3-[$^{18}$F]-CA, [$^{18}$F]L-FAC, [$^{18}$F]D-FMAC, [$^{18}$F]L-FMAC, [$^{18}$F]D-FBAC, [$^{18}$F]L-FBAC, [$^{18}$F]D-FCAC, [$^{18}$F]L-FCAC, [$^{18}$F]D-FFAC, and [$^{18}$F]L-FFAC.

The synthesis of 2-chloro-9-(2'-deoxy-2'-[$^{18}$F]fluoro-β-D-arabinofuranosyl)adenine (herein, [$^{18}$F]-CA) is illustrated in FIG. 4A. 2-Chloroadenosine (1) upon reaction with trityl chloride provided a mixture of alcohols 2 and 3 which were completely separated by silica gel column chromatography. The separated alcohols 2 and 3 were treated with triflyl chloride to yield the corresponding triflates 4 and 5. Reaction of the triflate 4 with [$^{18}$F] fluoride ion followed by deprotection of the trityl groups with dilute mineral acids such as HCl or H$_2$SO$_4$ gave 2-chloro-9-(2'-deoxy-2'-[$^{18}$F]fluoro-β-D-arabinofuranosyl)adenine (6) (herein, [$^{18}$F]CA or $^{18}$F-CA). Similarly, the reaction of the triflate 5 with [$^{18}$F]fluoride ion followed by deprotection with acids gave the isomeric 3'-deoxy-3'-[$^{18}$F]fluoro derivative 7. The synthesis of [$^{18}$F]L-FAC, [$^{18}$F]D-FMAC, [$^{18}$F]L-FMAC, [$^{18}$F]D-FBAC, [$^{18}$F]L-FBAC, [$^{18}$F]D-FCAC, [$^{18}$F]L-FCAC, [$^{18}$F]D-FFAC, [$^{18}$F]L-FFAC is shown in FIG. 4B-J.

Figure 2B:
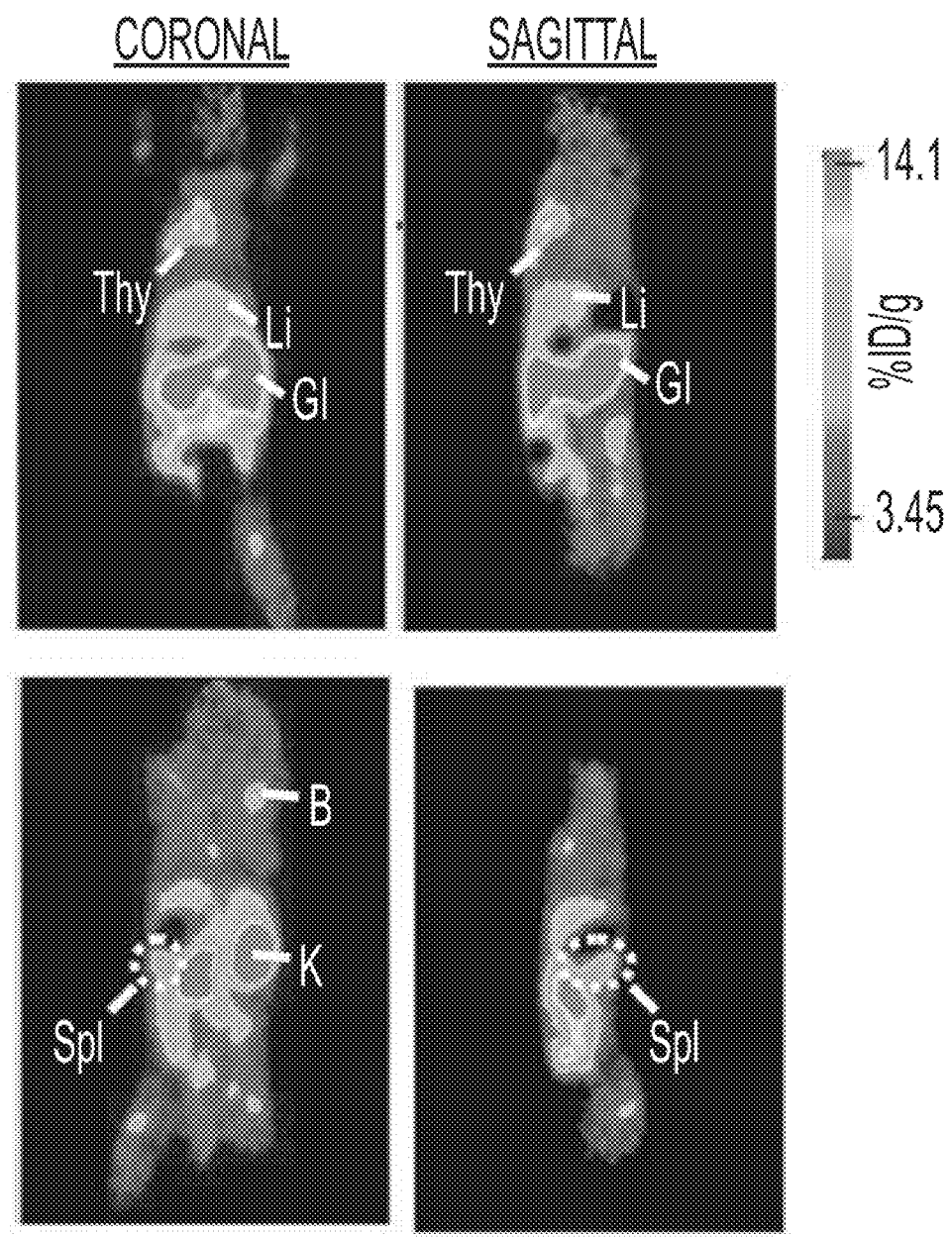
FIGS. 2B, 2C, and 2D show microPET scans using [$^{18}$F] D-FAC.
Figure 2C:
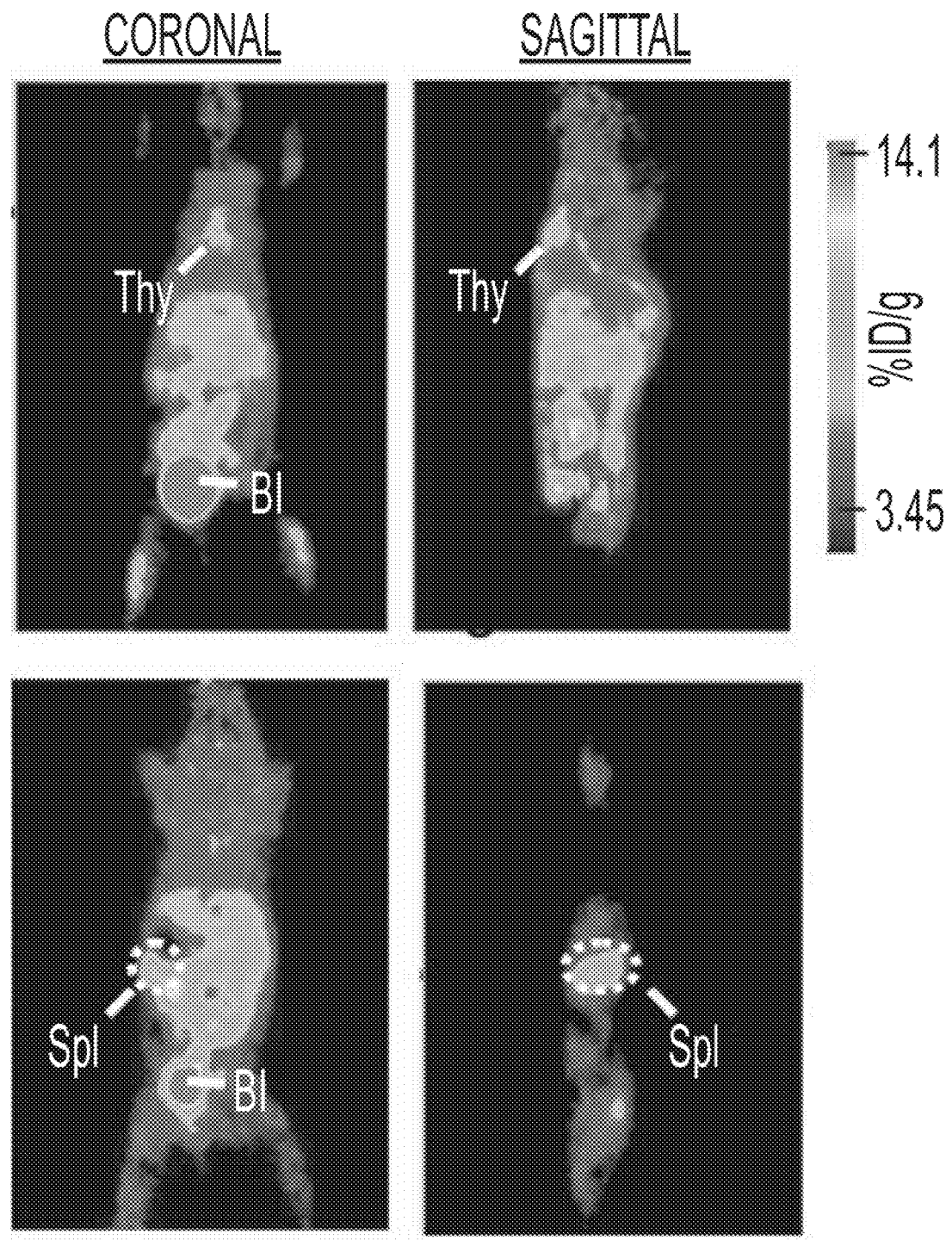
Figure 2D:
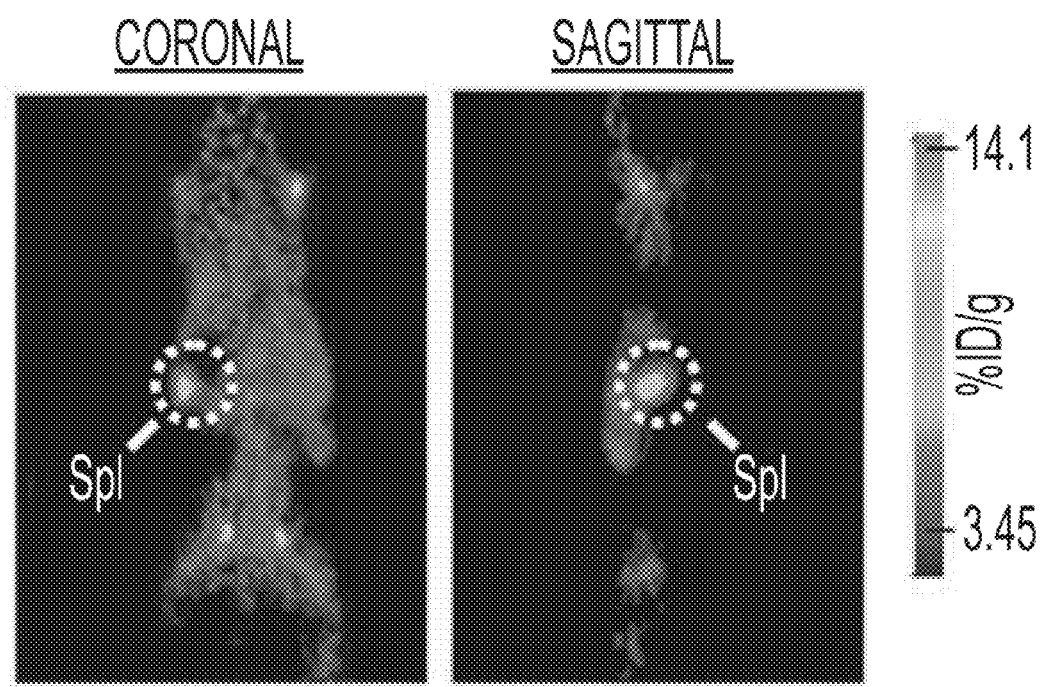

FIGS. 2B-2D show the [$^{18}$F]D-FAC microPET images of normal mice and mice undergoing systemic immune inactivation. FIG. 2B shows a naïve BL6 mouse injected with [$^{18}$F]D-FAC 1 hr prior to imaging; the PET imaging shows accumulation in the spleen and the thymus, the latter of which was predicted based on elevated dCK expression in that tissue. In FIG. 2C, a BL6 mouse was injected with 100 micrograms of anti-CD3 antibody 24 hr prior to imaging such that a systemic immune response can be generated. After the 1 hr uptake of [$^{18}$F]D-FAC, the probe accumulated in the spleen but there was less accumulation in the thymus because of antibody treatment. In FIG. 2D, the anti-CD3-stimulated mouse is imaged 2 hr after [$^{18}$F]D-FAC injection and shows that the probe clears from the kidneys such that clearer visualization of the spleen is possible.

In addition to [$^{18}$F]D-FAC (Compound #1), [$^{18}$F]L-FAC, (Compound #2), 2-chloro-9-(2'-deoxy-2'-[$^{18}$F]fluoro-β-D-arabinofuranosyl)adenine (herein, [$^{18}$F]CA, Compound #3), [$^{18}$F]D-FMAC (Compound #8) and [$^{18}$F]L-FMAC, (Compound #9), several other compounds can be useful for identifying activated T cells through deoxycytidine kinase-associated uptake detected by PET imaging; examples of these additional compounds are shown in FIG. 2A and FIG. 4. The compounds [$^{18}$F]D-FRAC and [$^{18}$F]L-FRAC can be useful for identifying activated T cells through deoxycytidine kinase-associated uptake detected by PET imaging. [$^{18}$F]D-FRAC is similar to [$^{18}$F]D-FMAC, and [$^{18}$F]L-FRAC is similar to [$^{18}$F]L-FMAC, except that instead of a methyl group substituted at the 5-position of the pyrimidine ring, an alkyl group having from 1 to 6 carbon atoms can be substituted at this position. The compounds [$^{18}$F]D-FXAC and [$^{18}$F]L-FXAC can be useful for identifying activated T cells through deoxycytidine kinase-associated uptake detected by PET imaging. [$^{18}$F]D-FXAC is similar to [$^{18}$F]D-FAC, and [$^{18}$F]L-FXAC is similar to [$^{18}$F]L-FAC, except that instead of a hydrogen substituted at the 5-position of the pyrimidine ring, a halogen, for example, fluorine, chlorine, bromine, or iodine, can be substituted at this position.

Thus, lymphocyte activation can be non-invasively monitored by injecting a subject animal or human with a trace amount of an [$^{18}$F]fluorine-labeled PET probe (e.g., such as in FIGS. 2-4), whereby the probe is expected to accumulate at sites of local immune activation and can be monitored at a whole body level using a PET scanner. The approach of using an [$^{18}$F]fluorine-labeled PET probe to monitor immune activation is that this probe would be more specific and sensitive than with an approach using FDG[31]. An [$^{18}$F]fluorine-labeled PET probe (like in FIGS. 2-4) can be administered to an animal or a human for diagnostic purposes such as to determine the presence or extent of a disease or disorder (e.g., cancer, autoimmune disease, developmental disorder, viral infection, bacterial infection, parasitical infection, other infections, metabolic disease, or inflammation). For instance, the [$^{18}$F]fluorine-labeled PET probe can be administered to monitor the progress of cancer or other disease-based types of immunotherapy, interferon therapy, vaccination, radiation therapy, and antibiotic therapy. (Notice that as used herein, "developmental disorder" includes immune deficiencies. Also as used herein, "metabolic disease" includes defects in macrophage function due to problems in enzyme storage.)

In the research context, the [$^{18}$F]fluorine-labeled PET probes presented in FIGS. 2, 3 and 4 can be administered to an animal for the purpose of developing a diagnostic technique, a therapy, or to develop a basic understanding of disease or disorder mechanisms.

We describe the identification and validation of new PET probes for the deoxyribonucleotide salvage pathway. PET imaging using probes (other than FDG) such as [$^{18}$F]D-FAC allows for visualization of the thymus and spleen in mice. Moreover, this technology is able to monitor alterations in the lymphoid mass and immune status under various experimental conditions. Current PET imaging work in EAE shows the utility of using [$^{18}$F]D-FAC for measuring key metabolic pathways in immune cells. While these probes are not exclusively retained in immune cell lineages, changes in probe accumulation throughout the body may be indicative of "disease states" and provide early biomarkers for treatment efficacy. Furthermore, the accumulation of [$^{18}$F]D-FAC in the thymus and spleen as well as the variations in [$^{18}$F]D-FAC retention at lymphoid organs during immune responses may reflect a critical role for the deoxyribonucleoside salvage pathway (as measured by the said probe) in T cell development and function. While the biological function of dCK is currently unknown, mice deficient in the dCK-related gene thymidine kinase 1 (TK1) display immunological abnormalities in histology and function. Novel genetic mouse models of dCK deficiency and imaging via [$^{18}$F]D-FAC PET may provide unique tools to dissect the immunological functions of the deoxyribonucleotide salvage pathway.

Figure 8A:
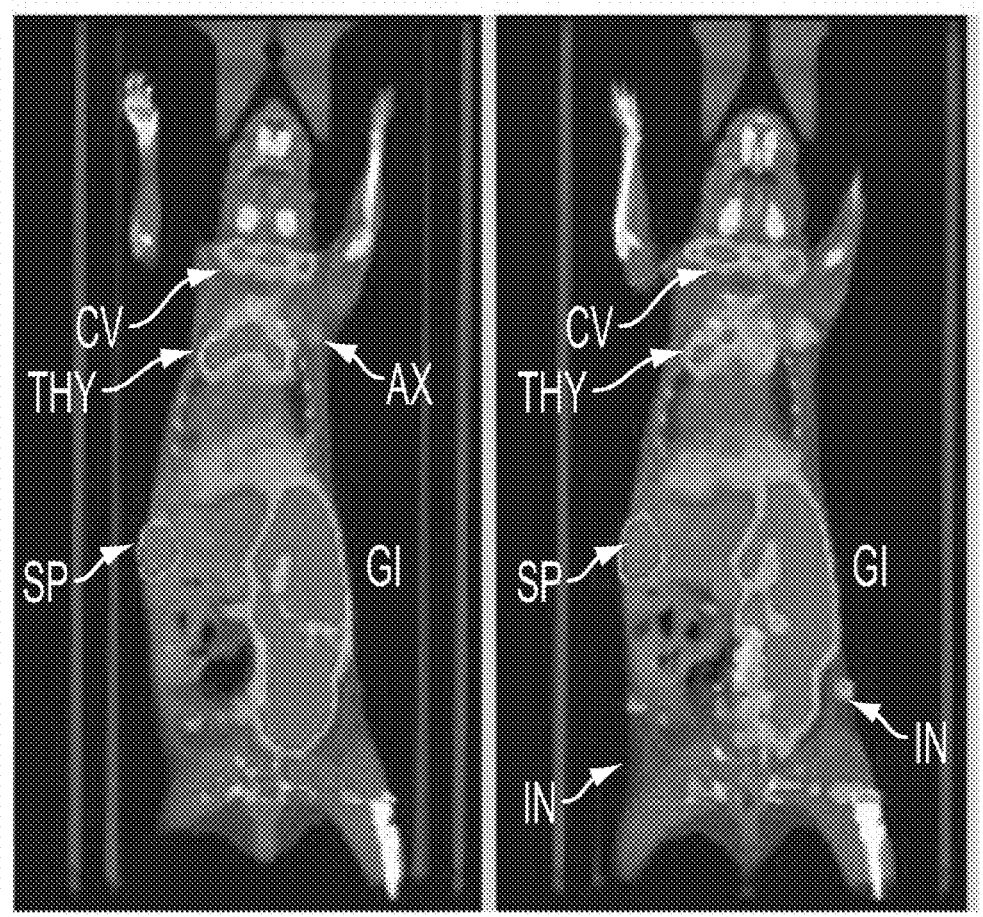
FIG. 8A shows microPET/CT images.
Figure 8B:
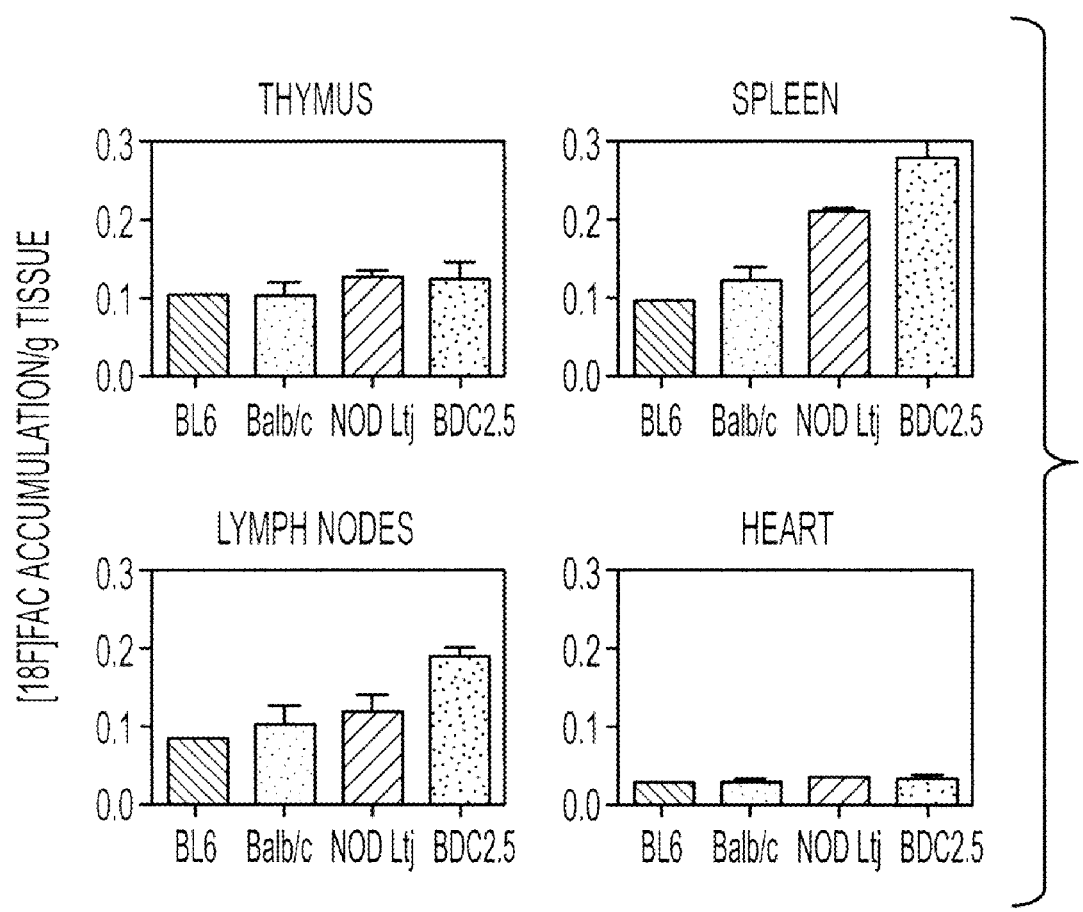
FIG. 8B presents [$^{18}$F]D-FAC accumulation measured in necroscopy tissue samples.

The unique distribution pattern of [$^{18}$F]D-FAC and other FAC analogs suggests that the utility of these probes may extend beyond the Fas$^{lpr}$ model to several other immune disorders. Elevated retention of the [$^{18}$F]D-FAC probe in joints and the intestine over physiologic uptake values may reflect the presence of an active inflammatory processes that is characteristic of rheumatoid arthritis and inflammatory bowel disease, respectively. [$^{18}$F]D-FAC microPET can also be used to detect overt autoreactive immune activation in a BDC-2.5 mouse model that is prone to type 1 diabetes (FIG. 8). In FIG. 8A, the 1 mm coronal sections illustrate the pattern of [$^{18}$F]D-FAC probe accumulation in BDC-2.5 mice. (Abbreviations: CV, cervical LNs; AX, axillary LNs; BR, brachial LNs; IN, inguinal LNs; THY, Thymus; GI, Gastrointestinal tract; H, heart.) In FIG. 8B, [$^{18}$F]D-FAC accumulation is measured in necropsy tissue samples from BL/6, BALB/c, NOD LTJ, and BDC-2.5 mice. The data indicate that of these strains, the spleen and lymph nodes of BDC2.5 mice accumulate the highest levels of [$^{18}$F]D-FAC.

The low retention of [$^{18}$F]D-FAC in the brain (FIG. 5) suggests that this probe is superior to FDG for detection of inflammatory infiltrates affecting the central nervous system in EAE and multiple sclerosis (MS). While it is not known whether [$^{18}$F]D-FAC can cross the blood-brain-barrier, the integrity of this structure is frequently compromised in EAE and MS. Regarding atherosclerosis, FDG has been shown to enable visualization of carotid plaques but its high accumulation in the myocardium limits imaging of coronary lesions. However, it is this very aspect of [$^{18}$F]D-FAC and in contrast to FDG, the lack of [$^{18}$F]D-FAC retention in the heart provides the necessary low background that can enhance PET imaging of activated macrophages and other immune cells at coronary atherosclerotic lesions (FIG. 5).

Figure 12A:
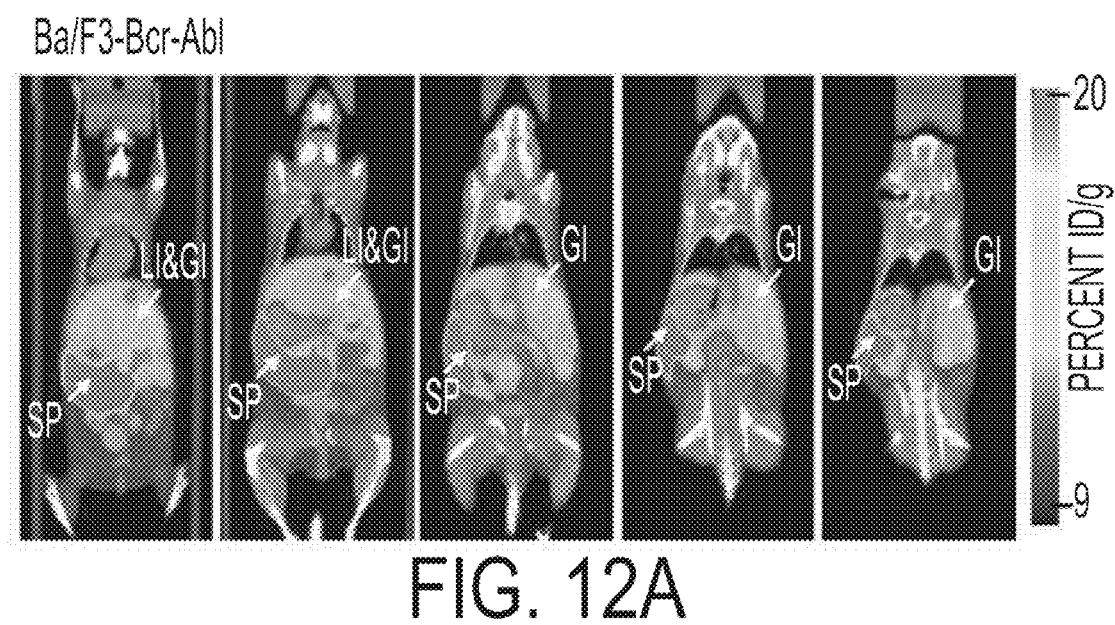
FIG. 12A shows the result of injecting SCID mice with Ba/F3 cells.
Figure 12B:
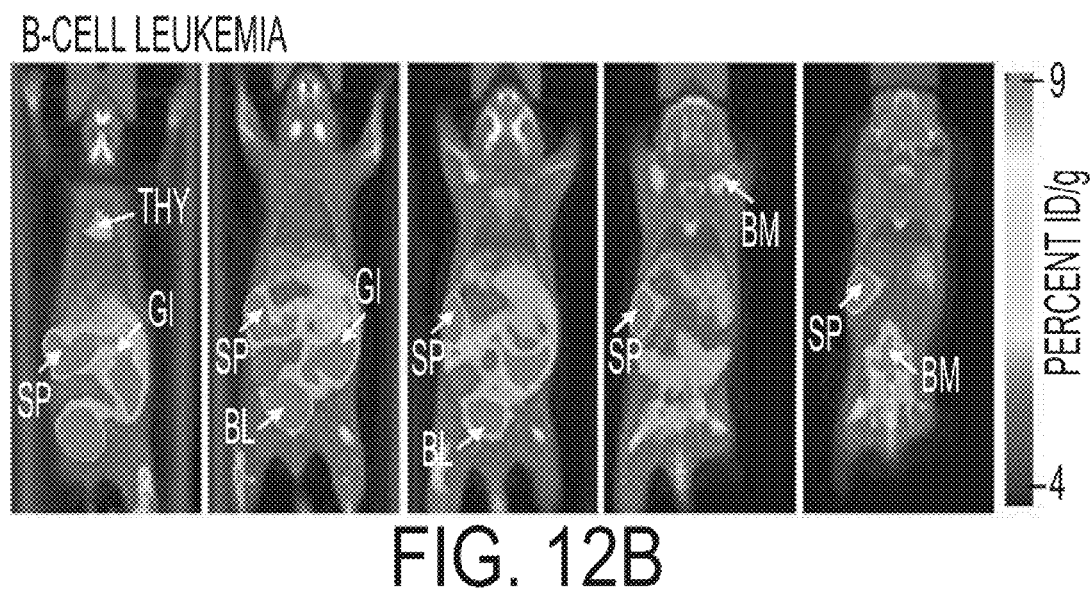
FIG. 12B shows the result of injecting NOD SCID mice with retroviral stock.
Figure 12C:
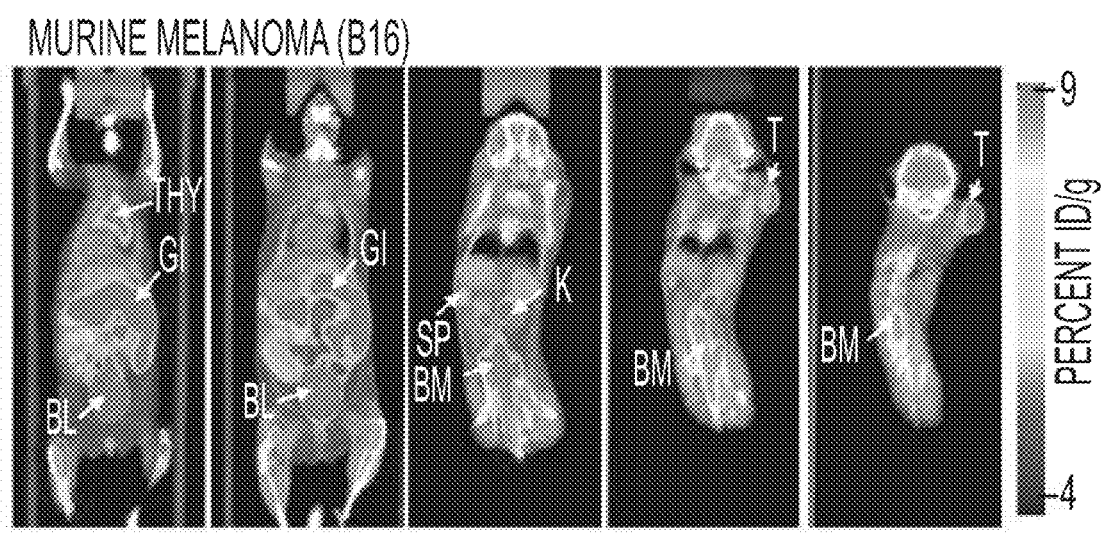
FIG. 12C shows the result of injecting C57BL/6 mice with B16 melanoma cells.
Figure 12D:
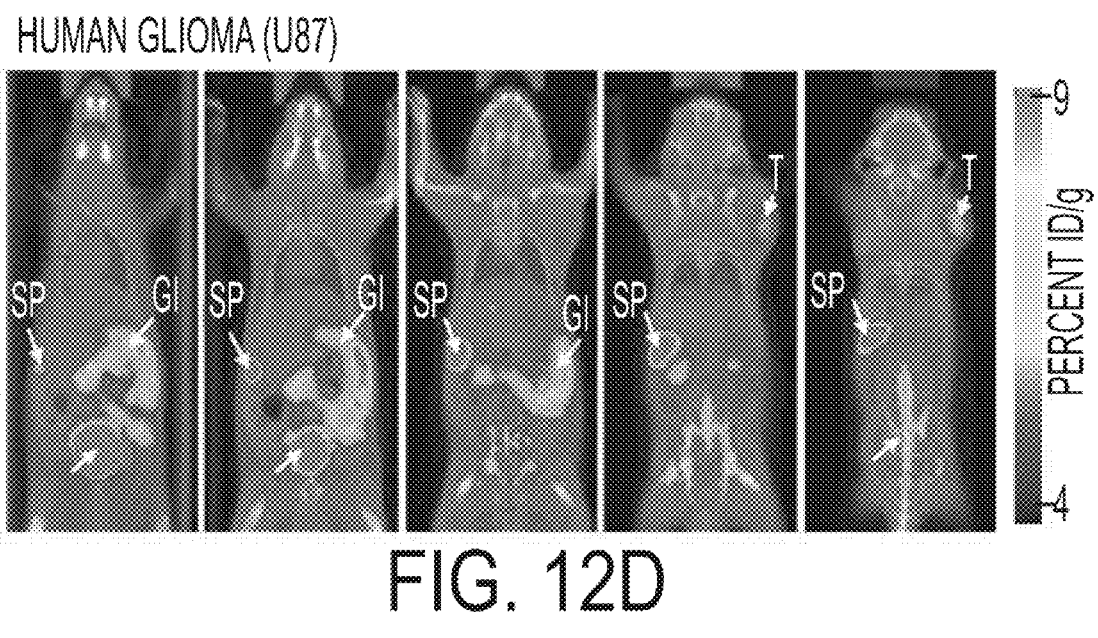
FIG. 12D shows the result of injecting SCID mice with U87 glioma cells.

In addition to immune diseases, [$^{18}$F]D-FAC may also be used to measure dysregulated nucleoside metabolism in cancer. To this end, we examined the utility of [$^{18}$F]D-FAC microPET in animal models representative of leukemia or lymphoma, melanoma, and glioma tumors (FIG. 12, where the images are 1 mm coronal sections from [$^{18}$F]D-FAC microPET/CT scans 1 hr after probe injection). In FIG. 12A, SCID mice were injected intravenously with Ba/F3 cells expressing p210 BCR-ABL and go on to develop aggressive disease with massive splenic infiltration that typically results in death within ~15 days (mice shown were imaged on day 12). In FIG. 12B, the NOD SCID mice were transplanted with wild type total bone marrow cells infected with MSCV-GFP-IRES-P185 BCR-ABL retroviral stocks and the leukemic mice were imaged 28 days following transplantation. In FIG. 12C, C57BL/6 was injected subcutaneously with $1 \times 10^5$ B16 melanoma cells and imaged 7 days later. In FIG. 12D, SCID mice were injected subcutaneously with $1 \times 10^6$ U87 glioma cells and imaged 10 days later. (Abbreviations: L, Liver; SP, Spleen; GI, Gastrointestinal tract; BL, Bladder; Tu, Tumor.) The increased [$^{18}$F]D-FAC retention in the spleen was observed in mouse models of oncogene-induced leukemia using Bcr-Abl-expressing Ba/F3 cells and Bcr-Abl transformed bone marrow. [$^{18}$F]D-FAC PET also detected implanted murine B16 cells (representative of malignant melanoma) and human U87 cells (representative of glioma tumors). [$^{18}$F]D-FAC may additionally be used to predict tumor responses to a particular class of anticancer agents, which include the widely used prodrugs cytarabine (Ara-C) and 2',2'-difluorodeoxycytidine (dFdC, Gemcitabine). Structurally, these prodrugs are closely related to FAC and require cellular uptake via nucleoside transporters and dCK-mediated phosphorylation for conversion to their active drug metabolites. We suggest that the availability of a PET biomarker to measure the cellular pharmacology of Ara-C and dFdC may assist with the stratification of susceptible and resistant tumors leading to a more rational clinical use of these important anticancer drugs.

Results presented here indicate that PET imaging with [$^{18}$F]D-FAC and the other inventive compounds offers new advantages in diagnostics and treatment monitoring of a wide range of disorders.

EXAMPLES

We considered the salvage pathway for DNA synthesis, in which deoxyribonucleosides are imported into cells by the specialized nucleoside transport proteins that are converted to their triphosphate forms via consecutive phosphorylation steps catalyzed by deoxyribonucleoside kinases. While the majority of normal tissues utilize the de novo pathway for deoxyribonucleotide synthesis, certain tissues—including thymus and spleen—rely extensively on the salvage pathway. Thus, we carried out the following studies: (i) in vitro screening of nucleoside analogs for retention in proliferating and quiescent T cells and identification of D-FAC, a new PET probe candidate; (ii) gene expression and biochemical analyses to investigate the mechanisms of elevated D-FAC retention in activated T cells; (iii) radiochemical synthesis of [$^{18}$F] D-FAC and in vivo biodistribution studies; (iv) comparison of [$^{18}$F]D-FAC with other PET probes currently used to measure nucleoside metabolism and glycolysis; and (v) evaluation of [$^{18}$F]D-FAC in mouse models of immune activation. Findings from these studies provide the impetus for translational [$^{18}$F] D-FAC PET imaging in a wide range of immunological disorders in patients. According to the invention, the strategy used to identify and evaluate [$^{18}$F]D-FAC and its analogs is broadly applicable to the development of new PET probes with defined specificity for various biochemical pathways and/or immune cell lineages.

The following nucleosides were purchased from Moravek Biochemicals (Brea, Calif.): 3'-Fluoro-3'-deoxythymidine (3'-FLT); 2'-Fluoro-2'-deoxythymidine (2'-FLT); 1-(2'-Deoxy-2'-fluoro-β-D-arabinofuranosyl)-5-methyluracil (D-FMAU); 1-(2'-Deoxy-2'-fluoro-β-L-arabinofuranosyl)-5-methyluracil (L-FMAU); 2',3'-Dideoxy-3'-fluorocytidine (3'-FddC); (-)-β-2',3'-Dideoxy-5-fluoro-3'-thiacytidine (FTC); 5-Fluoro-2',3'-dideoxycytidine (5FddC); 2',2'-Difluorodeoxycytidine (dFdC); 5-Fluoro-2'-deoxycytidine (5FdC); 5-Fluoro-2'-deoxyuridine (5FdURD); 2'-Fluoro-2'-deoxyuridine (2FdUrd); 1-(2'-Deoxy-2'-fluoro-β-D-arabinofuranosyl)-uracil (FAU); 2'-Fluoro-2'-deoxy-5-fluorouracil-β-D-arabinofuranoside (FFAU).

T lymphocytes from pmel-1 T cell receptor (TCR) transgenic mice were stimulated ex vivo using a melanoma antigen (1 micromolar hgp $100_{25-33}$). These cells were then cultured for radioactive uptake and kinase assays that were performed 72 hours post-stimulation. In more detail, 1 microCi of [$^3$H] D-FAC or [$^3$H]dFdC were added to a well containing $5 \times 10^4$ cells in a 96-well tissue culture plate and incubated for 1 hr at 37° C. and 5% $CO_2$. The plate was then washed 5 times with media containing 5% fetal calf serum (FCS) by using the Millipore Vacuum Manifold (Billerica, Mass.); the amount of incorporated probe was measured by scintillation counting using the PerkinElmer Microbeta (Waltham, Mass.).

Mice were kept warm, under gas anesthesia (2% isoflurane) and injected intravenously with 200 microCi of various PET probes; 1 hr was allowed for uptake. Mice were then positioned using an imaging chamber and the data was obtained using Siemens Preclinical Solutions (Knoxville, Tenn.) microPET Focus 220 and MicroCAT II CT systems. MicroPET data was acquired for 10 minutes and then reconstructed via statistical maximum a posteriori probability algorithms (MAP) into multiple frames[3]. The spatial resolution of PET is ~1.5 mm with 0.4 mm voxel size. CT images provide a low dose (400 micron) resolution acquisition with 200 micron voxel size. MicroPET and CT images were co-registered using a previously described method and regions were drawn using the AMIDE software (Andreas Loening, http://amide.sourceforge.net/, v0.8.16)[4,5]. Quantification was performed by drawing 3D regions of interest (ROI).

All the mice used in these studies were bred and maintained according to the guidelines of the Department of Laboratory Animal Medicine (DLAM) at the University of California, Los Angeles. For the oncoretrovirus-induced sarcoma model, C57/BL6 mice were challenged intramuscularly in the right triceps with the Moloney murine sarcoma and leukemia virus complex (MoMSV) in a volume of 100 uL of PBS as described previously[6]. B6-MRL-Fas$^{lpr}$/J mice used for systemic autoimmunity studies were purchased from the Jackson Laboratory (stock number 000482). To monitor the immunosuppressive treatment, these mice were given intraperitoneal injections of dexamethasone (DEX, 10 mg/kg) at 24 hr intervals and were scanned by microPET/CT 24 hr after the last injection. Animals were anesthetized with 2% isoflurane, injected intravenously with 200 microCi [$^{18}$F]D-FAC and then scanned with microPET/CT; mice were sacrificed immediately after imaging. Organs were rapidly excised, weighed, and the radioactivity was measured in a well counter. After decay correction, results were expressed as percent of the injected dose of activity per gram of tissue (% ID/g). Other mice were anesthetized with 2% isoflurane and injected intravenously with 1 mCi [$^{18}$F]D-FAC. After 1 hr, mice were euthanized, embedded in 3% carboxymethyl cellulose (CMC, Sigma), and frozen in 100% ethanol with dry ice for 45 min. The 50 micron sections were cut using a whole body cryostat, (PMV, Stockholm, Sweden); samples were exposed overnight on BAS-TR2025 plates (Fujifilm Life Science, Stamford, Conn.). Imaging plates were read using a Fujibas-5000 phosphorimager (16 bit, 25 micron resolution; Fujifilm Life Science).

The total RNA was extracted from the purified naïve CD8 T cells and 72 hrs post activation proliferating CD8 T cells of pmel-1 TCR transgenic mice. RNA was pooled from 4 independent experiments and hybridized to Affymetrix Mouse Genome 430 2.0 arrays. The absolute calls describing whether a probe set is present (P), marginally present (M), or absent (A) were generated using the Affymetrix GeneChip Operating Software v1.3 (GCOS) and expression values were calculated using the PM/MM difference model of DNA-Chip (dChip)[7]. Expression values across samples were normalized using dChip's invariant set method. As conditions for inclusion, a gene was considered differentially expressed if the corresponding probe set fit the following criteria: absolute call was P in at least half of the samples, fold change >1.4 between baseline (naïve CD8+T cells) and experimental (activated CD8+T cells) using the lower 90% confidence bound of fold change as defined in dChip, and expression difference between the baseline and experimental samples was >100. Genes involved in the nucleoside de novo biosynthesis and salvage pathways were taken from the KEGG database (pathway IDs 00230 and 00240, respectively) and the corresponding probe sets were manually extracted from Affymetrix's NetAffx to ensure complete coverage of all nucleoside pathway genes (239 probe sets) plus the SLC28 and SLC29 transporters (10 probe sets)[8,9].

Total RNA was purified from tissues using the Qiagen RNeasy Mini kit and 1.5 μg of this RNA was then used to synthesize cDNA using the TaqMan Reverse Transcription Reagents (Applied Biosystems). Pre-designed TaqMan assays were purchased from Applied Biosystems for dCK (Assay ID Mm00432794_m1), Slc29a1 (Assay ID Mm00452176_m1), and Slc28a3 (Assay ID Mm00627874_m1). TaqMan beta-actin (Applied Biosystems, Part: 4352341E) reagents were used as an endogenous control for quantification. The samples were ran out on a 48-well StepOne Real-Time PCR System (Applied Biosystems) and were analyzed with the StepOne Software v2.0 (Applied Biosystems) using the comparative Ct method ($\Delta\Delta Ct$). The qPCR mixture (20 μL) contained 15 ng cDNA, TaqMan buffer, 5.5 mM $MgCl_2$, 200 μM dATP, 200 μM dCTP, 200 μM dGTP, 400 μM dUTP, the appropriate TaqMan assay, 0.5 U AmpliTaq Gold, and 0.2 U uracil-N-glycosylase (UNG). Each assay included cDNA template in triplicates.

Six to 8 week old mice with severe combined immunodeficiency (NOD SCID) were sublethally irradiated (275 rads) one day prior to reconstitution. Whole bone marrow was isolated from the tibias and femurs of 4-8 week old wildtype mice and infected with MSCV-GFP-IRES-P185 BCR-ABL retroviruses. Three hours after infection, bone marrow cells were injected intravenously by the tail vein into recipient NOD SCID mice. Animals were monitored daily for signs of illness during a period of two months as previously described[10].

p210 BCR-ABL transfected Ba/F3 cell lines were previously described[11]. Ba/F3 cell lines were maintained in RPMI containing 10% FCS in 5% $CO_2$ at 37° C. (with the addition of 10% WEHI conditional medium as a source of IL-3 to the parental cell line). The spontaneous gp100+ murine melanoma B16 ($H-2^b$) cell line and the U87 glioma cell line were obtained from the American Type Culture Collection (ATCC, Rockville, Md.).

Graphs were constructed using GraphPad Prism software, version 4.02. P-values were calculated using Student's t test and only p-values of <0.05 were considered significant. Data are presented as means± standard errors of the mean (SEM).

In this text (including Figures and any other information presented), unless otherwise specified, the presentation, mention, or discussion of a chiral chemical compound also implies the presentation, mention, or discussion of each of the enantiomers of that chemical compound and their racemic mixtures. In this text (including Figures and any other information presented), unless otherwise specified, the presentation, mention, or discussion of a chemical compound with a specified chirality also implies the presentation, mention, or discussion of the enantiomer of that chemical compound with specified chirality and racemic mixtures of these.

Example 1

Differential Screening to Identify Potential Pet Probes Sensitive to Changes in Nucleoside Flux During T Cell Activation and Proliferation An in vitro assay (FIG. 1) was used to measure the retention of $^3H$-labeled nucleoside analogs (NA) in naïve and proliferating primary T cells. Selection criteria for tested NA accounted for the known propensity of fluorine substitutions to significantly change the stereoelectronic and biochemical properties of nucleosides. Thus, only deoxyribonucleosides containing 'cold' fluorine ($^{19}F$) atom substitutions were tested (FIG. 9). Subsequent substitution of $^{19}F$ with $^{18}F$ for radiochemical synthesis of PET probes would decrease the nuclear mass by a single atomic mass unit, which is a change of limited, if any, biochemical consequences. Moreover, only NA modified at the C-2' or 3' positions on the sugar moiety or at position 5 of the nucleobase were screened since fluorination at C-4' would be incompatible with radiochemical synthesis while fluorination at C-5' would prevent phosphorylation by nucleoside kinases.

FIG. 1 identifies fluorinated deoxycytidine analogs retained in activated versus naive T lymphocytes and incorporated into DNA. In FIG. 1A, T lymphocytes from pmel-1 T cell receptor (TCR) transgenic mice were stimulated ex vivo using a melanocyte/melanoma antigen (hgp $100_{25-33}$); after 72 hrs, the proliferating T cells were incubated for 1 hr with $^3H$-labeled (1 microCi) deoxyribonucleoside analogs (see FIG. 9). Following successive washes, intracellular radioactivity was measured by scintillation counting. This part of the figure shows the retention profiles for tested NA in activated and naïve T cells and the striking differences likely reflect differential expression of nucleoside transporters and kinases sensitive to the nucleobase structure and to fluorine substitutions of native hydrogen and hydroxyl groups. In FIG. 1B, 1-(2'-deoxy-2'-fluoro-arabinofuranosyl) cytosine (D-FAC) is a dFdC analog, amenable to $^{18}F$ labeling. Here, the largest (>20 fold) difference in retention was observed for 2',2'-difluorodeoxycytidine (dFdC) when proliferating T cells were compared to naïve T cells. FIG. 1C shows the retention of [$^3H$]dFdC and [$^3H$]D-FAC by the activated mouse CD8+T cells; notice that the F-ara analog 1-(2'-deoxy-2'-D-fluoroarabinofuranosyl) cytosine (D-FAC) resembled dFdC biochemically as indicated by their similar retention in proliferating CD8+T cells. In FIG. 1D, the increased uptake of [$^3H$]D-FAC was observed in NIH3T3 fibroblasts that were engineered to overexpress nucleoside kinases (dCK) and the nucleoside transporter SLC29A1. Note that [$^3H$]FLT was used as a positive control for TK1 expressing cells. Lastly, in FIG. 1E, [$^3H$]D-FAC is incorporated in the DNA of proliferating T cells.

Example 2

Biochemical Mechanisms of D-FAC Retention in Proliferating T Cells

Increased retention of D-FAC in proliferating T cells compared to naïve T cells may reflect any one or combination of several biochemical events: (i) upregulation of nucleoside transporters; (ii) elevated phosphorylation by deoxyribonucleoside kinases leading to intracellular trapping of charged products; and (iii) increased incorporation into the DNA. Gene expression analyses by microarray and qPCR were performed in T cells before and after activation (at 72 hrs) to determine the transcriptional status of specific nucleoside transporters and kinases. In terms of the context for D-FAC transport, previous studies using 2'-deoxycytidine (dcyd) analogs suggest the involvement of members of the solute carrier (SLC) families SLC28 and SLC29. SLC29A1 expression was upregulated by ~4-fold in proliferating T cells vs. naïve T cells while two other potential D-FAC transporters (SLC28A1 and SLC28A3) were not expressed in these cells (data not shown). D-FAC phosphorylation may be carried out by deoxycytidine kinase (dCK, Kcat/Km for dCyd=$2\times10^5$) and thymidine kinase 2 (TK2, Kcat/Km for dCyd=$3\times10^4$). Following T cell activation, dCK mRNA levels increased by ~2-fold whereas TK2 expression decreased by ~5-fold (data not shown). Collectively, these data suggest that [$^3$H] D-FAC retention in proliferating T cells reflects upregulation of SLC29A1 and that this allows increased availability of intracellular substrate and/or of dCK, which in turn leads to increased phosphorylation capacity. (Notably, SLC29A1 and dCK were both previously described to be involved in the metabolism of dFdC, a FAC-related nucleoside[12,13].)

Example 3

Figure 10A:
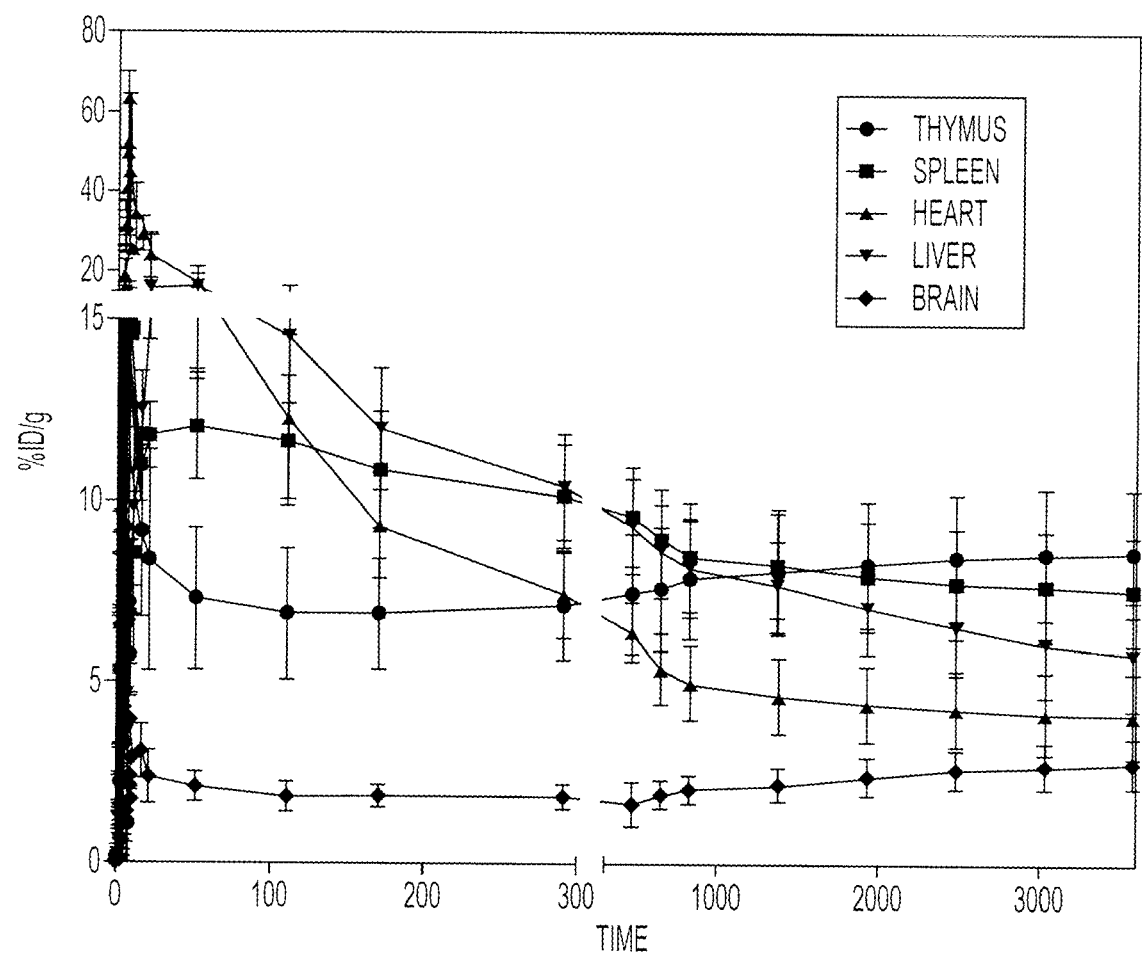
FIG. 10A shows decay-corrected mean time-activity curves in various organs of normal mice injected with [$^{18}$F] D-FAC determined from necroscopy tissue samples and indicative of [$^{18}$F]D-FAC accumulation.
Figure 10B:
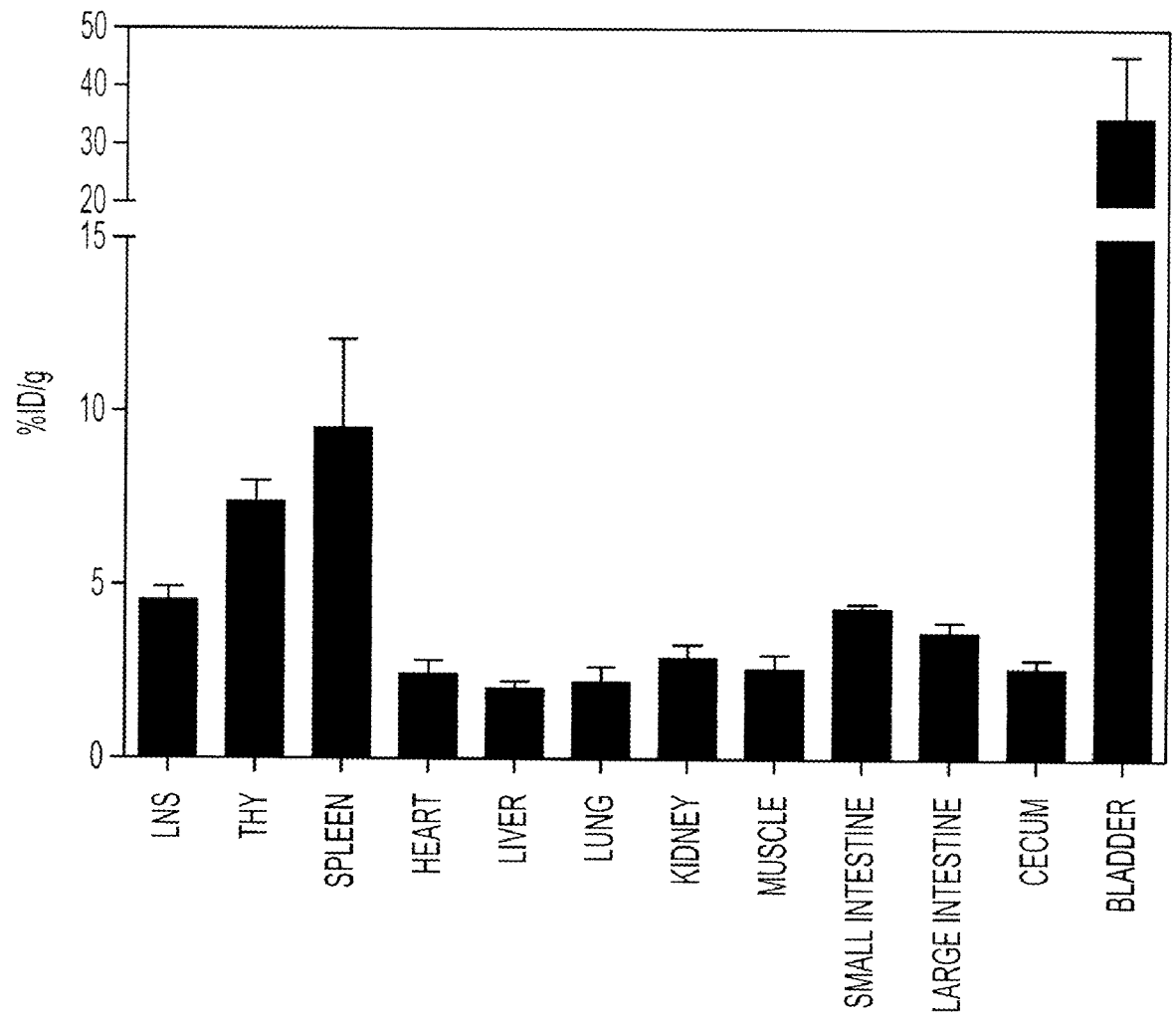
FIG. 10B shows [$^{18}$F]D-FAC biodistribution measured on necropsy tissue samples 60 min after injection.

[$^{18}$F]D-FAC has Greater Specificity for Lymphoid Organs than PET Probes Currently Used to Measure Nucleoside Metabolism and Glycolysis Biodistribution, metabolism, and clearance of [$^{18}$F]D-FAC were studied in C57/BL6 mice. Tissue decay-corrected mean time-activity curves obtained from dynamic [$^{18}$F]D-FAC microPET/CT scans suggest that [$^{18}$F]D-FAC is predominantly cleared through the kidney (FIG. 10). Time on the horizontal axis in FIG. 10A is in units of seconds. Imaging data were corroborated with measurements of retained radioactivity in necropsy tissue samples (FIG. 10B) and with digital whole-body autoradiography (DWBA, FIG. 5). One hour after intravenous injection of [$^{18}$F]D-FAC, the accumulated radioactivity was detected in the thymus, spleen, intestine, bone/bone marrow and, to a lesser extent, in the liver. Biochemical studies may determine whether [$^{18}$F]D-FAC biodistribution reflects tissue trapping by dCK-mediated phosphorylation, conversion to uracil metabolites via deamination (FIG. 11), or both. Regardless of the specific biochemical mechanism for retention, [$^{18}$F]D-FAC microPET and DWBA data suggest that this probe enables visualization of cells with high deoxyribonucleoside salvage pathway activity such as lymphocytes, bone marrow cells, and intestinal enterocytes[15].

Figure 11:
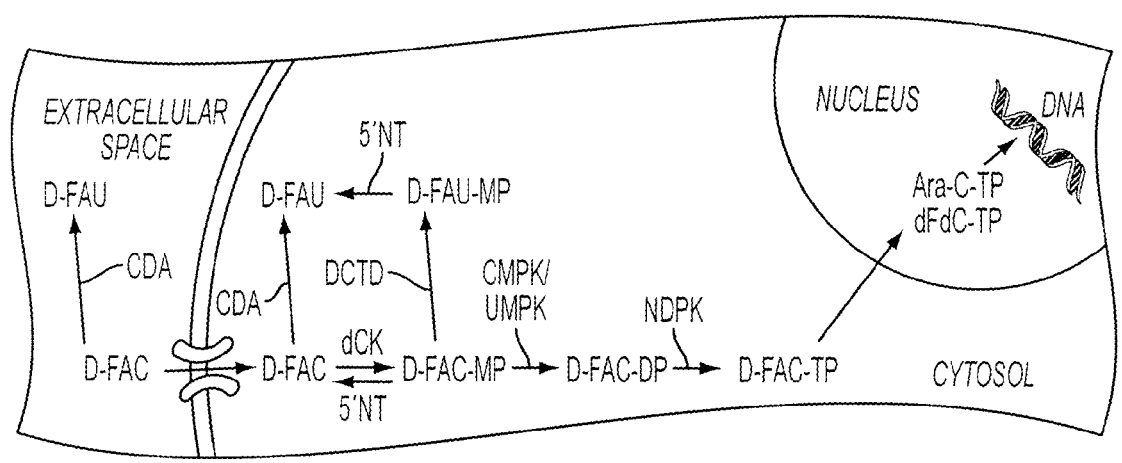
FIG. 11 is a cartoon showing potential metabolic pathways for [$^{18}$F]D-FAC.

FIG. 11 shows the potential biochemical pathway measured by [$^{18}$F]D-FAC. Putative transporters for D-FAC include SLC28A1, SLC28A3 and SLC29A1; however, only SLC29A1 is expressed in naïve and proliferating cells. Intracellularly, D-FAC is phosphorylated by deoxycytidine kinase (dCK) and can also be converted to its uracil metabolite D-FAU (1-(2'-deoxy-2'-fluoro-β-D-arabinofuranosyl)uracil) by cytidine deaminase (CDA), which can be inhibited by 3,4,5,6-tetrahydrouridine (THU). Monophosphorylated D-FAC (D-FAC-MP) is a potential substrate for cytidylate kinase (CMPK) and deoxycytidylate deaminase (DCTD). Diphosphorylated D-FAC (D-FAC-DP), which is a potential substrate for nucleoside diphosphate kinases (NME1, NME2, NME4, NME6, NME7), can inhibit ribonucleotide reductase (RRM), triphosphorylated D-FAC (D-FAC-TP), DCTD, and cytidine triphosphate synthase (CTPS). D-FAC-TP may be incorporated into DNA via DNA polymerase. Enzyme Commission (EC) numbers for the key enzymes involved in the nucleoside salvage pathway are as follows: CDA (3.5.4.5); CMPK (2.7.4.14); CTPS (6.3.4.2); dCK (2.7.1.74); DCTD (3.5.4.12); NME1, NME2, NME4, NME6, and NME7 (2.7.4.6); NT5 (3.1.3.5); POL (2.7.7.7); RRM (1.17.4.1); and TK1 (2.7.1.21).

Figure 5A:
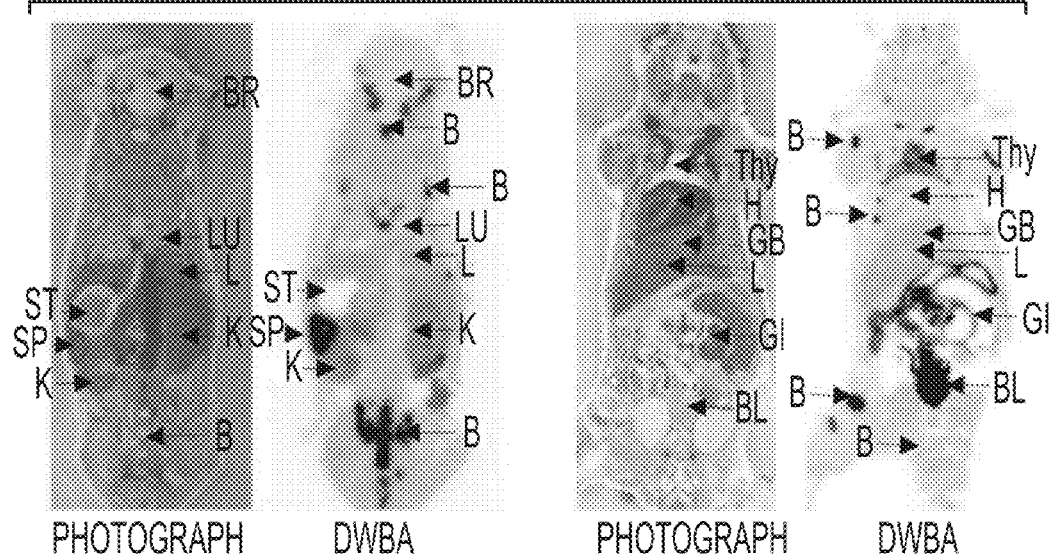
FIG. 5A shows a digital whole-body autoradiograph (DWBA)
Figure 5B:
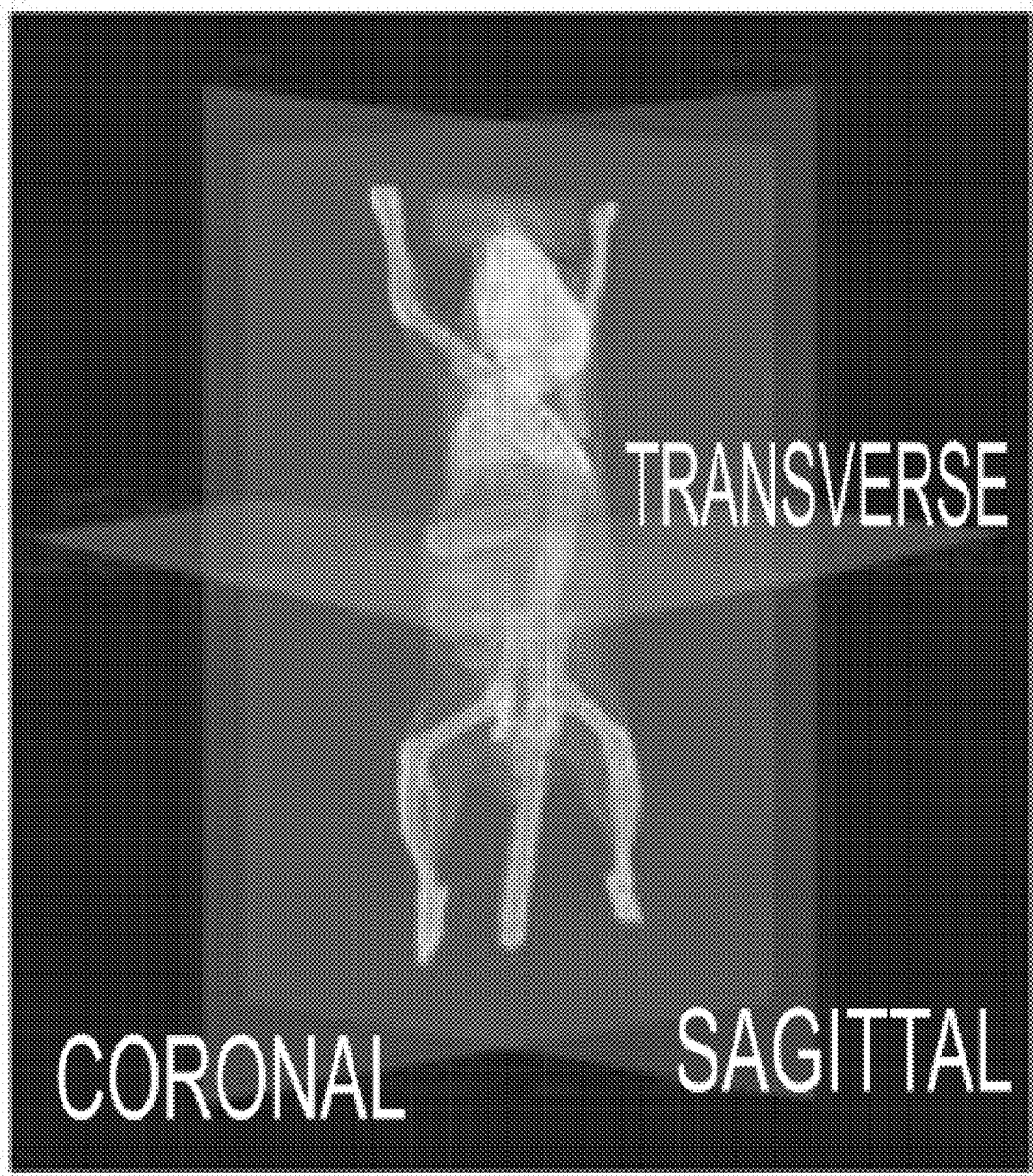
FIGS. 5B and 5C show microPET/CT scans.
Figure 5C:
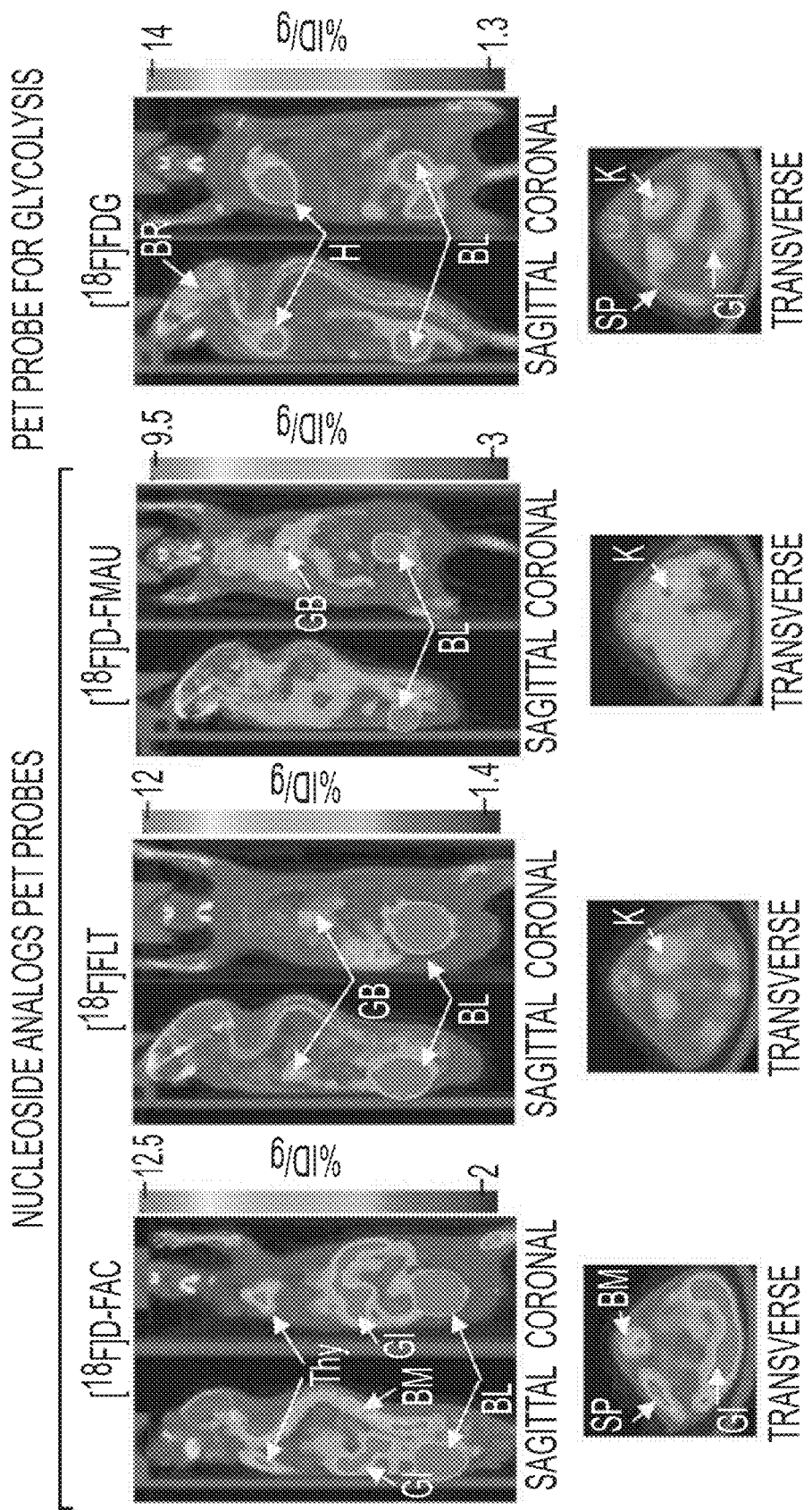
Figure 5D:
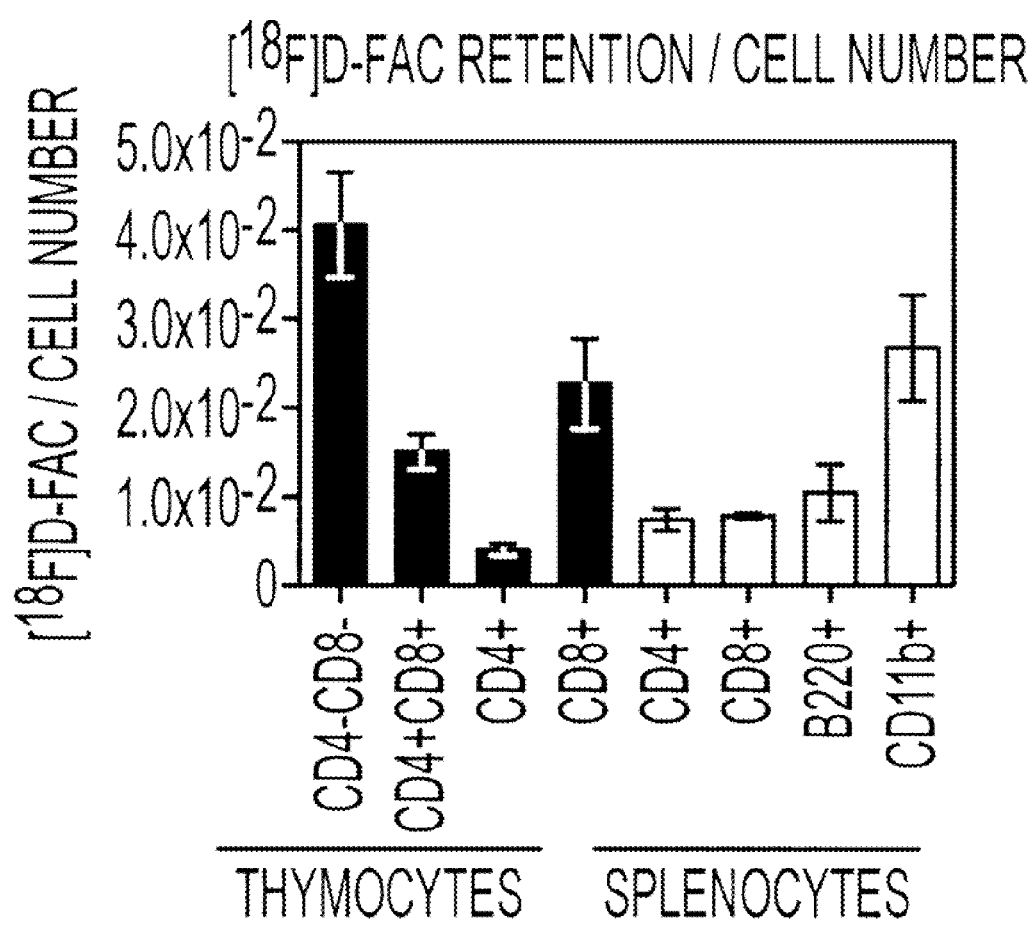
FIG. 5D shows the [$^{18}$F]D-FAC retention in thymocytes and splenocytes.
Figure 5E:
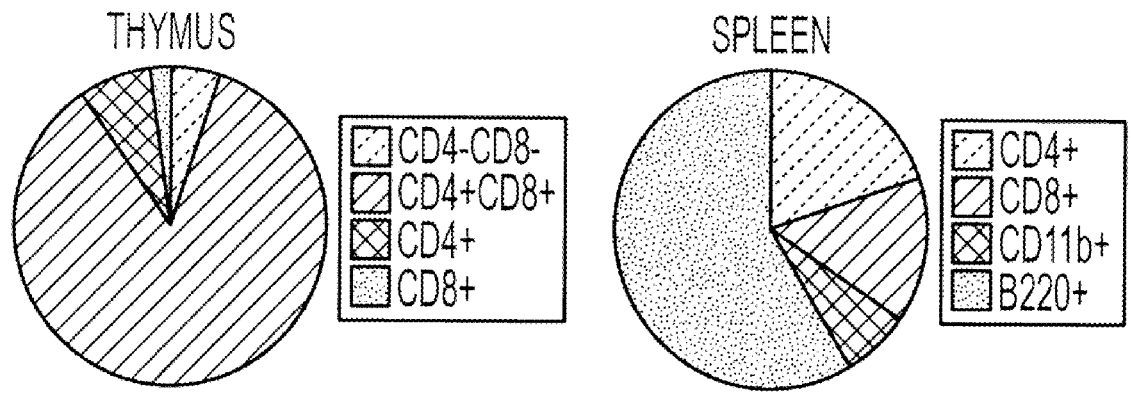
FIG. 5E shows the proportion of [$^{18}$F]D-FAC retention per cell lineage.

In FIG. 5A, [$^{18}$F]D-FAC digital whole-body autoradiography (DWBA) is shown along with the corresponding tissue section. The orientation of the sagittal, coronal, and transverse sections, 1 mm thick for each, are depicted in the 3D microCT image in FIG. 5B. In FIGS. 5B and 5C, an immunocompetent mouse (C57/BL6) was scanned by microPET/CT using probes for the dCK and TK1-dependent segments of the deoxyribonucleoside salvage pathway (namely, [$^{18}$F]D-FAC, [$^{18}$F]FLT, [$^{18}$F]D-FMAU) and for glycolysis (namely, [$^{18}$F]FDG). Mice were imaged 60 min after intravenous injection of the probes. Direct comparison of [$^{18}$F]FAC with probes for nucleoside metabolism—[$^{18}$F]FLT and [$^{18}$F]D-FMAU—and glycolysis—[$^{18}$F]FDG—further confirmed the ability of [$^{18}$F]FAC to provide functional imaging data that cannot be obtained using existing probes[16] (FIG. 5C and Table 1). In fact, neither [$^{18}$F]FLT nor [$^{18}$F]D-FMAU showed detectable accumulation in the thymus and spleen and the high retention in the myocardium limits the use of [$^{18}$F]FDG to visualize the thymus. To gain further insight into the cellular specificity of [$^{18}$F]D-FAC retention in the thymus and spleen, major immune cell types at these sites were isolated from mice injected with [$^{18}$F]D-FAC, sorted by flow cytometry, and counted in a well counter. In FIG. 5D, the [$^{18}$F]D-FAC retention per cell number in thymocytes and splenocytes is shown; here, the highest retention of radioactive probe per cell number was detected in double negative thymocytes, presumably reflecting intense cellular proliferation at this stage of T cell development. In FIG. 5E, the proportion of [$^{18}$F]D-FAC retention per cell lineage per lymphoid organ is displayed, which is, in other words, the fractional contribution of various immune populations to [$^{18}$F]D-FAC retention in the thymus and spleen. These data indicate that, in addition to T and B cells, [$^{18}$F]D-FAC also labels CD 11b$^+$ myeloid cells. (Abbreviations: B, bone; BL, bladder; BR, brain; GB, gall bladder; GI, gastrointestinal tract; H, heart; K, kidney; L, liver; LU, lung; SP, spleen; Thy, thymus; SC, spinal column; tissue % ID/g, the percent injected dose per gram.). Table 2 shows that amongst PET probes for nucleoside metabolic pathways and glycolysis, [$^{18}$F]FAC shows better selectivity for thymus and spleen than conventional probes (values are % ID/g per organ normalized to % ID/g muscle). Retention of [$^{18}$F]FDG in the thymus could not be measured because of signal spillover from the heart. Number of mice was 3.

TABLE 2

|  | [$^{18}$F]FAC | [$^{18}$F]FLT | [$^{18}$F]FMAU | [$^{18}$F]FDG |
|---|---|---|---|---|
| Spleen | 2.16 +/− 0.48 | 1.02 +/− 0.21 | 1.08 +/− 0.27 | 1.69 +/− 0.16 |
| Thymus | 3.29 +/− 0.48 | 1.22 +/− 0.23 | 1.33 +/− 0.24 | N.D. |

Example 4

Figure 6A:
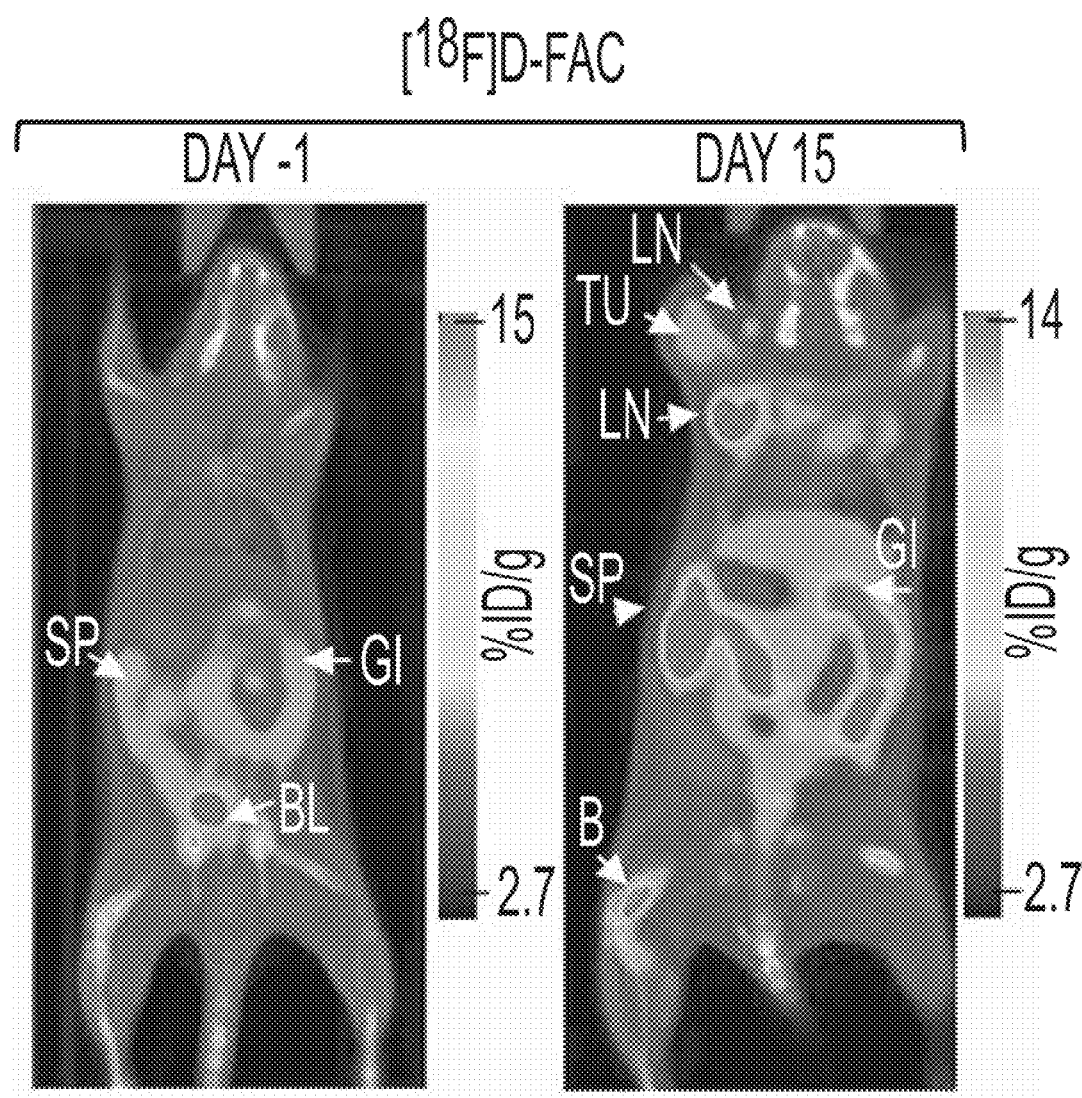
FIG. 6A shows a microPET/CT image.
Figure 6B:
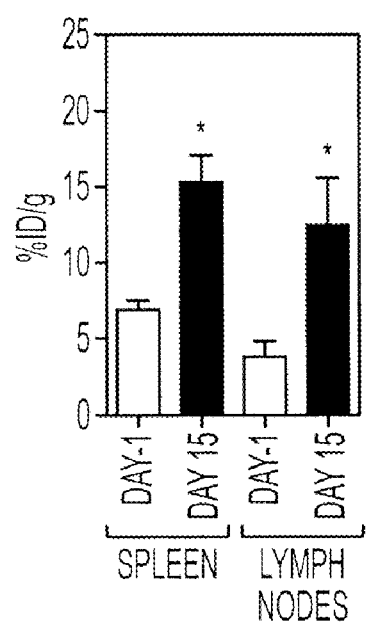
FIG. 6B shows the accumulation of [$^{18}$F]D-FAC in the spleen and lymph nodes.
Figure 6C:
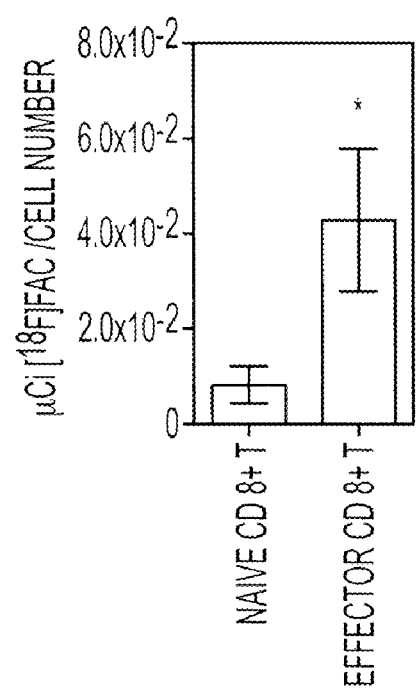
FIG. 6C shows the relative retention of [$^{18}$F]D-FAC in CD8+T and naïve cytotoxic T cells.

[$^{18}$F]D-FAC PET Imaging Detects Localized Changes in Immune Status During a Primary Anti-Tumor Immune Response Having established that [$^{18}$F]D-FAC allows for visualization of lymphoid organs in immunologically naïve mice, we investigated whether this probe can also be used to monitor immune responses in vivo using a well-studied oncoretrovirus tumor model in which mice are challenged with the Moloney murine sarcoma and leukemia virus complex (MoMSV) develop non-metastatic sarcomas. In this model, antigen-specific T cells primed by immunodominant epitopes encoded by viral gag and env genes rapidly expand in spleen and tumor draining lymph nodes (DLNs) and then traffic to the tumor lesion which is rejected over a period of 2-5 weeks[17,18]. In fact, the kinetics of T cell responses against MoMSV-induced sarcomas have been studied extensively using conventional ex vivo approaches and our group has used PET reporter gene imaging to visualize tumor rejection in this model[17]. To analyze whether the [$^{18}$F]D-FAC microPET/CT imaging can detect sites of localized immune activation, mice were scanned before and after the virus challenge. Relative to baseline scans (day 1), the scan acquired at the peak of the anti-tumor immune response (day 15) showed significantly increased [$^{18}$F]D-FAC accumulation in the spleen and tumor DLNs (FIGS. 6A and 6B). To further investigate the cellular basis of elevated [$^{18}$F]D-FAC retention, splenic CD8+T cells from mice injected with [$^{18}$F]FAC were fractionated by flow cytometry into naïve (CD62LHIGH/CD44LOW) and effector populations (CD62LLOW/CD44HIGH). Radioactivity measurements showed that effector CD8+T cells retained ~4-fold more [$^{18}$F]D-FAC than naïve cytotoxic T cells (FIG. 6C). These data confirm our initial observations that were obtained using cultured naïve and activated T cells (FIG. 1).

Figure 6D:
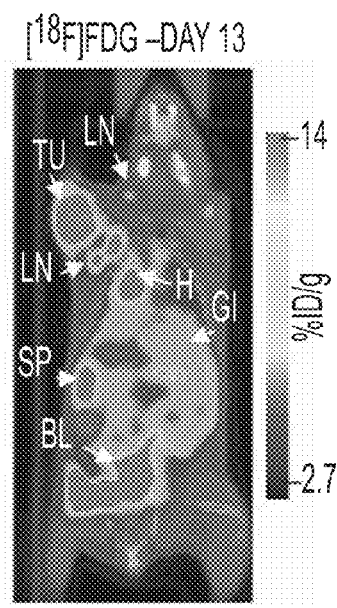
FIGS. 6D and 6E show microPET/CT images illustrating the accumulation of [$^{18}$F]FDG and [$^{18}$F]FLT probes.
Figure 6E:
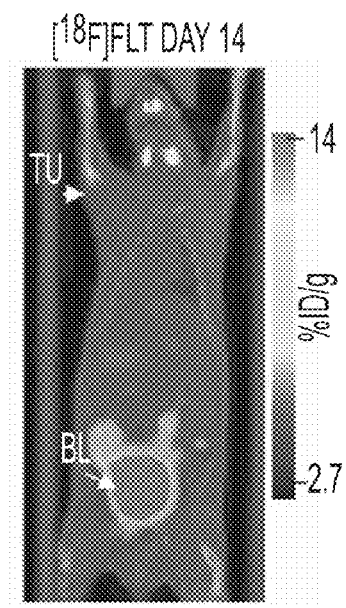

To determine whether [$^{18}$F]D-FAC can provide unique information regarding localized immune activation via the afore-mentioned model, the mice imaged by [$^{18}$F]D-FAC were also scanned on consecutive days using [$^{18}$F]FDG and [$^{18}$F]FLT. As shown previously, elevated [$^{18}$F]FDG accumulation was detected on day 13 post-virus challenge not only at the tumor but also at tumor DLNs and the spleen (FIG. 6D). In particular, tumor lesions accumulated high amounts of [$^{18}$F]FDG, namely 8.2±4.2 percent injected dose of activity per gram of tissue (% ID/g) tumor over background, which was defined as the contralateral muscle tissue. In contrast, [$^{18}$F]D-FAC retention in the tumor was significantly lower (1.9±0.3% ID/g tumor over background). The preferential accumulation of [$^{18}$F]D-FAC in the tumor DLNs (at 13±2.7% ID/g) compared to the tumor (at 6.7±0.3% ID/g) suggests that [$^{18}$F]D-FAC is a more specific probe than [$^{18}$F]FDG for imaging anti-tumor immunity in the oncoretrovirus model (FIGS. 6A and 6D). Moreover, no detectable [$^{18}$F]FLT accumulation was observed on day 14 at sites of immune activation that can be clearly visualized by [$^{18}$F]D-FAC and [$^{18}$F]FDG (FIG. 6D). The marked difference between these nucleoside PET probes may reflect the high level of thymidine present in the rodent serum that competes with [$^{18}$F]FLT and/or may reflect better sensitivity of [$^{18}$F]D-FAC for measuring the rate of the deoxyribonucleoside salvage pathway in immune cells.

Example 5

Figure 7:
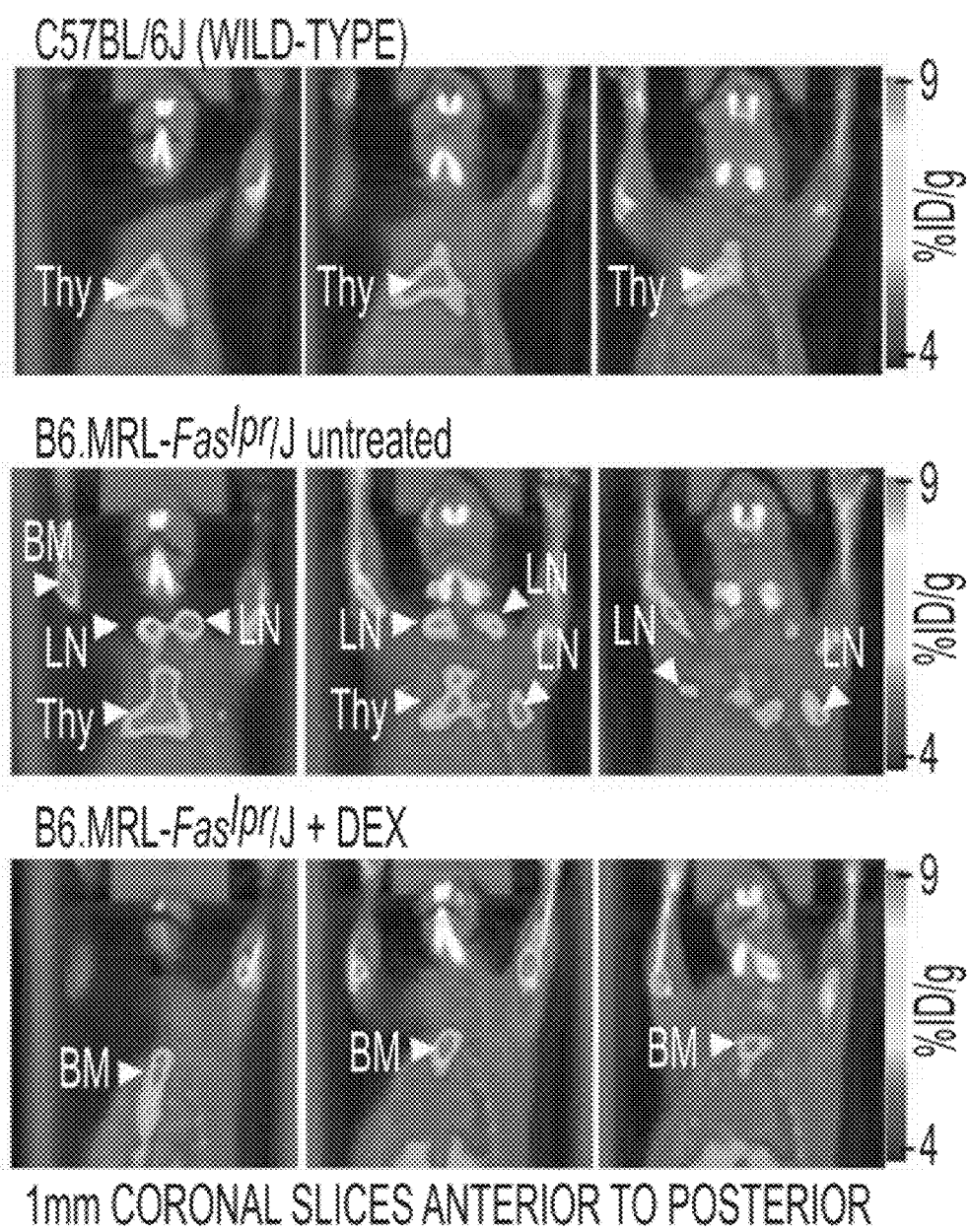
FIG. 7 shows that [$^{18}$F]D-FAC microPET/CT allows visualization of increased lymphoid mass associated with systemic autoimmunity and can be used to monitor immunosuppressive therapeutic interventions.

Disease and Treatment Evaluation Using [$^{18}$F]D-FAC PET in Animal Models of Autoimmunity We also asked whether [$^{18}$F]D-FAC enables monitoring of a systemic autoimmune disorder such as the Fas$^{lpr}$ syndrome, which is a well-studied animal model resembling human systemic lupus erythematosus. In this syndrome, deficient apoptosis of lymphocytes carrying the Fas$^{lpr}$ mutation results in lymphadenopathy, arthritis, and immune complex-mediated glomerulonephrosis. We used B6-MRL-Fas$^{lpr}$/J mice since they show significantly slower disease progression than the original MRL/Mp-1pr/1pr strain. MicroPET/CT scans of 2-3 month old B6-MRL-Fas$^{lpr}$/J mice revealed a significant increase in the numbers of [$^{18}$F]D-FAC positive axillary and brachial LNs relative to age-matched wildtype C57BL/6J controls (FIG. 7). The images were taken at 60 min after intravenous injection of [$^{18}$F]D-FAC and show three 1 mm thick coronal slices from wildtype (C57BL/6J) and B6-MRL-Fas$^{lpr}$/J both before and after treatment with DEX. (Abbreviations: Thy, thymus; LN, lymph nodes; B, bone). In summary, [$^{18}$F]D-FAC positive LNs were detected only in 2 out of 19 wild type mice, whereas microPET scans of Fas$^{lpr}$/J mice showed the presence of enlarged LNs in 9 out of 13 mice. To determine whether [$^{18}$F]D-FAC microPET/CT enables evaluation of therapeutic interventions, B6-MRL-Fas$^{lpr}$/J mice were treated with dexamethasone (DEX), a synthetic glucocorticoid that has pleiotropic, potent immunosuppressive effects. As shown in FIG. 7, DEX treatment (2-7 days) reduced [$^{18}$F]D-FAC retention in the thymus and peripheral LNs to undetectable levels. These findings suggest that [$^{18}$F]D-FAC microPET imaging allows for detection of lymphadenopathy at early stages of autoimmunity and indicate the utility of [$^{18}$F]D-FAC as a biomarker for monitoring the effects of immunosuppressive therapy.

FIG. 8 presents the results of microPET/CT imaging performed on BDC-2.5 T cell receptor transgenic mice injected with the [$^{18}$F]D-FAC probe. The BDC-2.5 strain is a well-established animal model for type I (autoimmunity-based) diabetes. In FIG. 8A, the 1 mm coronal sections illustrate the pattern of the [$^{18}$F]D-FAC probe accumulation in BDC-2.5 mice. (Abbreviations: CV, cervical LNs; AX, axillary LNs; BR, brachial LNs; IN, inguinal LNs; THY, Thymus; GI, Gastrointestinal tract; H, heart.) In FIG. 8B, [$^{18}$F]D-FAC accumulation is measured in necropsy tissue samples from BL/6, BALB/c, NOD Ltj and BDC-2.5 mice. The data indicate that among these strains, BDC-2.5 mice accumulate the highest levels of [$^{18}$F]D-FAC in the spleen and lymph nodes. The accumulation of [$^{18}$F]D-FAC probe in the lymphoid organs may indicate the activated status of the autoreactive T lymphocytes in the mouse.

Synthesis of Compounds

Example 6

Radiochemical Synthesis of 1-(2'-Deoxy-2'-[$^{18}$F] fluoro-β-D-arabinofuranosyl)cytosine ([18F]D-FAC)

2-O-[(Trifluoromethyl)sulfonyl]-1,3,5-tri-O-benzoyl-α-D-ribofuranose (1) (FIG. 3) was prepared as reported in the literature[27]. The synthesis of the $^{18}$F-fluoro analog 2 was carried out by a modification of the method reported by Mangner et al.[2]. No-carrier-added [$^{18}$F]fluoride ion was produced by 11 MeV proton bombardment of 98% enriched [$^{18}$O]water in a silver target body using a RDS-112 cyclotron. The aqueous [$^{18}$F]fluoride ion was treated with a solution of $K_2CO_3$ (1 mg) and Kryptofix 2.2.2 (10 mg) dissolved in water (0.04 mL) and acetonitrile (0.75 mL) mixture. The solution was evaporated at 115° C. with a stream of nitrogen gas. The residue was dried by the azeotropic distillation with acetonitrile (3×0.5 mL); specifically, a solution of the triflate 1 (10 mg) in 0.7 mL of acetonitrile was added to the dry residue before the reaction mixture was heated at 165° C. for 15 min in a sealed vessel. The solution was then cooled to room temperature and passed through a small cartridge of silica gel, from which the product was eluted with 5 mL of ethyl acetate. Next, the ethyl acetate solution was evaporated to dryness before 0.1 mL of 30% HBr in acetic acid solution and then 0.4 mL of dichloroethane were added sequentially. This new reaction mixture was heated at 80° C. in a sealed vessel for 10 min and the solution was concentrated to ~50% of the initial volume. In the following step, 0.7 mL of toluene was added and this solution was evaporated at 110° C. to give the bromo (compound 3). A freshly prepared disilyl derivative of cytosine (4, 35 mg) was dissolved in 1 mL of dichloroethane and added to the bromo compound 3. The condensation reaction was carried out at 160° C. in a sealed vessel for 30 min before the reaction mixture was cooled to room temperature and then passed through a small column of silica gel. The product was eluted off the column using 5 mL of a solution mixture of 10% methanol with 90% dichloromethane. This solution was evaporated to dryness at 100° C. and then treated with 0.5 mL of a solution of 0.5 M sodium methoxide in methanol. The reaction mixture was heated at 100° C. for 5 min in a sealed vessel and, thereafter, the basic reaction mixture was neutralized with 0.25 mL of 1M HCl in water. This reaction mixture was diluted to a total volume of 3 mL with a mixture of 1% ethanol with 99% 10 mM ammonium dihydrogen phosphate in water and injected into a semi-preparative HPLC column (Phenomenex Gemini C-18 column; 25 cm×1 cm). The HPLC column was eluted with a solvent mixture of 1% ethanol with 99% 10 mM ammonium dihydrogen phosphate at a flow rate of 5.0 mL/min. The effluent from the HPLC column was monitored with a 254 nm UV detector followed by a gamma radioactive detector. The chemically and radiochemically pure [$^{18}$F]D-FAC was eluted off the column with a retention time of ~15 min and the radiochemical yield ranged 20-30%.

The chemical and radiochemical purities of [$^{18}$F]D-FAC were determined by an analytical HPLC method using a Phenomenex Luna column (25 cm×0.46 cm, 5µ particle size). The column was eluted with 10% ethanol and 90% 50 mM ammonium acetate at a flow rate of 1.0 mL/min. The effluent from the HPLC column was passed through a UV detector (µ=254 nm) followed by a gamma radioactivity detector. The chemical and radiochemical purities of [$^{18}$F]D-FAC prepared as described above exceeded 99%.

Analytical HPLC also was used to determine the specific activity of [$^{18}$F]D-FAC. A range of mass vs UV absorption at 254 nm wavelength for non-radiolabeled D-FAC was determined using the analytical HPLC method described above and the data set was used to construct a calibration graph. Using this calibration graph, the specific activity of [$^{18}$F]D-FAC was found to be >1000 Ci/mmol.

Example 7

Radiochemical Synthesis of 1-(2'-deoxy-2'-[$^{18}$F] fluoro-β-L-arabinofuranosyl)cytosine ([$^{18}$F]L-FAC)

Figure 4B:
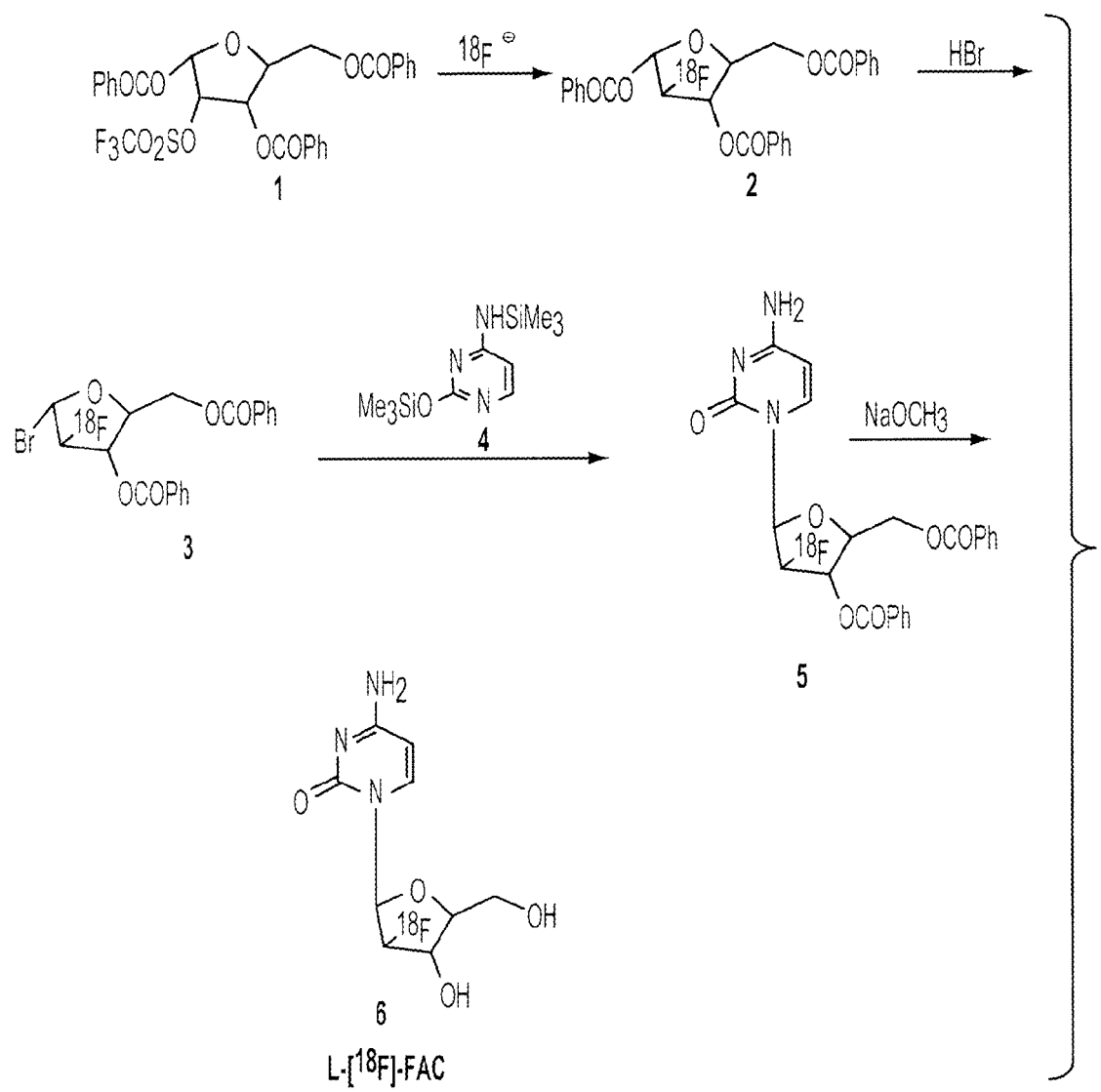
Figure 4C:
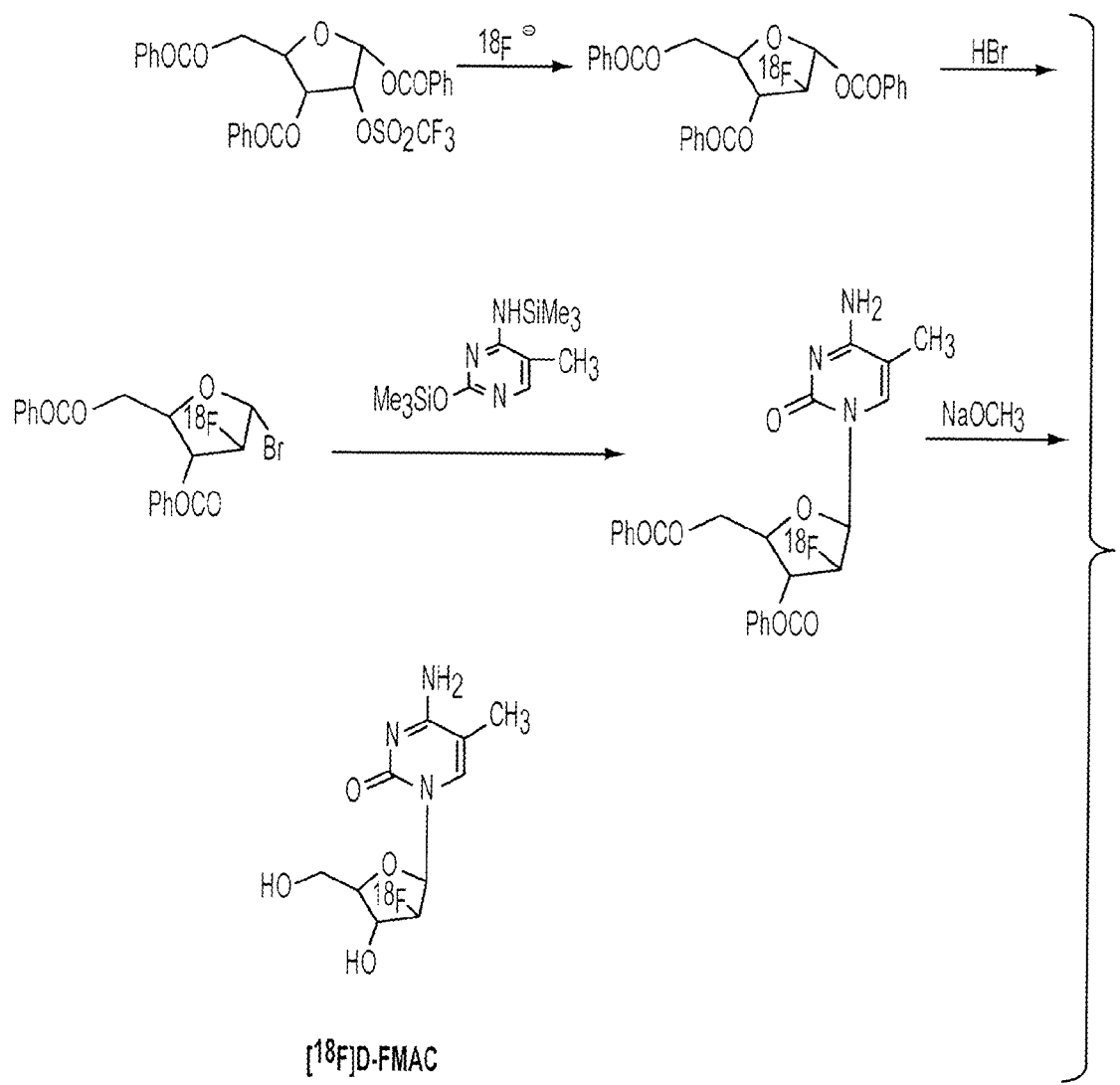
Figure 4D:
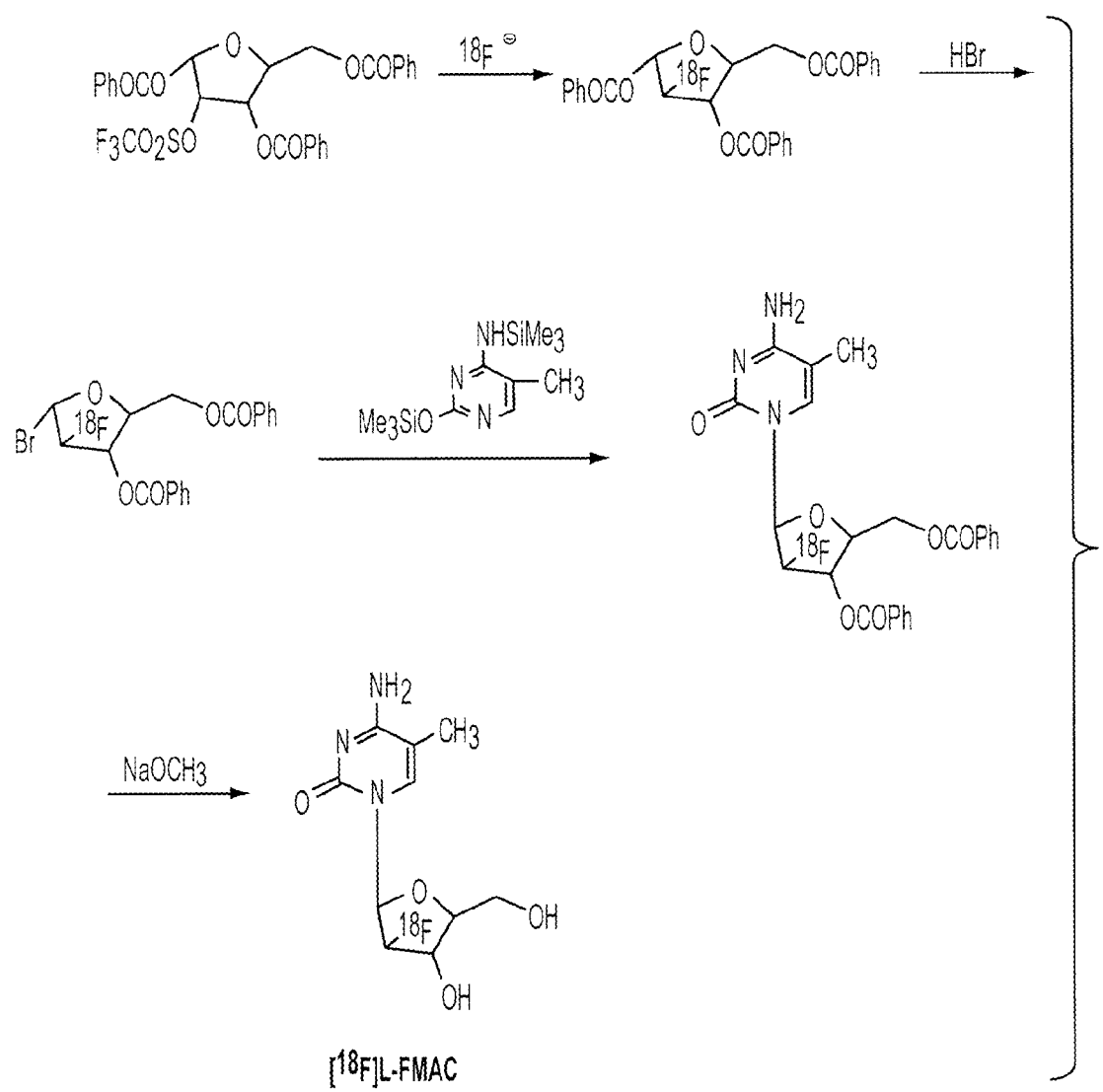
Figure 4E:
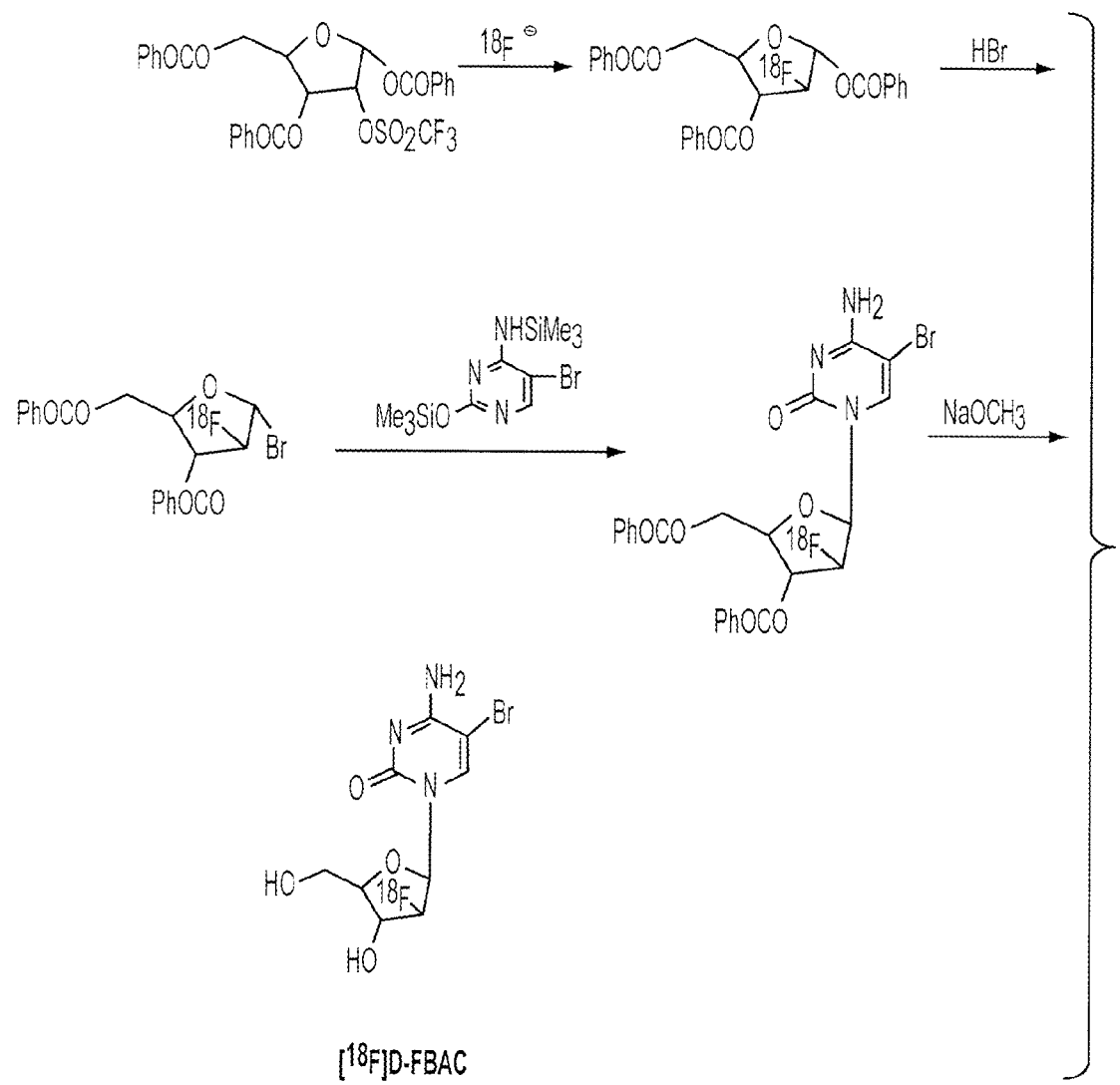
Figure 4F:
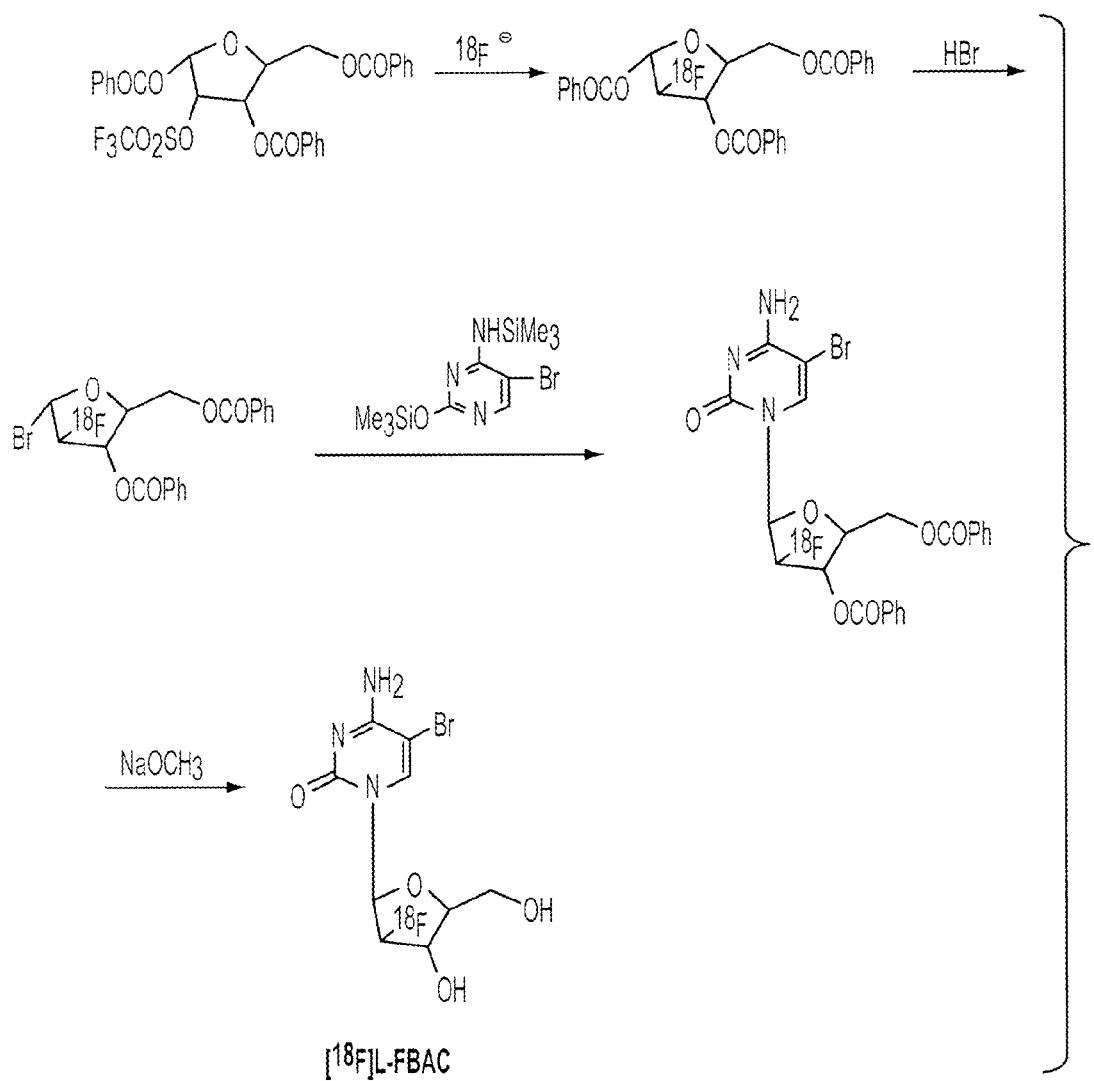
Figure 4G:
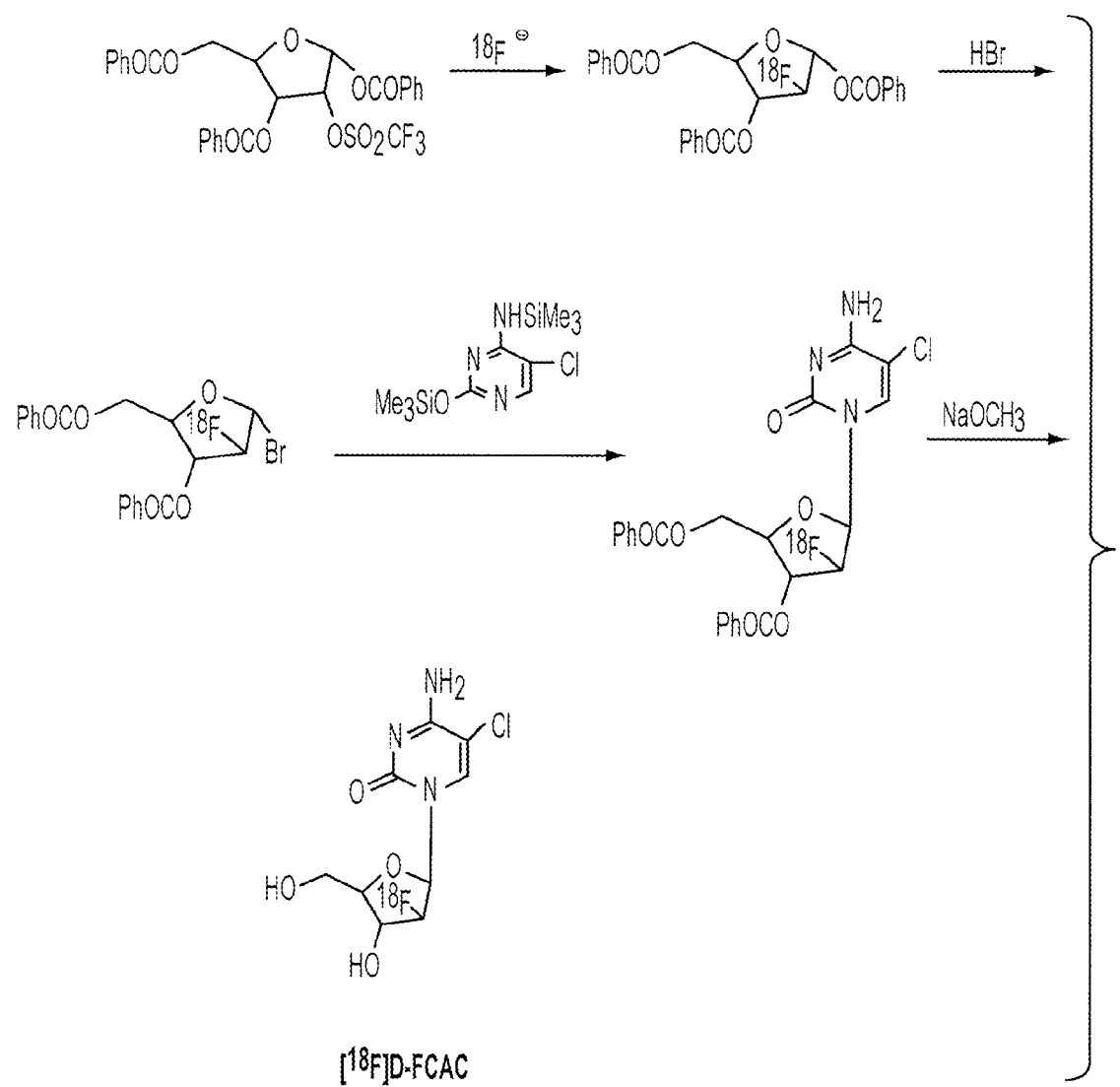
Figure 4H:
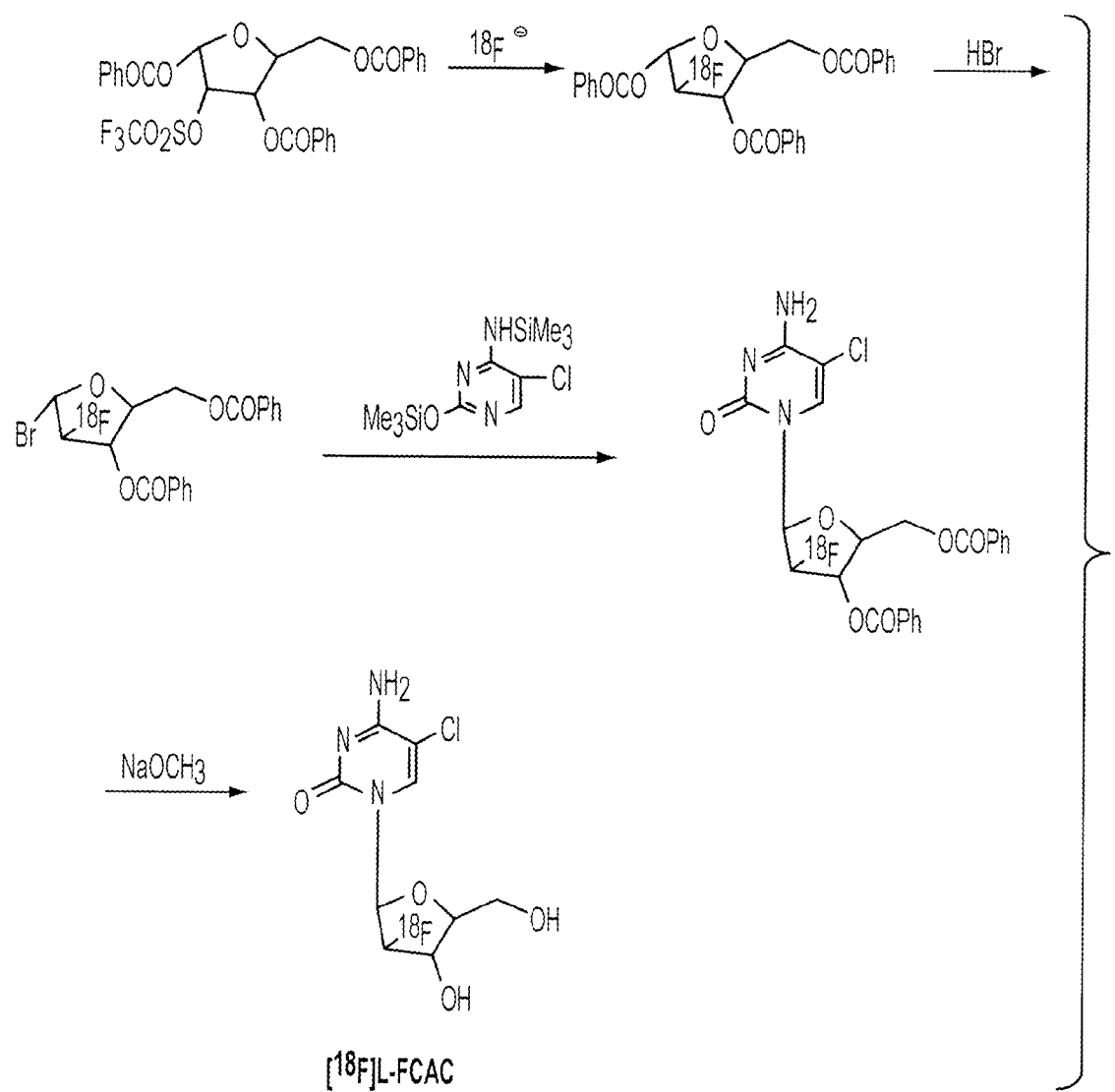
Figure 4I:
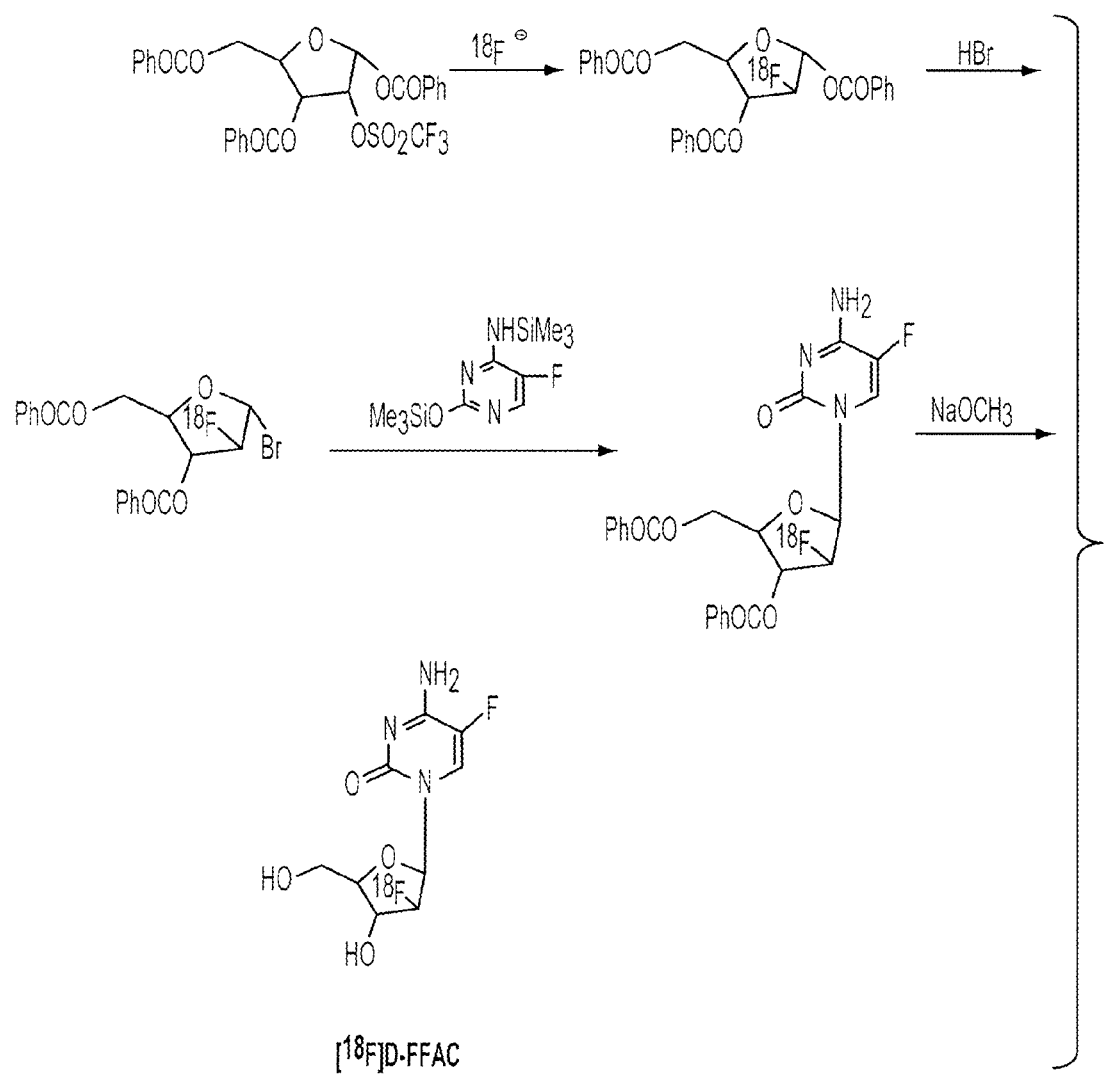
Figure 4J:
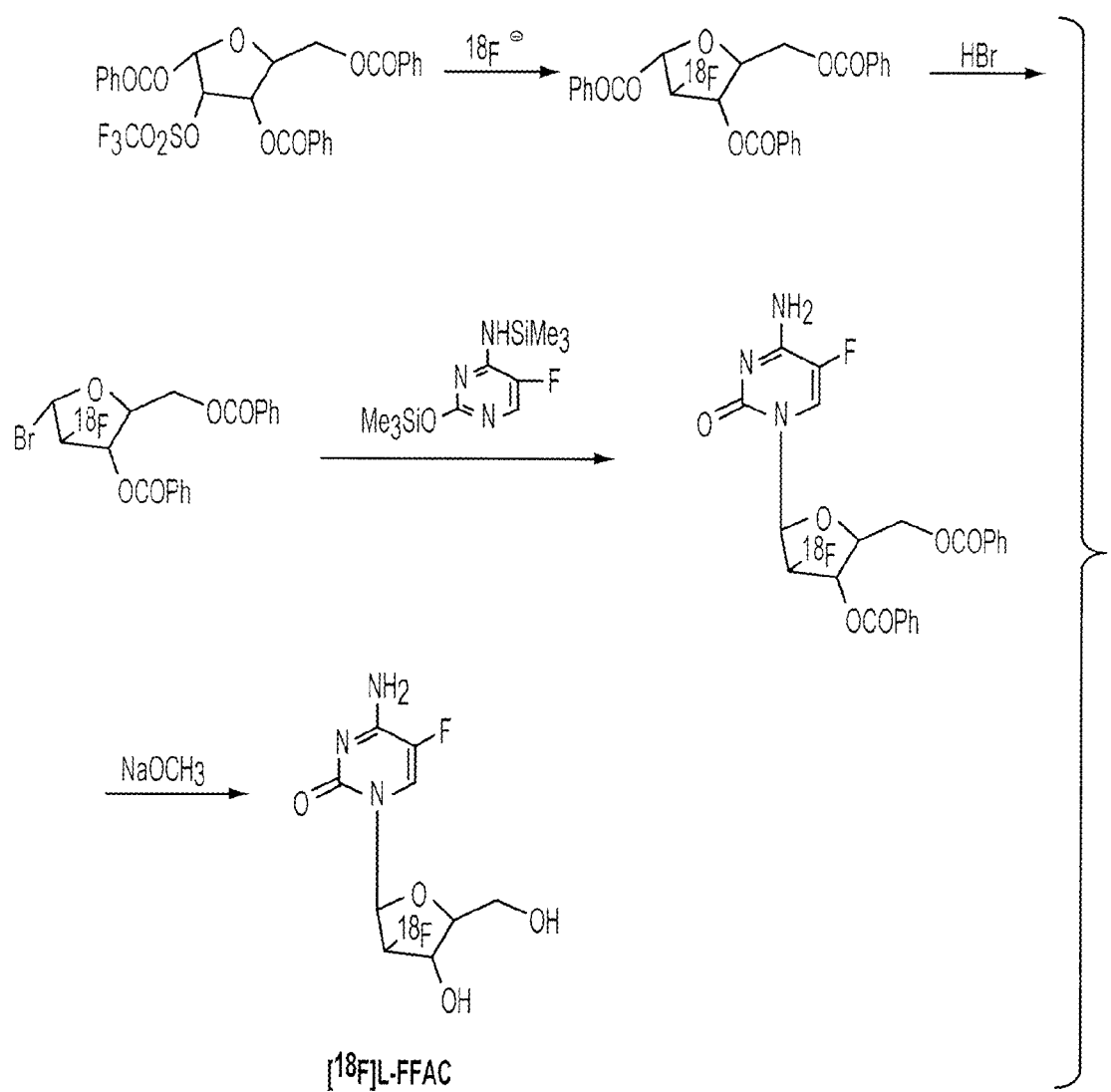

The title compound was synthesized via the reaction scheme shown above using the 2-O-[(trifluoromethyl)sulfonyl]-1,3,5-tri-O-benzoyl-α-L-ribofuranose instead of the D-isomer (1) (FIG. 4B).

Example 8

Radiochemical Synthesis of 2-chloro-9-(2'-deoxy-2'-[$^{18}$F]fluoro-β-D-arabinofuranosyl)adenine ([$^{18}$F]CA) (or D-2-$^{18}$F-CA) and 2-chloro-9-(3'-deoxy-3'-[$^{18}$F] fluoro-β-D-arabinofuranosyl)adenine (3-$^{18}$F-CA) (or D-3-$^{18}$F-CA)

The trityl protected chloroadenosine derivative mixture 2 and 3 (FIG. 4A) was prepared by a general procedure developed previously[28]. 2-chloroadenosine (1) (that is, D-2-chloroadenosine) (9.2 mmol), 4-dimethylaminopyridine (9.2 mmol), and monomethoxytrityl chloride (32.4 mmol) were placed in a dry 250 mL round bottom flask under argon and combined with 80 mL of dry pyridine. The mixture was stirred at 90° C. for 18 hr, during which time pyridine evaporated in a rotary evaporator; the last traces of the mixture were azeotropically removed with toluene. The residue was dissolved in dichloromethane and washed with water. The organic layer was dried with $Na_2SO_4$, filtered, evaporated, and the crude product was subjected to silica gel column chromatography with 25% ethyl acetate in hexane as the eluent to separate and isolate the pure hydroxy products 2 and 3. The triflates 4 and 5 were prepared from the corresponding hydroxy derivatives 2 and 3 as follows: The hydroxy compound 2 and same for compound 3 (0.1 mmol) was dissolved in 3 mL of dichloromethane under argon before addition of 4-dimethylaminopyridine (0.18 mmol) and the cooling of the solution in an ice bath at 0° C. for 10 min. Triflyl chloride (0.02 mL) was added and the reaction mixture was gradually warmed to room temperature and stirred for 3 hr; the mixture was then diluted with 10 mL of dichloromethane and washed with water, and the organic layer was dried with $Na_2SO_4$. Evaporation of dichloromethane gave an oily residue, which was purified by silica gel column chromatography using 30% ethyl acetate in hexane as eluent; this provided the pure triflate derivatives 4 and 5.

No-carrier-added [$^{18}$F]fluoride ion was produced by 11 MeV proton bombardment of 98% enriched [$^{18}$O]water in a silver target body using a RDS-112 cyclotron. The aqueous [$^{18}$F]fluoride ion was treated with a solution of $K_2CO_3$ (1 mg) and Kryptofix 2.2.2 (10 mg) dissolved in water (0.04 mL) and acetonitrile (0.75 mL) mixture. The solution was evaporated at 115° C. with a stream of nitrogen gas and the remaining residue was dried by the azeotropic distillation with acetonitrile (3×0.5 mL). The triflate precursor 4 or 5 (10 mg) was then dissolved in 1 mL of acetonitrile, which was added to the dried $K^{18}F$/Kryptofix complex and this mixture reacted at 110° C. for 25 min. The reaction mixture was cooled to room temperature and passed through a small cartridge of silica gel, which was eluted with 4×2 mL of ethyl acetate. The ethyl acetate was evaporated to dryness and the residue was then dissolved in 0.5 mL of acetonitrile. One mL of 1M HCl was added to the acetonitrile solution and heated at 100° C. for 5 min. The reaction mixture was diluted to a total volume of 3 mL with a solution of 15% ethanol with 85% 25 mM ammonium acetate in water and injected into a semi-preparative HPLC column (Phenomenex Gemini C-18 column; 25×1 cm). The resulting mixture was eluted with a mobile phase of 15% ethanol with 85% 25 mM ammonium acetate in water at a flow rate of 5.0 mL/min. The effluent from the column was monitored with a UV detector ($\lambda=263$ nm) and a gamma radioactive detector. The chemically and radiochemically pure $^{18}$F-labeled products 6 and 7 with retention times of 11-13 min were thus isolated in 10-15% radiochemical yields.

Example 8B

Radiochemical Synthesis of 2-chloro-9-(2-deoxy-2-[$^{18}$F]fluoro-β-L-arabinofuranosyl)adenine (L-2-$^{18}$F-CA) and 2-chloro-9-(3-deoxy-3-[$^{18}$F]fluoro-β-L-arabinofuranosyl)adenine (L-3-$^{18}$F-CA)

The title compounds can be synthesized via the reaction scheme shown above using L-2-chloroadenosine (the enantiomer of D-2-chloroadenosine).

Example 9

Radiochemical synthesis of [$^{18}$F]D-FRAC, [$^{18}$F]L-FRAC, [$^{18}$F]D-FMAC, [$^{18}$F]L-FMAC, [$^{18}$F]D-FXAC, [$^{18}$F]L-FXAC, [$^{18}$F]D-FBAC, [$^{18}$F]L-FBAC, [$^{18}$F]D-FCAC, [$^{18}$F]L-FCAC, [$^{18}$F]D-FFAC, [$^{18}$F]L-FFAC followed the reaction conditions described above for [$^{18}$F]D-FAC and [$^{18}$F]L-FAC using appropriately substituted silylated cytosine derivatives as shown in FIGS. 4C-J.

[$^{18}$F]D-FAC PET can be used to determine the reasons for drug resistance of tumors to oncolytic nucleoside analogs (NAs). Oncolytic drugs such as gemcitabine (Gemzar) and Ara-C are widely used to treat a variety of hematological malignancies and solid tumors. However, primary or acquired resistance to these NAs and other related prodrugs represent a significant problem to cancer treatment (Table 3). Table 3 presents prodrug nucleoside analogs that require dCK (deoxycytidine kinase) for activation and pharmacodynamic effects. Previous studies have shown that dCK deficiency is a key determinant of resistance to gemcitabine and Ara-C[19,20]. Furthermore, clinical studies have also reported a significant correlation between dCK expression in pancreatic cancer patients and their response to gemcitabine treatment; specifically, patients with tumors expressing low levels of dCK had a decreased survival time compared to those with tumors expressing high levels of dCK[21,22]. Although resistance to gemcitabine and Ara-C is usually acquired over the course of treatment via selection of drug resistant clones, there have been reports of polymorphisms in the dCK gene that confer inherent (primary) resistance to gemcitabine[25,26]. Drug resistance of tumors has also been linked to decreased expression of nucleoside transporters (e.g., SLC29A1/ENT1) and deoxycytidine kinase (dCK); also, the upregulation of cytidine deaminase (CDA), cytidylate deaminase (DCTD), 5' nucleotidases, and ribonucleoside reductase have caused drug resistance (see review[23]). From these mechanisms, [$^{18}$F] D-FAC and its analogs may be used to estimate gemcitabine and Ara-C resistance via decreased expression of nucleoside transporters and/or dCK. We focused on the latter mechanism since dCK represents the rate-limiting step of pro-drug activation[24].

TABLE 3

| Drug | Structure | Indications |
| --- | --- | --- |
| Cytosine arabinoside (Ara-C) | 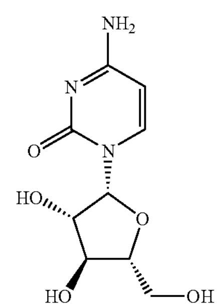 | Acute non-lymphocytic leukemia, acute lymphocytic leukemia and the blast phase of chronic myelocytic leukemia, prophylaxis and treatment of meningeal leukemia |
| Gemcitabine (Gemzar; Lilly) | 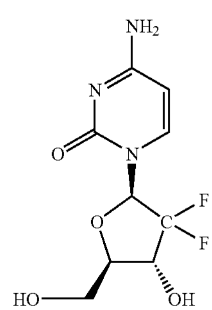 | Pancreatic, ovarian, breast, and non-small cell lung cancers |

TABLE 3-continued

| Drug | Structure | Indications |
|---|---|---|
| Fludarabine (Fludara; Berlex) | 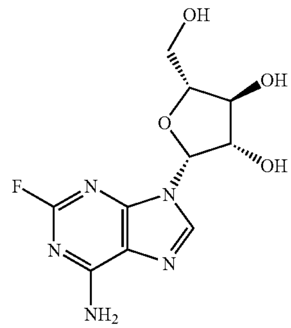 | B-cell chronic lymphocytic leukemia (CLL) |
| Cladribine (Leustatin; R.W. Johnson) | 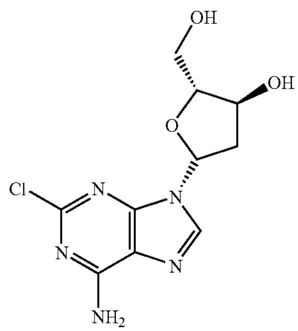 | Hairy cell leukemia |
| Clofarabine (Evoltra ®/Clolar; Bioenvision, Genzyme) | 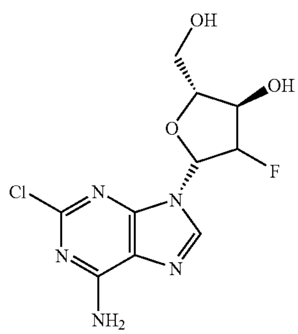 | Relapsed or refractory acute lymphoblastic leukemia after at least two prior regimens |

Example 10

Figure 13:
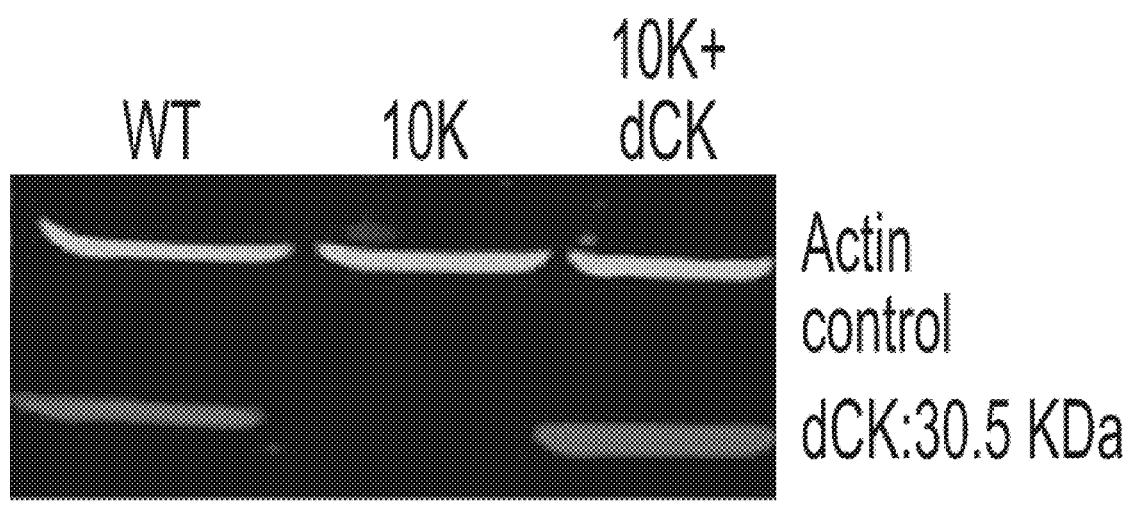
FIG. 13 is a Western blot demonstrating the expression of deoxycytidine kinase (dCK) in the L1210 cell lines. The L1210 cell lines were probed with anti-total dCK antibody.
Figure 14A:
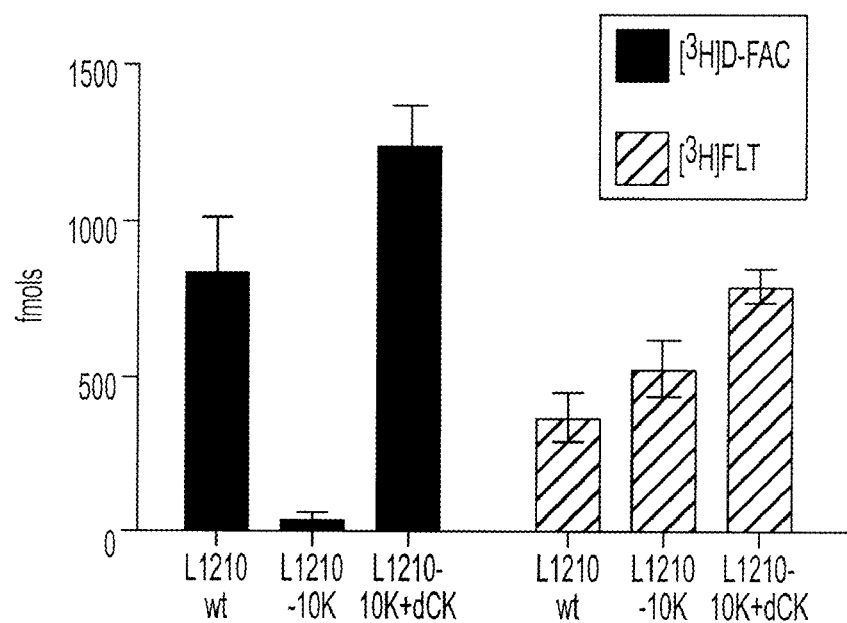
FIG. 14A shows the retention of [$^3$H]D-FAC and [$^3$H]FLT probes in L1210, L1210-10K, and L1210-10K with reintroduced dCK cell lines.
Figure 14B:
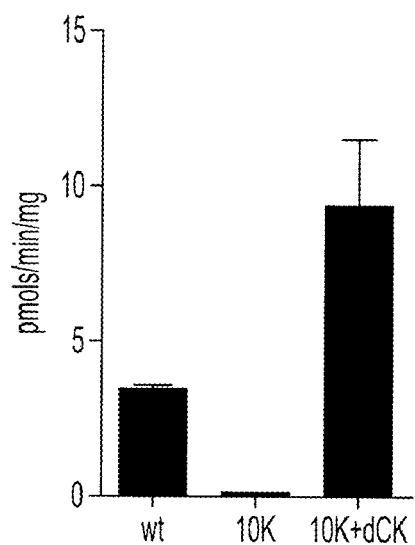
FIG. 14B shows D-FAC phosphorylation in the cell lines.

Use of [$^{18}$F]D-FAC PET to Determine Resistance to Oncolytic Nucleoside Analogs To evaluate whether [$^{18}$F]D-FAC PET can determine resistance to gemcitabine and Ara-C, we used a previously described experimental model based on the L1210 murine leukemia cells and their gemcitabine/Ara-C resistant 10K derivatives[20]. The molecular defect responsible for resistance in the L1210 10K cells is loss of dCK expression due to a genetic modification of chromosome 5 in the 3' region of the dCK gene. The 10K cell line was derived by exposing the parental L1210 cells to increasing concentrations of gemcitabine[20]; before experiments, we confirmed that L1210 10K cells lack expression of dCK at the protein level (FIG. 13). Thus, to determine whether D-FAC retention correlates with gemcitabine resistance in these cells, we performed radioactive tracer uptake assays using [$^3$H]D-FAC with [$^3$H]-FLT used as a negative control. We observed that the gemcitabine-resistant L1210-10K cell line retained much lower amounts of [$^3$H]D-FAC in contrast to the gemcitabine-sensitive L1210 parental cell line (FIG. 14A). In fact, [$^3$H]D-FAC uptake was 40-fold higher in dCK$^+$ cells compared to cells lacking dCK activity (dCK$^+$=1288 fmols/1×10$^5$ cells; dCK-=34 fmols/1× 10$^5$ cells; p<0.001). In contrast, [$^3$H]FLT uptake was indistinguishable between these cell lines. FIG. 14B presents a [$^3$H]D-FAC kinase assay with the L1210 cell lines using [$^3$H]D-FAC as a substrate (1 microgram protein/reaction). In dCK positive cells shown in FIG. 14B, D-FAC phosphorylation was 52-fold higher than in dCK deficient cells (dCK$^+$=62 fmols; dCK$^-$=1.2 fmols; p=0.028). Reintroduction of dCK into the L1210-10K cells restored [$^{18}$F]D-FAC uptake and phosphorylation (FIG. 14), thus further confirming the critical role of this nucleoside kinase in regulating D-FAC metabolism.

Figure 15A:
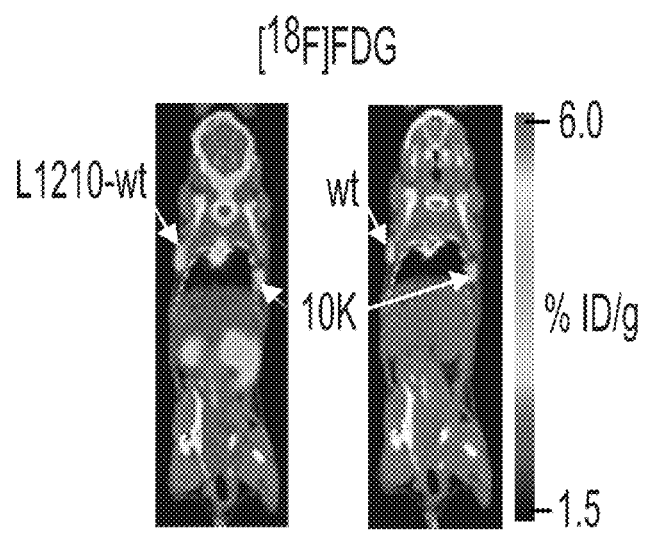
FIG. 15A shows accumulation of [$^{18}$F]FDG.
Figure 15B:
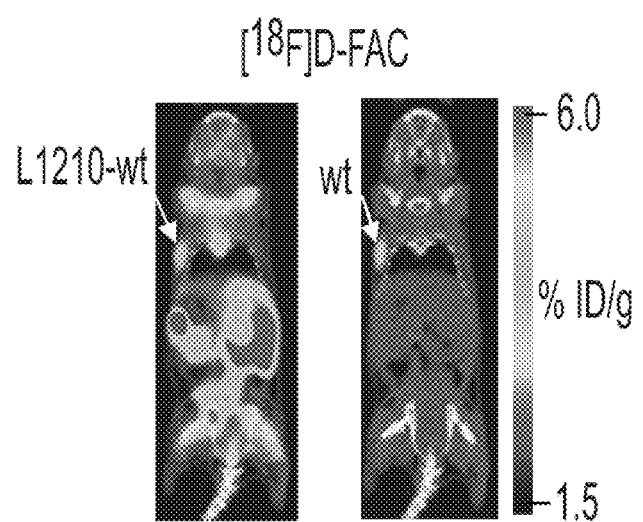
FIG. 15B shows accumulation of [$^{18}$F]D-FAC.

To investigate whether [$^{18}$F]D-FAC PET can distinguish gemcitabine-sensitive cancer cells from the resistant cancer cells in vivo, mice were injected with L1210 wild type or 10K cells to establish subcutaneous tumors; mice were scanned with [$^{18}$F]FDG PET to confirm that implanted cells were viable and growing in vivo and [$^{18}$F]D-FAC PET scans were carried out to compare D-FAC accumulation in gemcitabine sensitive versus resistant cells. Both gemcitabine sensitive and resistant cells showed equivalent FDG accumulation (FIG. 15A). In contrast, the retention of [$^{18}$F]D-FAC was clearly detectable in dCK positive tumors whereas this probe did not accumulate in dCK deficient tumors (FIG. 15B). These data indicate that [$^{18}$F]D-FAC PET measurements of dCK activity in tumors can be used to predict resistance to gemcitabine and related prodrugs; i.e., [$^{18}$F]D-FAC PET/CT scans can distinguish gemcitabine sensitive and resistant tumors in vivo. In each of the panels A and B of FIG. 15, the left image shows SCID mice injected subcutaneously with L1210 WT, and the right image shows SCID mice injected subcutaneously with L1210-10K. The mice were injected 4 days prior to imaging.

Example 11

Preliminary Evaluation of [$^{18}$F]D-FAC in Humans

Figure 16:
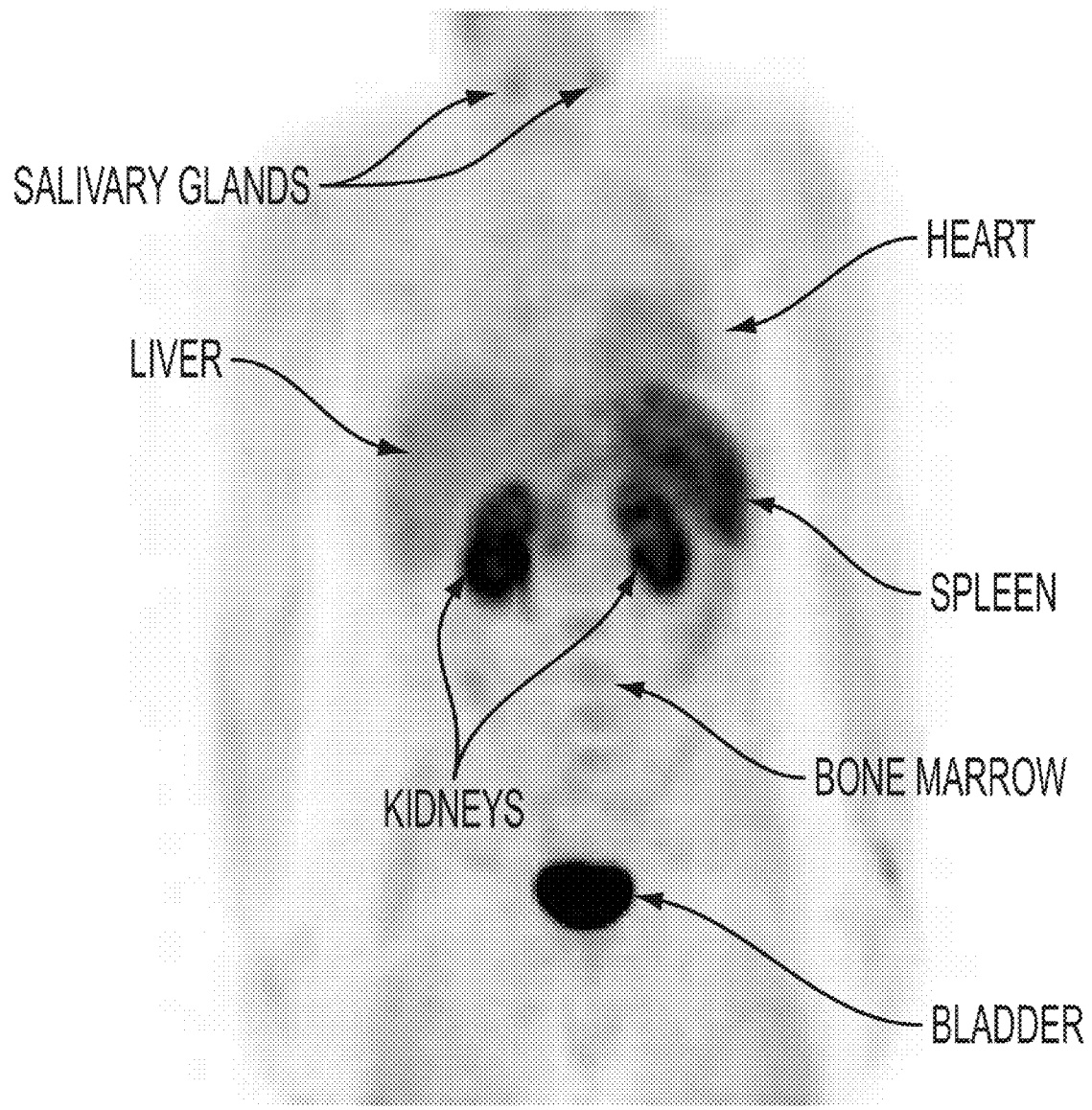
FIG. 16 shows the biodistribution of [$^{18}$F]D-FAC in a healthy human volunteer via a coronal microPET scan 48 minutes after injection of the [$^{18}$F]D-FAC.

[$^{18}$F]D-FAC was evaluated in humans to a preliminary degree, whereby we investigated the normal biodistribution and radiation dosimetry of [$^{18}$F]D-FAC in human subjects (FIG. 16). Biodistribution data were obtained from attenuation-corrected whole-body PET scans of 3 healthy male subjects after a bolus injection of [$^{18}$F]D-FAC (8.6±2.3 mCi). Emission scans were acquired 20, 48, and 76 min post injection and radiation dosimetry estimates were calculated using the Olinda® software. The organs with the highest accumulation of [$^{18}$F]D-FAC were the bladder, the kidneys, the spleen, the salivary glands, and the heart. The organs receiving the highest absorbed doses were the urinary bladder wall (2.06E-01 rem/mCi), followed by the kidneys (1.06E-01 rem/mCi), spleen (7.36E-02 rem/mCi), osteogenic cells (6.69E-02 rem/mCi), the heart wall (5.92E-02 rem/mCi), and the small intestine (5.80E-02 rem/mCi) with the effective dose overall being 5.08E-02 rem/mCi. The radiation dosimetry estimates show high agreement with the dosimetry results obtained from the studies in mice. The dose-limiting organs were the urinary bladder wall and the kidneys. The human [$^{18}$F]D-FAC scan shown in FIG. 16 resembles certain aspects of the [$^{18}$F]D-FAC images acquired in mice, namely that the probe accumulates in the spleen and to a lesser extent in the bone marrow of spinal column. However, in contrast to mice, the retention of [$^{18}$F]D-FAC in the GI tract is substantially lower in humans.

Example 12

Development and Evaluation of Novel dCK $^{18}$F-labeled Substrates with Improved In Vivo Stability and Specificity The development and evaluation of novel dCK $^{18}$F-labeled substrates with improved in vivo stability and specificity was undertaken. Deamination-resistant deoxycytidine kinase (dCK) substrates as potential PET imaging probes are shown in FIGS. 2A and 4.

Although in mice the susceptibility of D-FAC to deamination does not affect its utility for imaging immune activation and cancer, deamination-resistant D-FAC analogs are needed. Deamination-resistant dCK substrates may have several advantages over D-FAC, including improved specificity, sensitivity, and in vivo stability. We thus synthesized and evaluated potential probes to measure dCK activity by PET (FIGS. 2A and 4). For example, [$^{18}$F]L-FAC is a novel non-natural analog of D-FAC developed based on the differential enantioselectivity of dCK and CDA towards D- and L-nucleosides (note that while dCK phosphorylates both natural D-enantiomers and non-natural L-enantiomers, CDA has a strict requirement for D-deoxycytidine analogs). [$^{18}$F]-CA (FIGS. 2A and 4) is a purine dCK substrate resistant to deamination by adenosine deaminase.

Figure 17A:
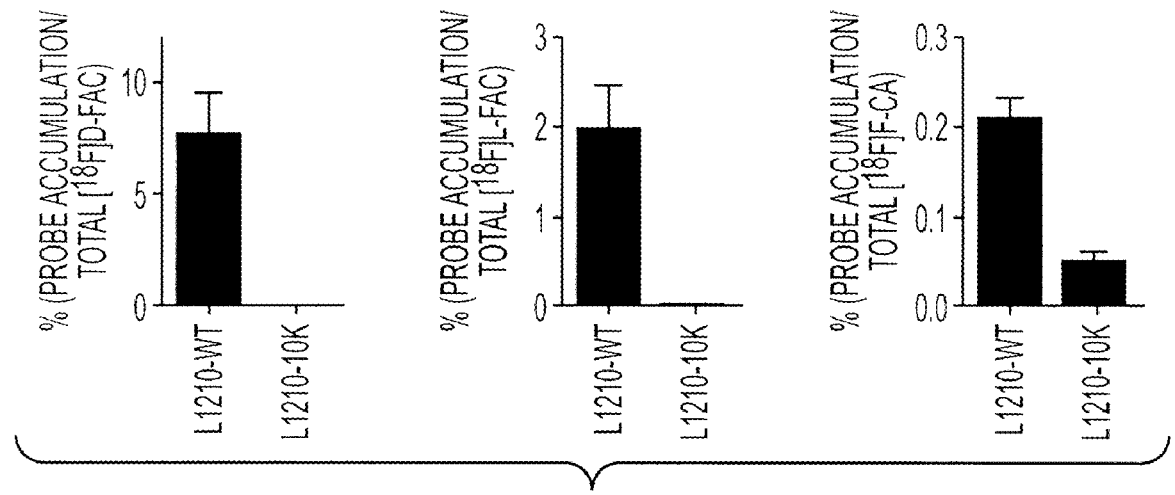
FIG. 17A shows the accumulation of [$^{18}$F]D-FAC, [$^{18}$F]L-FAC, and [$^{18}$F]-CA probes in L1210-WT and L1210-10K cell lines.
Figure 17B:
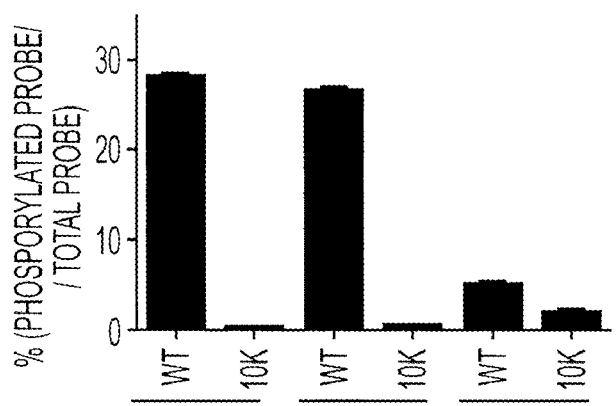
FIG. 17B shows the extent of phsophorylation of probes in L1210-WT and L1210-10K cell lysates.
Figure 18A:
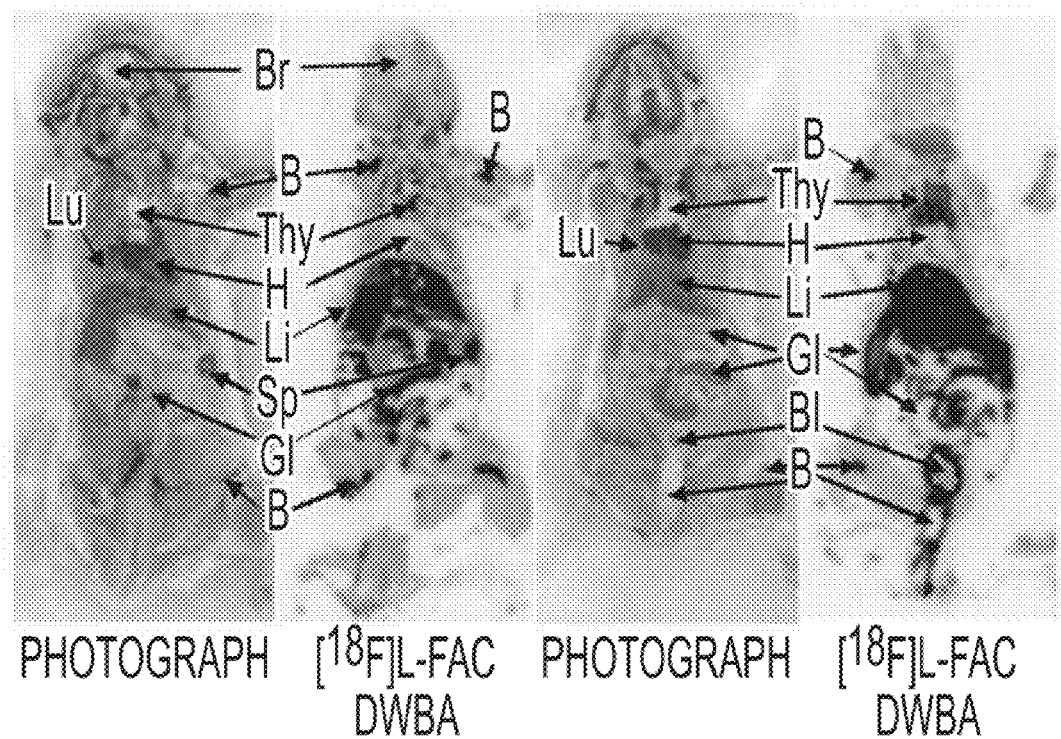
FIG. 18A shows images obtained with [$^{18}$F]L-FAC.
Figure 18B:
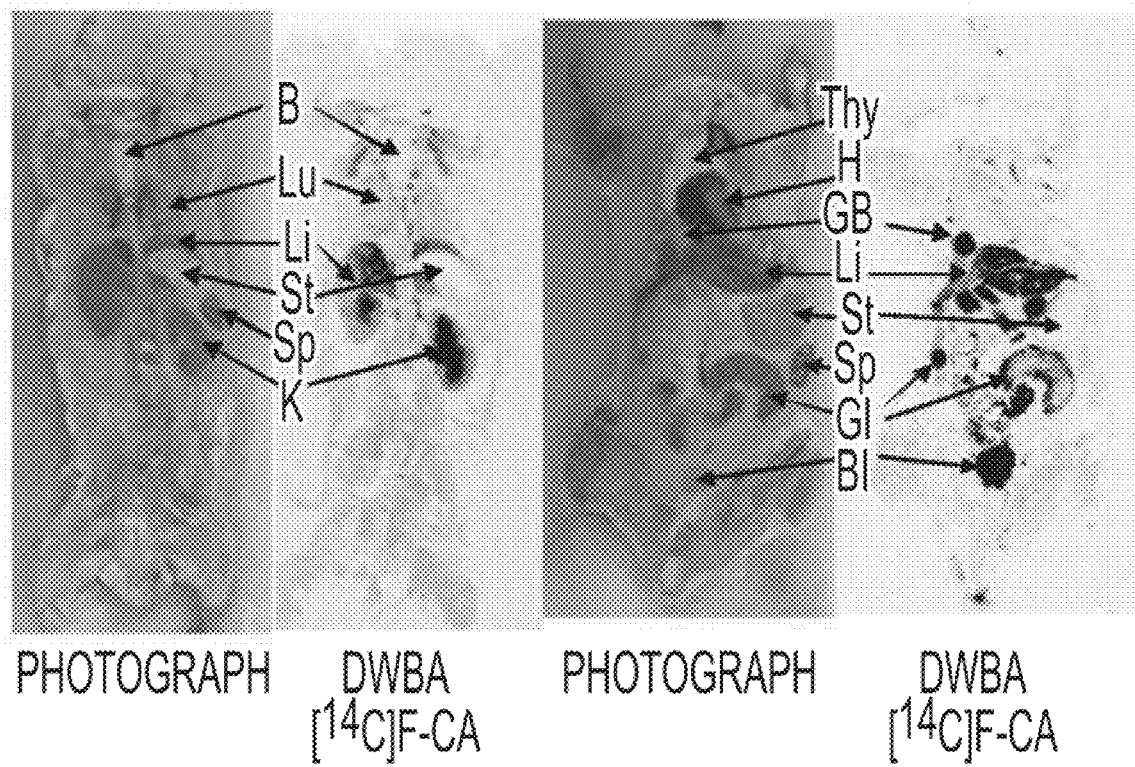
FIG. 18B shows a [$^{14}$C] F-CA DWBA.
Figure 18C:
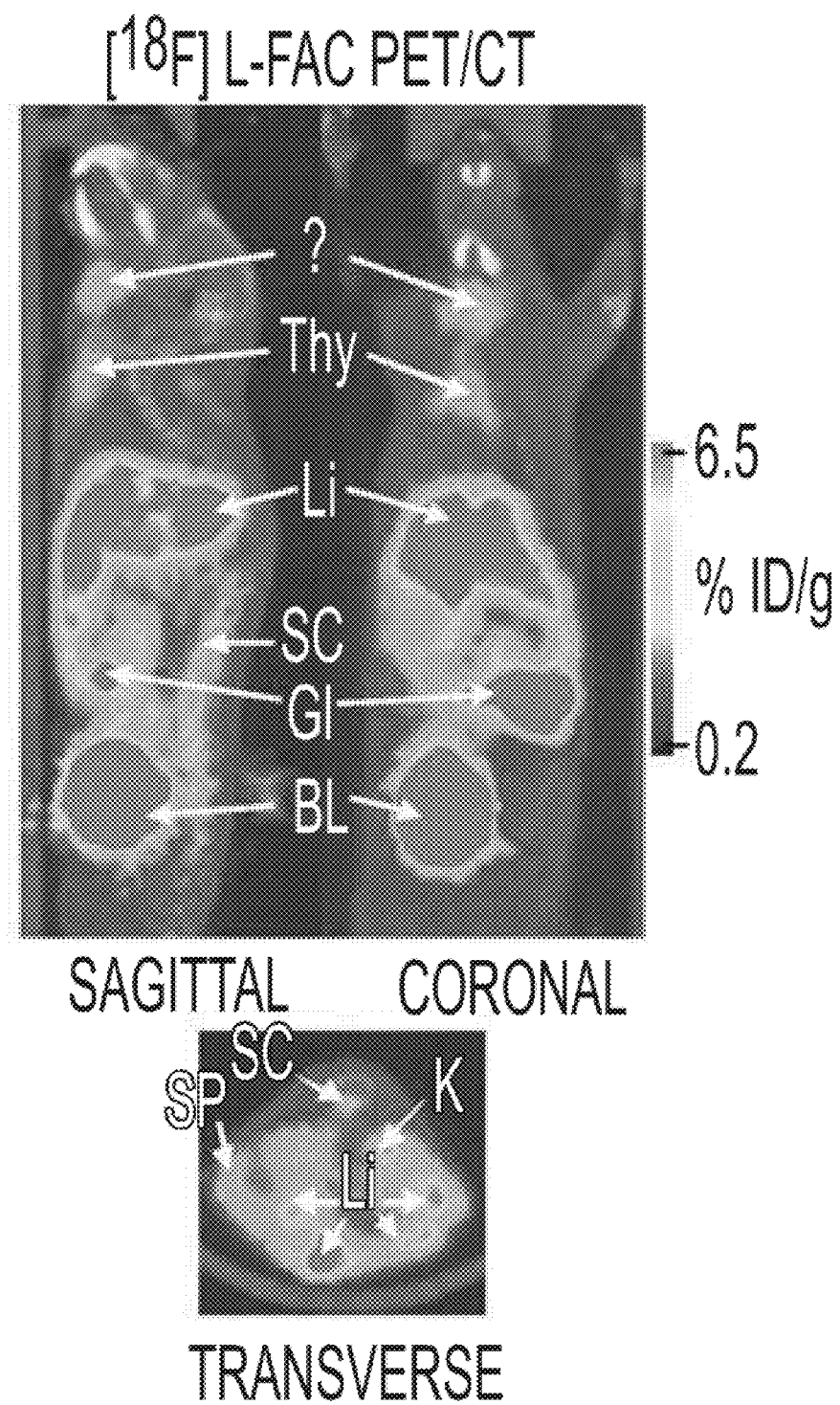
FIG. 18C shows images obtained with [$^{18}$F] L-FAC and microPET/CT.
Figure 18D:
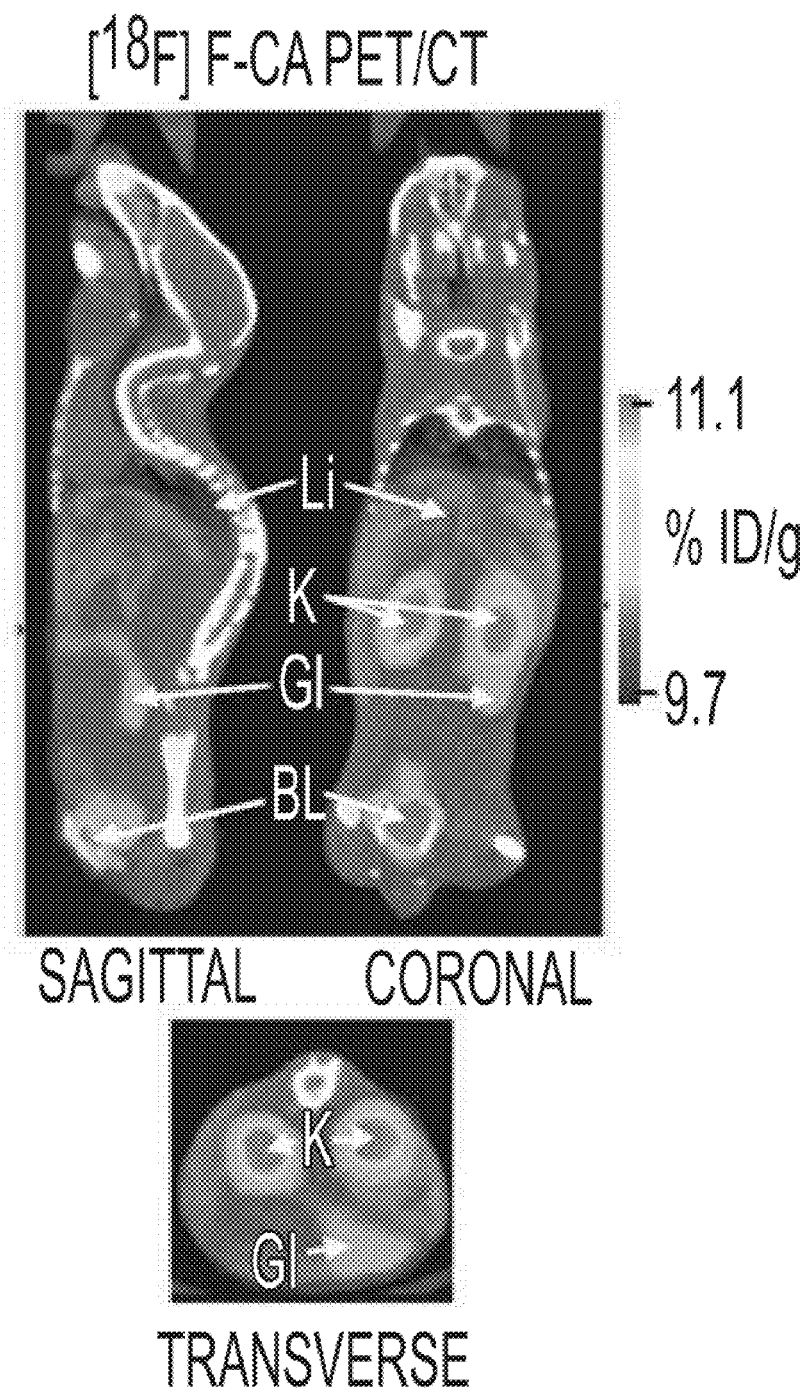
FIG. 18D shows images obtained with [$^{18}$F]F-CA and microPET/CT.
Figure 19A:
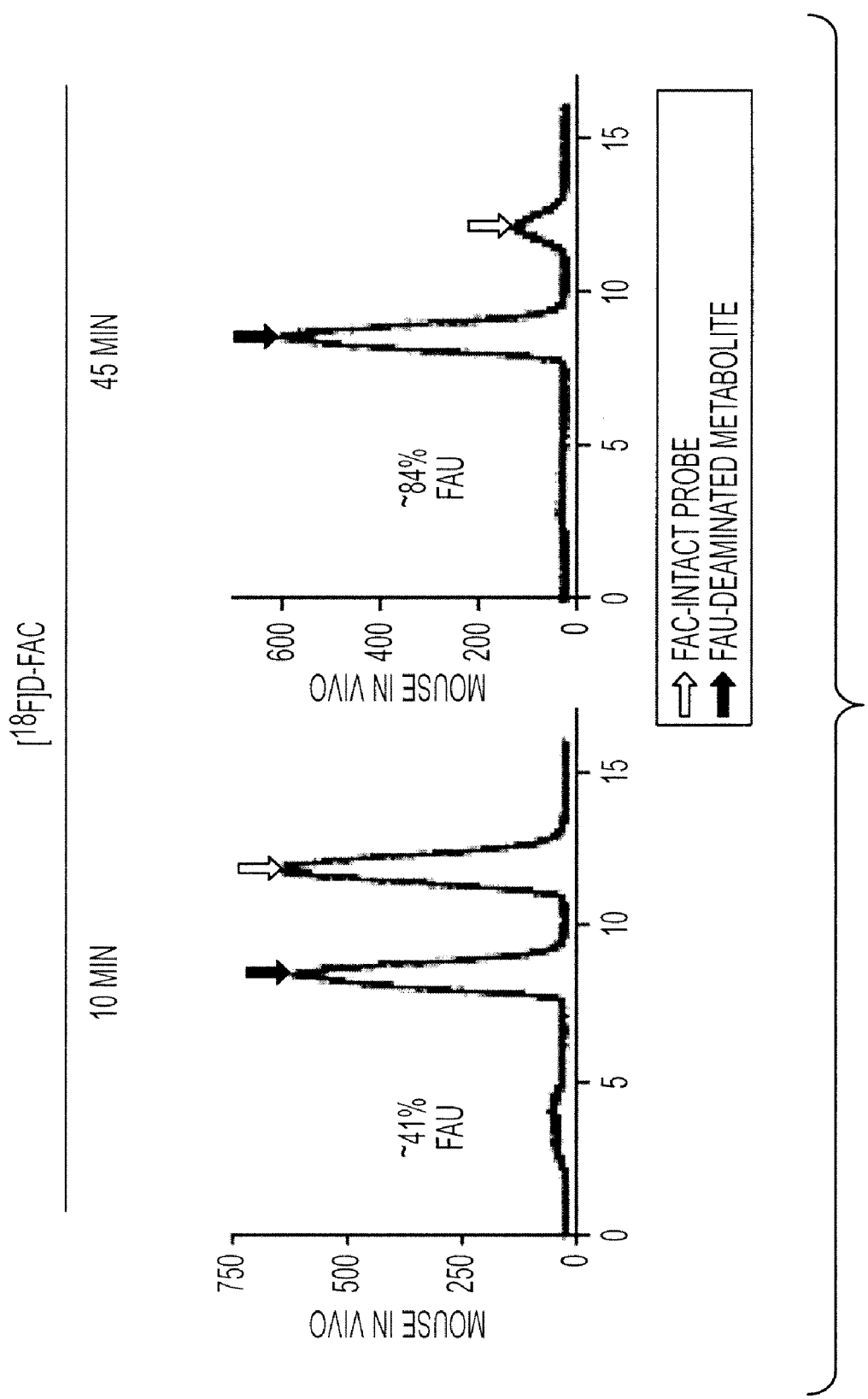
FIGS. 19A and 19B show chromatographs of [$^{18}$F]D-FAC and [$^{18}$F]L-FAC in plasma at 10 minutes and 45 minutes following injection into a mouse.
Figure 19B:
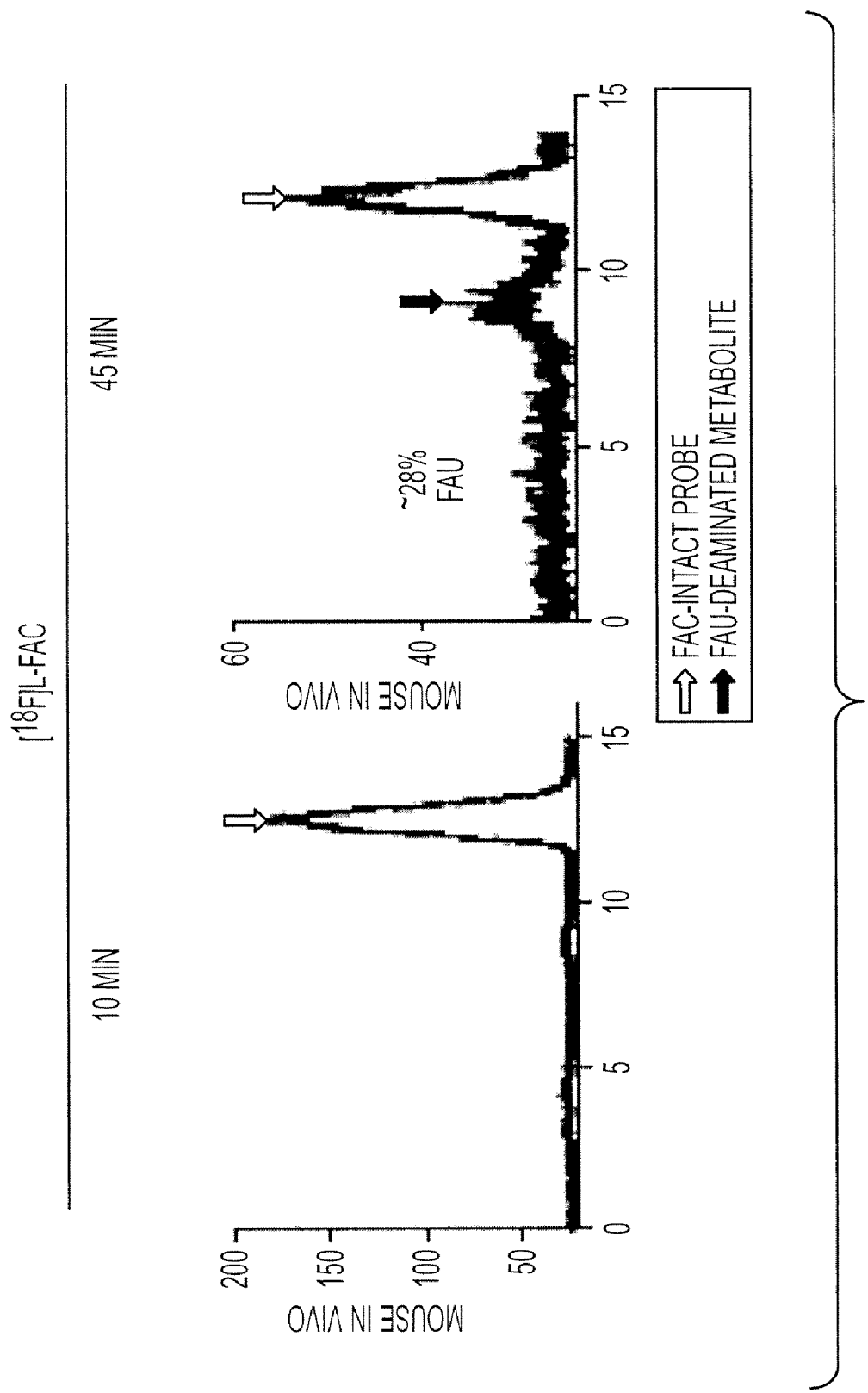
Figure 19C:
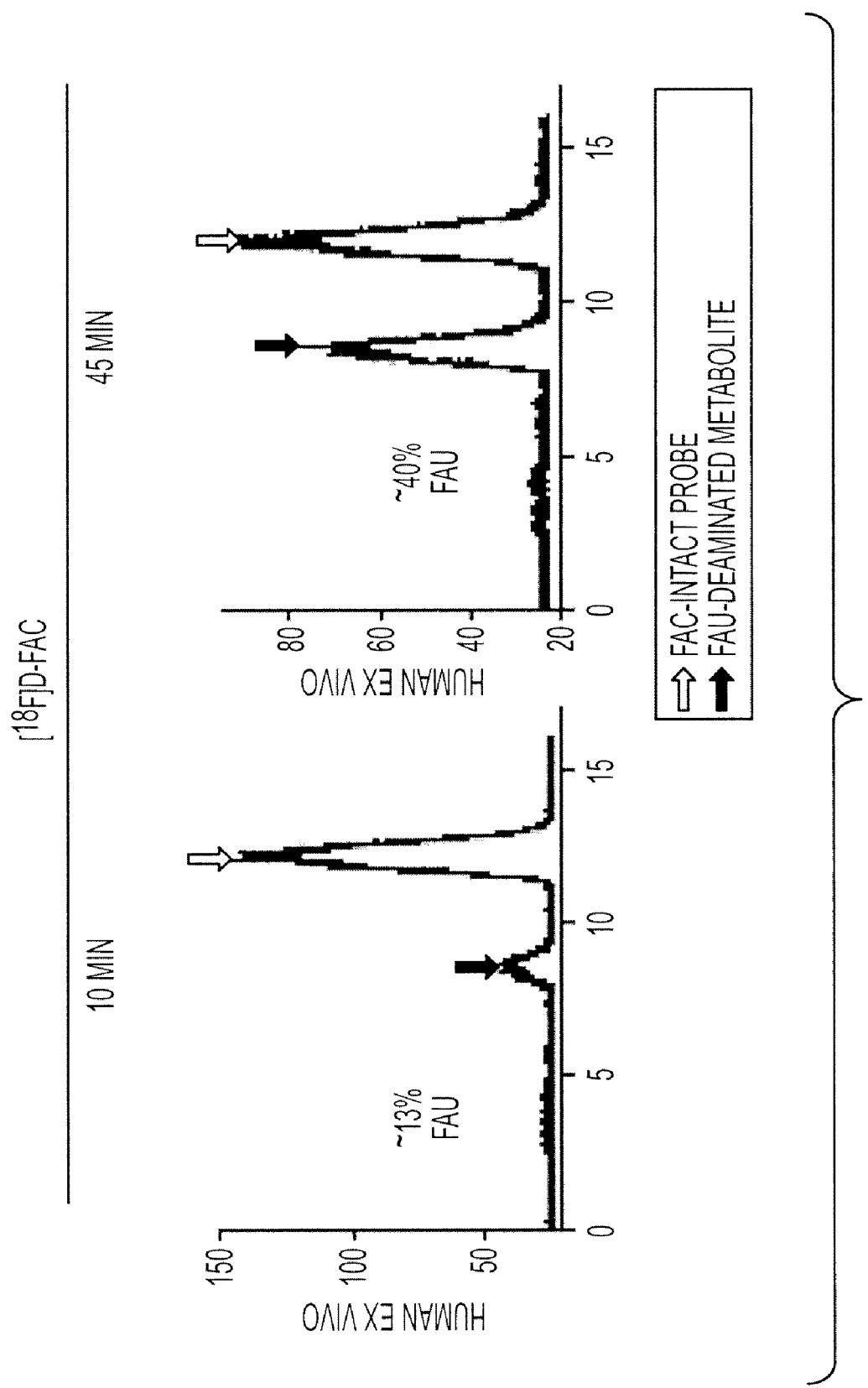
FIGS. 19C and 19D show chromatographs of [$^{18}$F]D-FAC and [$^{18}$F]L-FAC in plasma at 10 minutes and 45 minutes after the probe was incubated with human plasma.
Figure 19D:
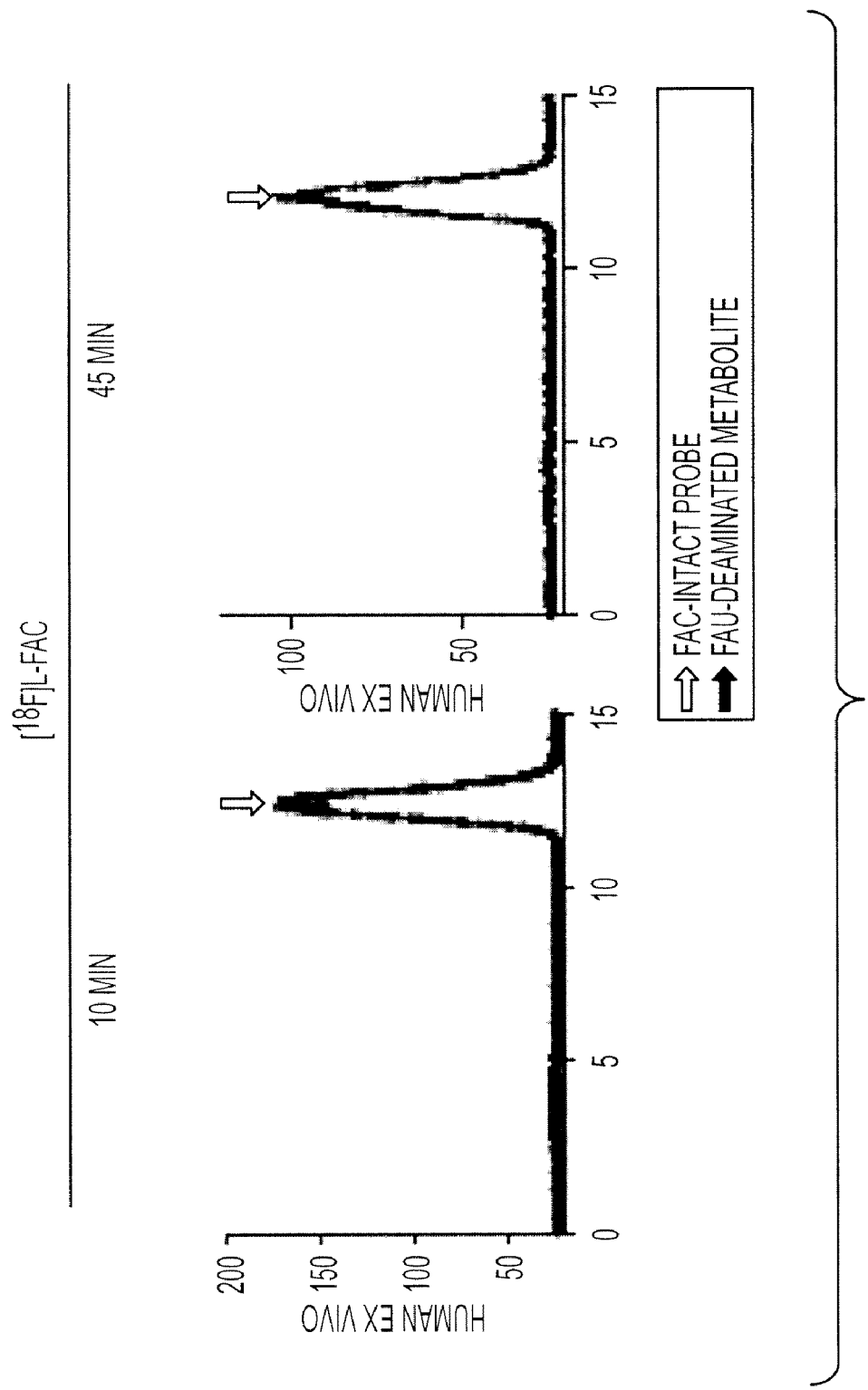

The observation that the intracellular accumulation of [$^{18}$F]-CA and [$^{18}$F]L-FAC requires the expression of dCK is demonstrated in FIG. 17 utilizing the L1210 wild type cells and the 10K dCK deficient cells. Each cell type was incubated separately with each of the following: [$^{18}$F]L-FAC, and [$^{18}$F]-CA, and the positive control [$^{18}$F]D-FAC. The cells were incubated with [$^{18}$F]L-FAC, [$^{18}$F]-CA, and [$^{18}$F]D-FAC for 1 hour. Following successive washes, intracellular radioactivity was measured by scintillation counting to obtain the result shown in FIG. 17A. By measuring intracellular radioactivity, it was determined that retention and phosphorylation of [$^{18}$F] L-FAC and [$^{18}$F]-CA requires dCK expression. FIG. 17B shows results obtained from incubation of L1210 WT and 10K cell lysates with $^{18}$F]L-FAC, [$^{18}$F]-CA, and [$^{18}$F]D-FAC; phosphorylated products were measured by scintillation counting.

PET images show biodistribution studies of [$^{18}$F]L-FAC and [$^{18}$F]-CA in mice (FIG. 18). FIG. 18A presents images obtained with [$^{18}$F]L-FAC. FIG. 18B presents a [$^{14}$C]F-CA DWBA with corresponding tissue sections. C57/BL6 mice were scanned by microPET/CT using [$^{18}$F]L-FAC (FIG. 18C) and [$^{18}$F]F-CA (FIG. 18D). Mice were imaged 60 minutes after intravenous injection of probes. Images are 1 mm thick sagittal, coronal, and transverse slices. Percent ID/g is the percent injected dose per gram of tissue. The labels are as follows: B, Bone Marrow/Bone; BL, Bladder; BR, Brain; GB, Gall Bladder; GI, Gastrointestinal tract; H, heart; K, kidney; L, Liver; LU, Lung; SP, Spleen; Thy, Thymus; ST, Stomach. The results of FIG. 18 demonstrate that the biodistribution of [$^{18}$F]L-FAC resembles that of [$^{18}$F]D-FAC. In contrast, [$^{18}$F]-CA did not accumulate in thymus and spleen; the [$^{18}$F]L-FAC compound was thus further evaluated in C57/BL6 mice that were injected with the probes.

Figure 20:
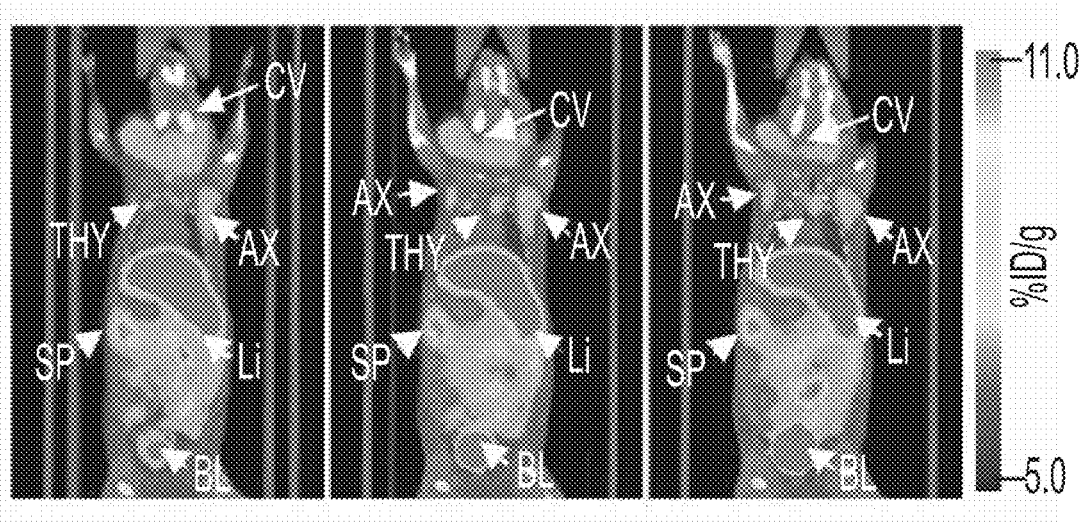
FIG. 20 shows [$^{18}$F]L-FAC microPET images of lymphadenopathy in an animal model of systemic autoimmunity.
Figure 21:
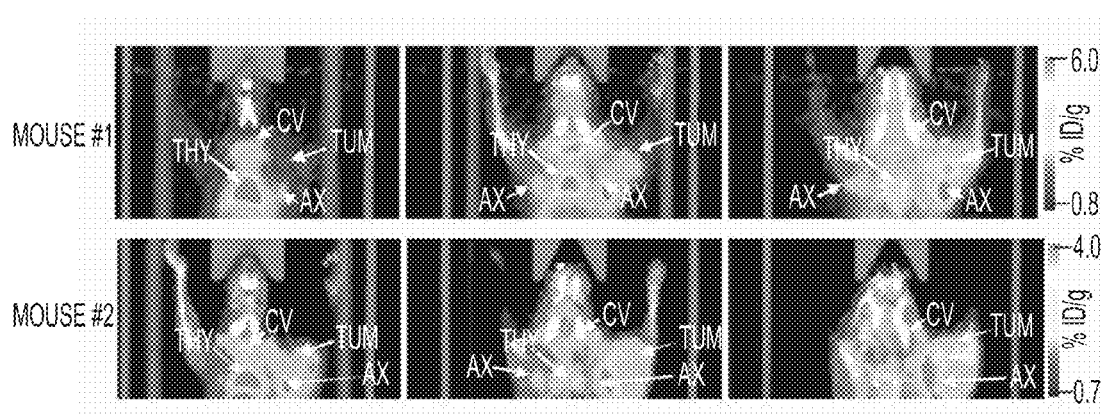
FIG. 21 shows [$^{18}$F]L-FAC microPET images of immune activation during a primary T cell mediated anti-tumor immune response.
Figure 22A:
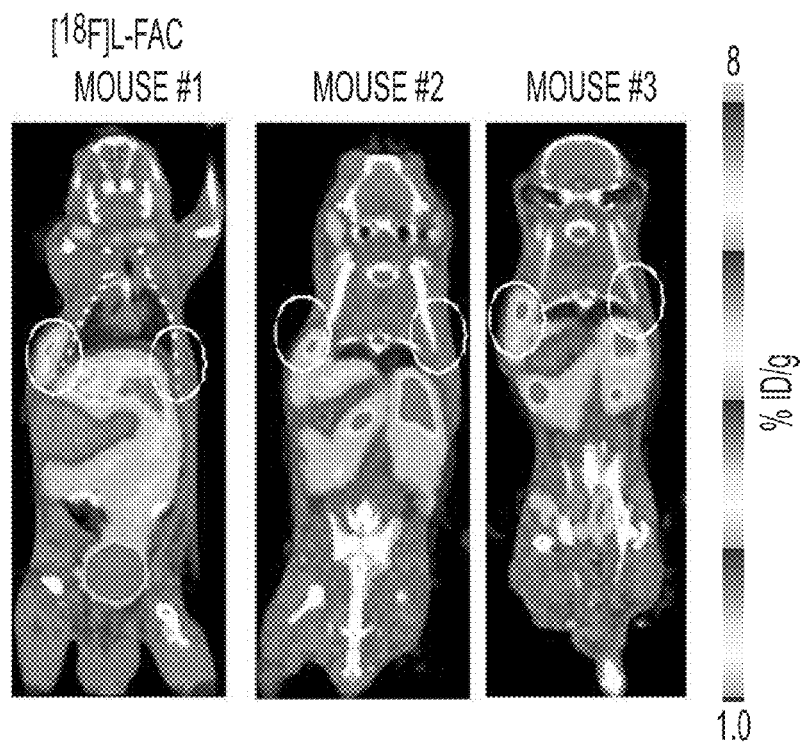
FIG. 22A shows [$^{18}$F]L-FAC microPET/CT scans.
Figure 22B:
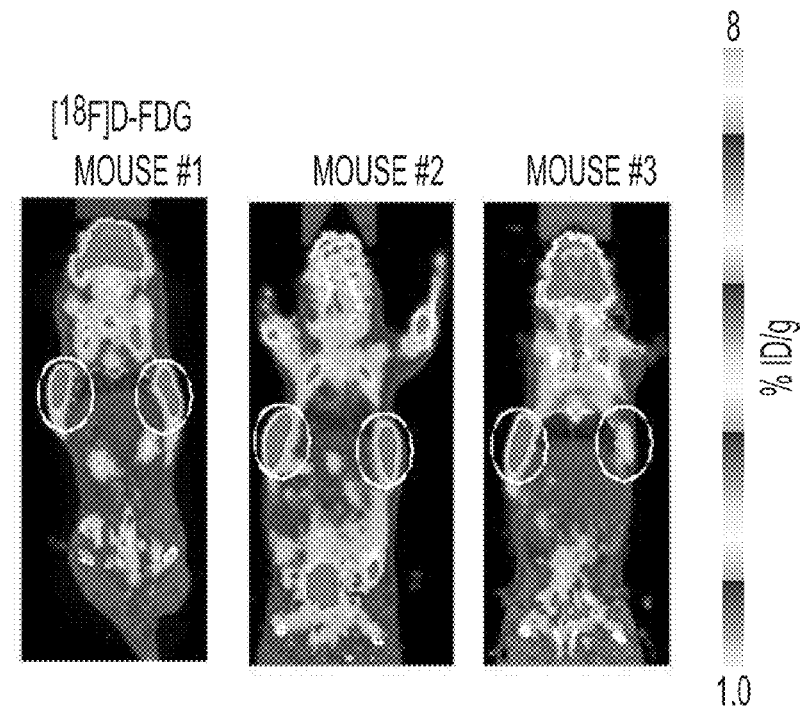
FIG. 22B shows [$^{18}$F]FDG microPET/CT scans.

The chromatograph in FIG. 19 indicates that [$^{18}$F]L-FAC is more resistant to deamination than [$^{18}$F]D-FAC. FIG. 19 presents chromatographs of [$^{18}$F]D-FAC (FIG. 19A) and [$^{18}$F] L-FAC (FIG. 19B) in plasma at 10 minutes and 45 minutes following intravenous injection of the probe into a C57BL/6 mouse. FIG. 19 presents chromatographs of [$^{18}$F]D-FAC (FIG. 19C) and [$^{18}$F]L-FAC (FIG. 19D) in plasma 10 minutes and 45 minutes after the probe was incubated with human plasma. In vivo studies in mice and data using human plasma show that [$^{18}$F]L-FAC has improved stability relative to [$^{18}$F] D-FAC. In FIG. 20, the microPET/CT image uses [$^{18}$F]L-FAC to show lymphadenopathy in an animal model with systemic autoimmunity. That is increased lymphoid mass in systemic autoimmunity is shown. The images are 60 minutes after intravenous injection of [$^{18}$F]L-FAC and show three 1 mm thick coronal slices from mice. The labels are as follow: Thy, Thymus; LN, Lymph Nodes; BM, Bone-Marrow/Bone. Mice carrying the Fas$^{1pr}$ mutation develop lymphadenopathy, arthritis and immune complex-mediated glomerulonephrosis[29] due to defects in apoptosis of T and B lymphocytes. To evaluate the ability of [$^{18}$F]L-FAC PET to monitor an autoimmune phenotype, we used Fas$^{1pr}$ mice on the C57BL/6J genetic background. [$^{18}$F]L-FAC PET imaging of immune activation during a primary T cell-mediated anti-tumor immune response is shown in FIG. 21 (the oncoretrovirus model of anti-tumor T cell-mediated immunity was utilized[30]). FIG. 21 shows PET/CT images of localized immune activation in the MSV anti-tumor immunity model. Mice were challenged with the MoMSV onco-retrovirus. Images are 60 minutes after intravenous injection of [$^{18}$F]L-FAC and show three 1 mm thick coronal slices from mice at the peak of immune response. The labels are as follow: B, Bone Marrow/Bone; BL, Bladder; GI, Gastrointestinal tract; H, Heart; SP, Spleen; TU, Tumor; LN, Lymph Node. FIG. 22 shows that [$^{18}$F]L-FAC microPET/CT can be used to visualize leukemia cells that are dCK positive and thus predict gemcitabine resistance in vivo in a SCID mouse model. That is, [$^{18}$F]L-FAC microPET/CT allows visualization of dCK positive, gemcitabine sensitive L1210 leukemia cells, but not visualization of the dCK negative, gemcitabine negative L1210 10K subline. SCID mice were injected subcutaneously with L1210 WT (left) and L1210-10K (right) cells 4 days prior to imaging. FIG. 22A shows [$^{18}$F]L-FAC microPET/CT scans; and FIG. 22B shows [$^{18}$F]FDG microPET/CT scans.

Figure 23:
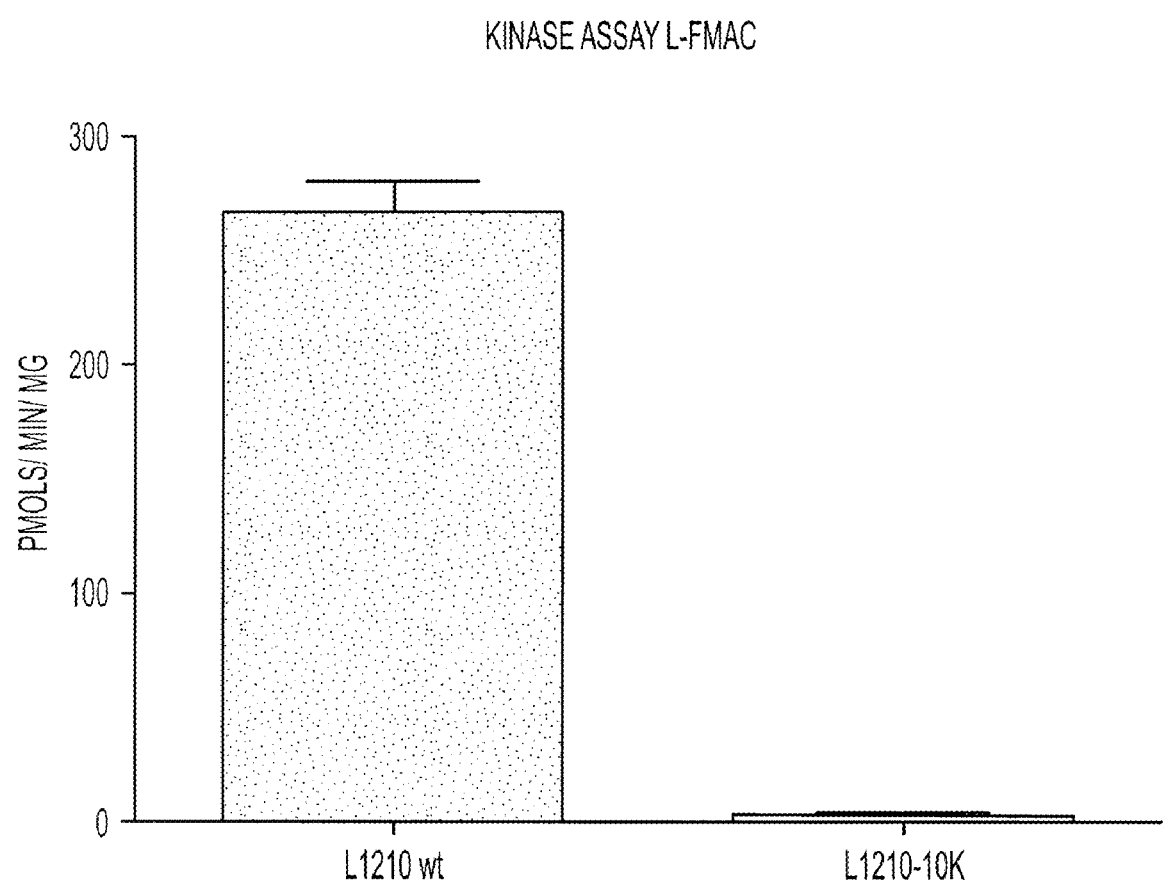
FIG. 23 illustrates that the intracellular accumulation of [$^{18}$F]L-FMAC requires the expression of deoxycytidine kinase.
Figure 24A:
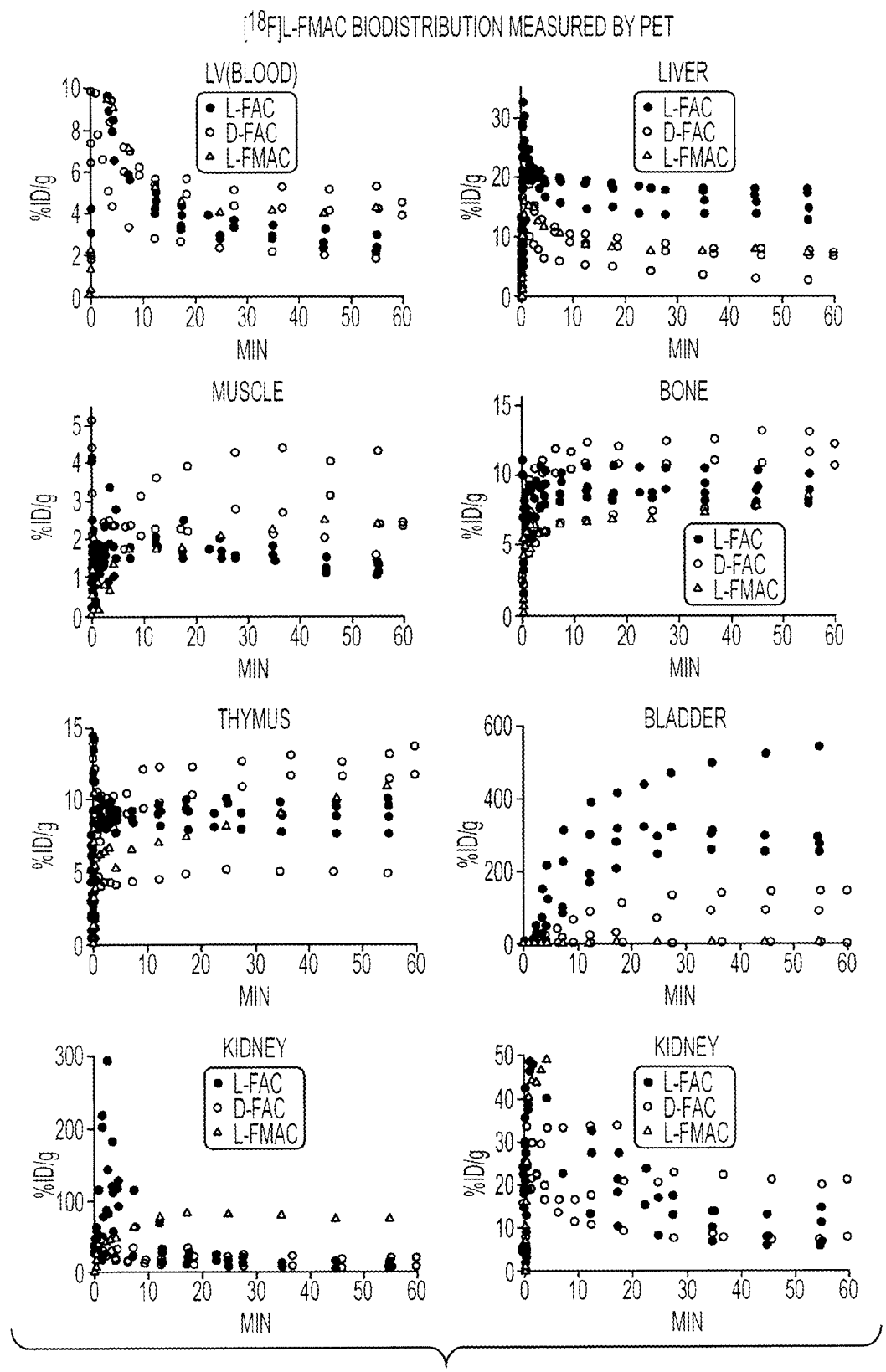
FIG. 24A shows the results of biodistribution studies of L-FAC, D-FAC, and L-FMAC.
Figure 24B:
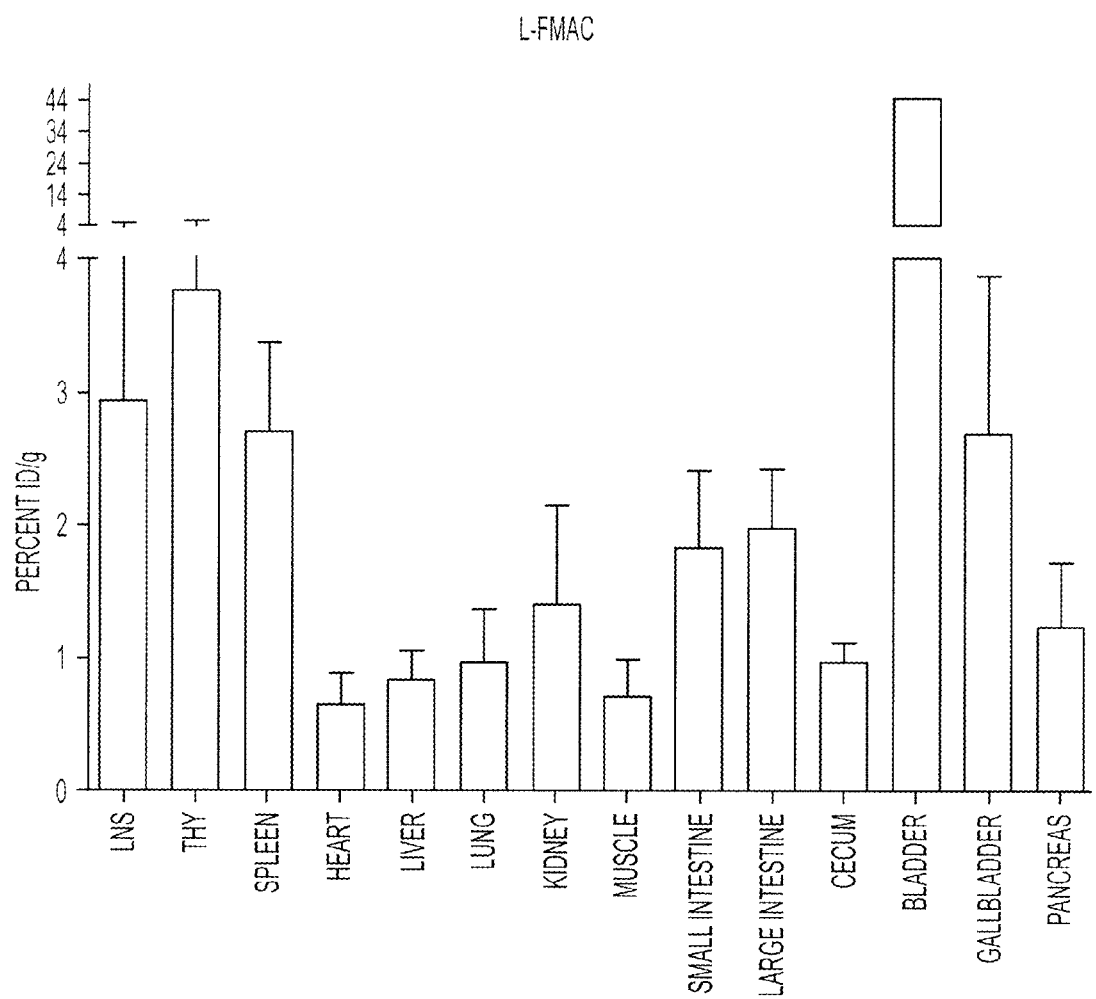
FIG. 24B shows biodistribution [$^{18}$F]L-FMAC in necropsy samples.
Figure 25A:
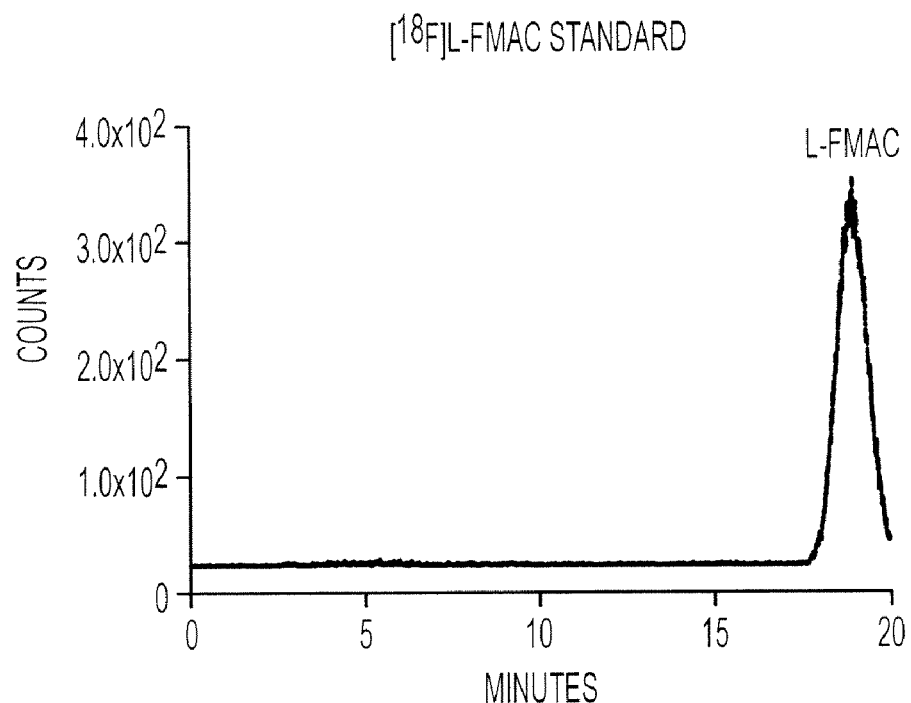
FIG. 25A shows results obtained with the [$^{18}$F]L-FMAC standard.
Figure 25B:
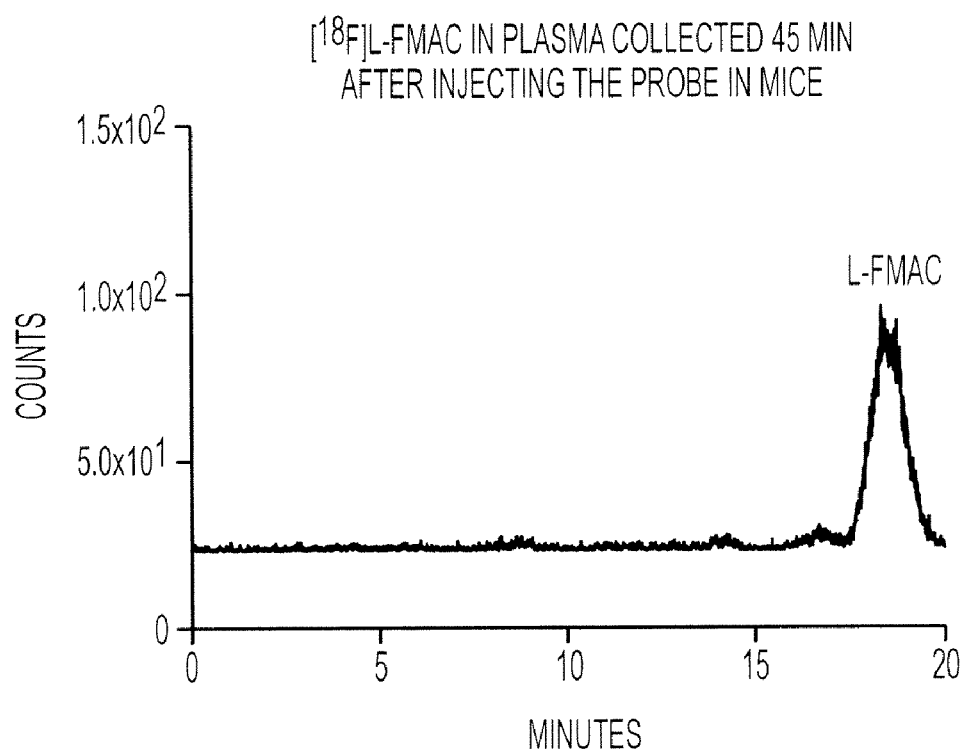
FIG. 25B shows results for [$^{18}$F]L-FMAC in plasma collected 45 minutes after injection.

FIGS. 23-28 demonstrate similar findings as above for [$^{18}$F]L-FMAC. FIG. 23 shows that retention and phosphorylation of [$^{18}$F]L-FMAC requires dCK expression. Lysates from L1210 wildtype (WT) and dCK deficient (10K) cells were incubated for 20 minutes with [$^{18}$F]L-FMAC; phosphorylated products were measured by scintillation counting. FIG. 24A shows the biodistribution of [$^{18}$F]L-FMAC from PET measurements; FIG. 24B shows the biodistribution of [$^{18}$F]L-FMAC from necroscopy data. FIG. 25 shows that [$^{18}$F]L-FMAC is resistant to deamination in mice. FIG. 25A shows results obtained with the [$^{18}$F]L-FMAC standard; and FIG. 25B shows results for [$^{18}$F]L-FMAC in plasma collected 45 minutes after injecting the probe into mice.

Figure 26A:
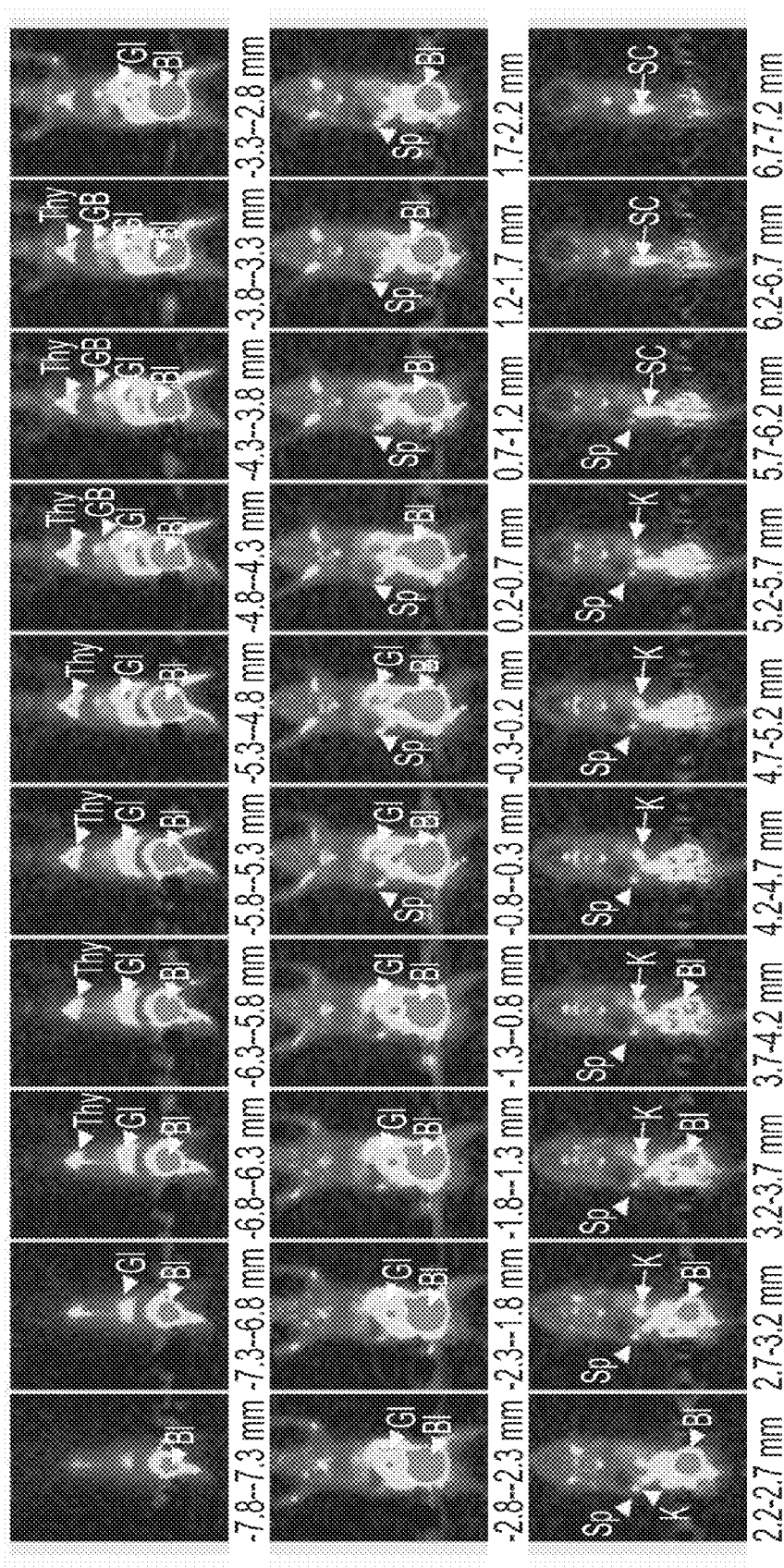
FIG. 26A shows results obtained with the wild type BL/6 mouse.
Figure 26B:
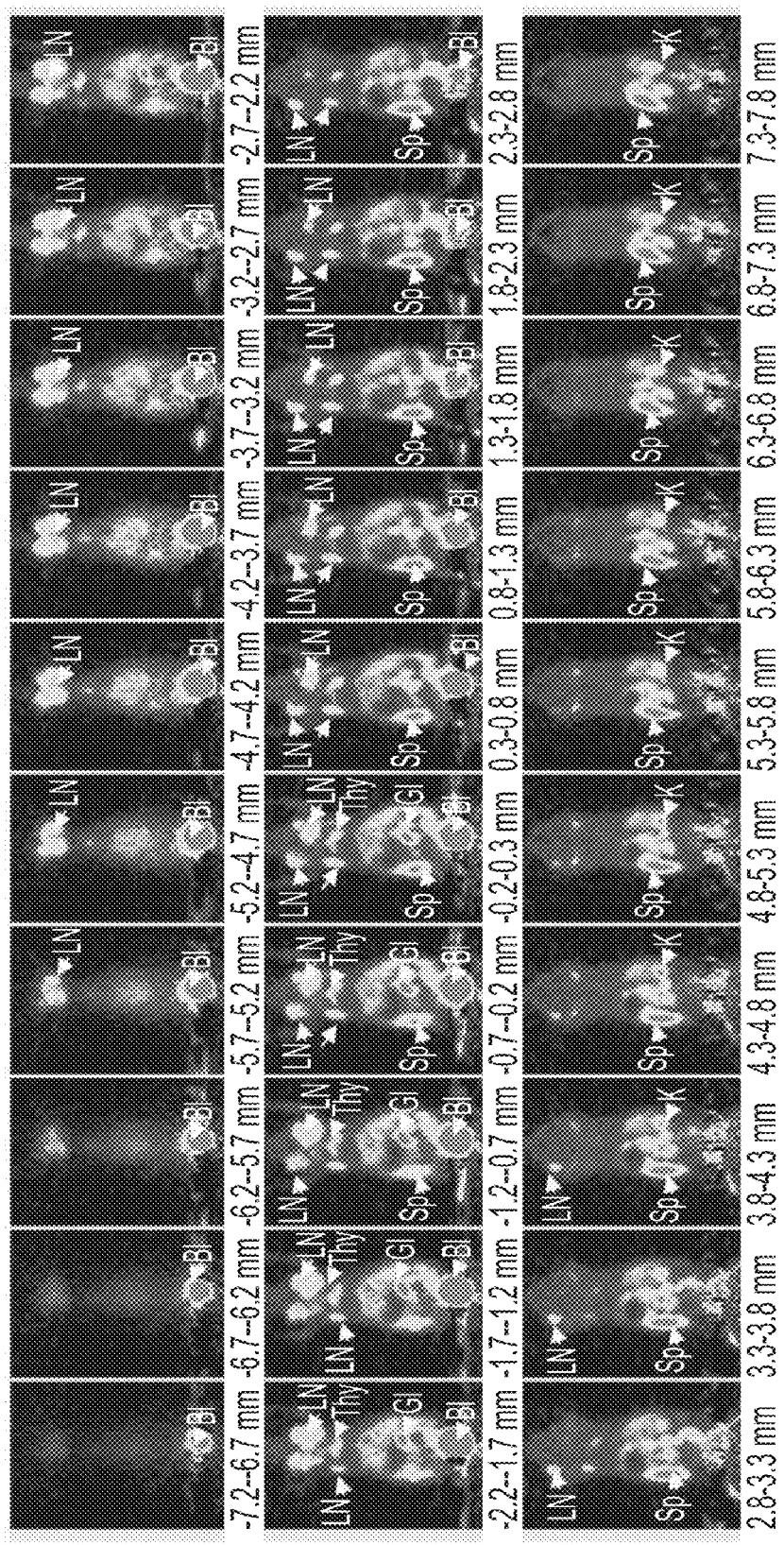
FIG. 26B shows results obtained with the B6.MRL-Fas$^{lpr}$/J autoimmune mouse.

FIG. 26 shows that [$^{18}$F]L-FMAC microPET/CT allows visualization of increased lymphoid mass in systemic autoimmunity. FIG. 26A shows results obtained with the wild type BL/6 mouse. FIG. 26B shows results obtained with the B6.MRL-Fas$^{lpr}$/J autoimmune mouse. Images are 60 minutes after intravenous injection of [$^{18}$F]L-FMAC and show three 1 mm thick coronal slices from mice. The labels are as follow: Thy, Thymus; LN, Lymph Nodes; BM, Bone-Marrow/Bone; Bl, Bladder; GI, Gastrointestinal tract; GB, Gall Bladder; Sp, Spleen; K, Kidney; SC, Spinal Column.

Figure 27:
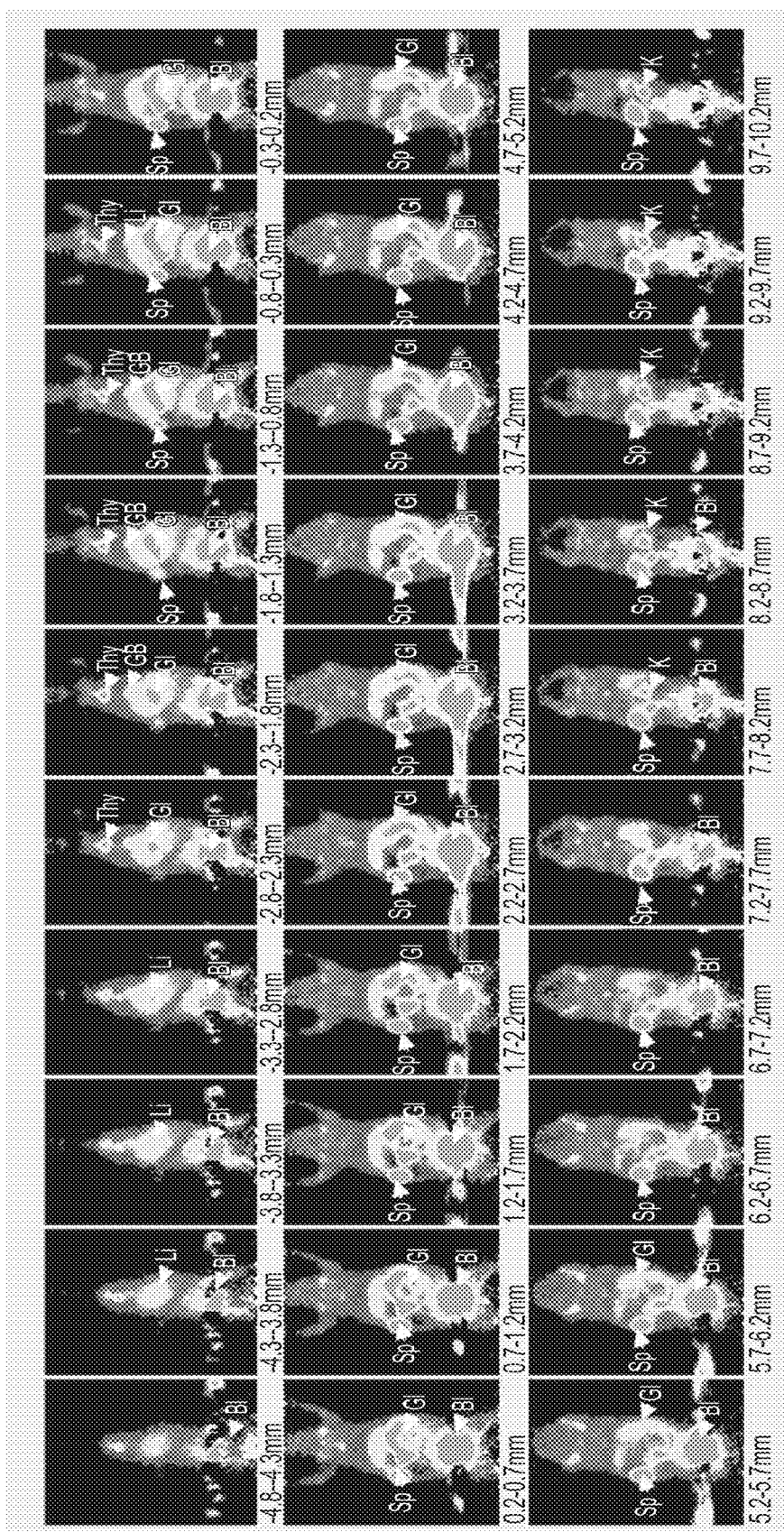
FIG. 27 shows [$^{18}$F]L-FMAC microPET images of immune activation during a primary T cell mediated anti-tumor immune response.
Figure 28:
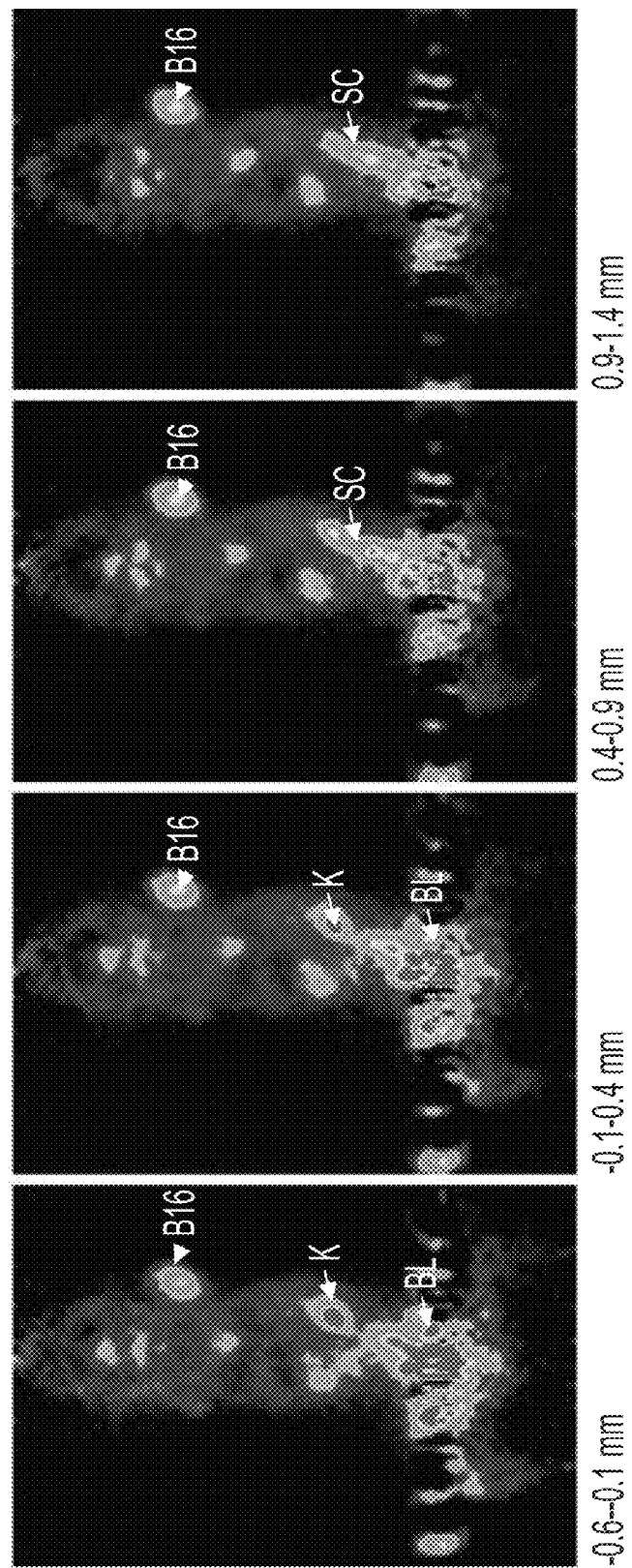
FIG. 28 shows [$^{18}$F]L-FMAC microPET images of melanoma tumors in mice.

FIG. 27 shows PET/CT imaging of localized immune activation in a model of cancer immunotherapy. FIG. 28 shows the results of [$^{18}$F]L-FMAC microPET/CT imaging of B16 melanoma tumors. The images shown are 2 mm coronal sections from [$^{18}$F]L-FMAC microPET/CT scans 1 hour after probe injection. C57BL/6 mice were injected subcutaneously with 1×10$^5$ B16 melanoma cells and imaged 7 days later. The labels are as follow: L, Liver; SP, Spleen; GI, Gastrointestinal tract; BL, Bladder; Tu, Tumor; SC, Spinal Column; K, Kidney.

Figure 29A:
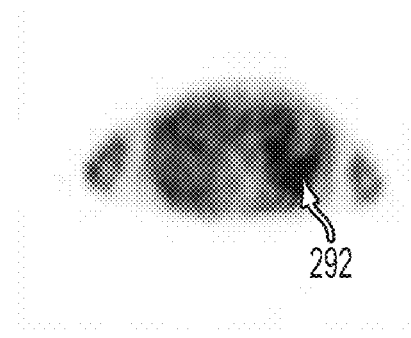
FIGS. 29A and 29B present [$^{18}$F]D-FAC PET images of lymphoma lesions in a human.
Figure 29B:
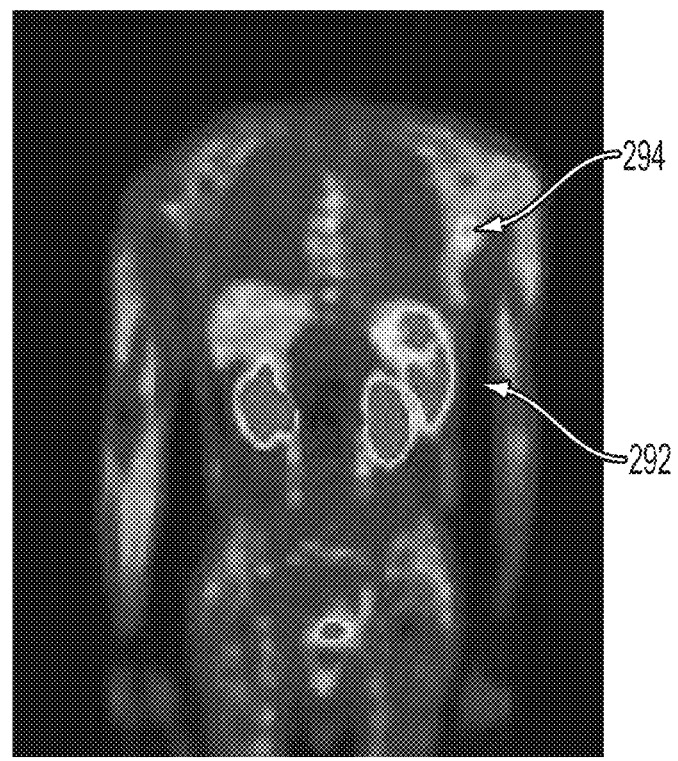

FIG. 29 presents PET scan images of a human subject after injection of [$^{18}$F]D-FAC. The coronal image (FIG. 29B) shows high concentration of [$^{18}$F]D-FAC in a lymph node 294. High concentration of a PET probe, such as [$^{18}$F]D-FAC, in an organ or portion of the lymphatic system can be correlated with abnormal activity in the organ or portion. For example, the high concentration of [$^{18}$F]D-FAC in the lymph node 294 in FIG. 29B can be correlated with a lymphoma lesion. For example, high concentration of a PET probe, such as [$^{18}$F]D-FAC, can be correlated with a malignant lymphoid disease. The heterogeneous spleen 292 is visible.

Figure 30A:
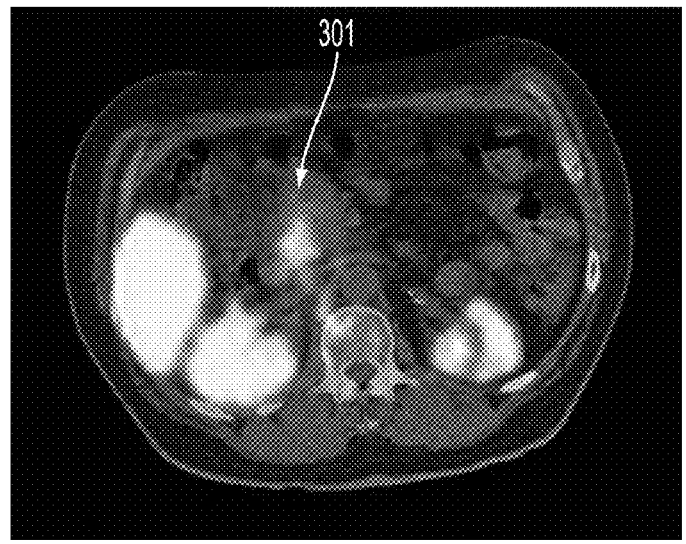
FIG. 30A shows an image obtained with the L-FAC probe.
Figure 30B:
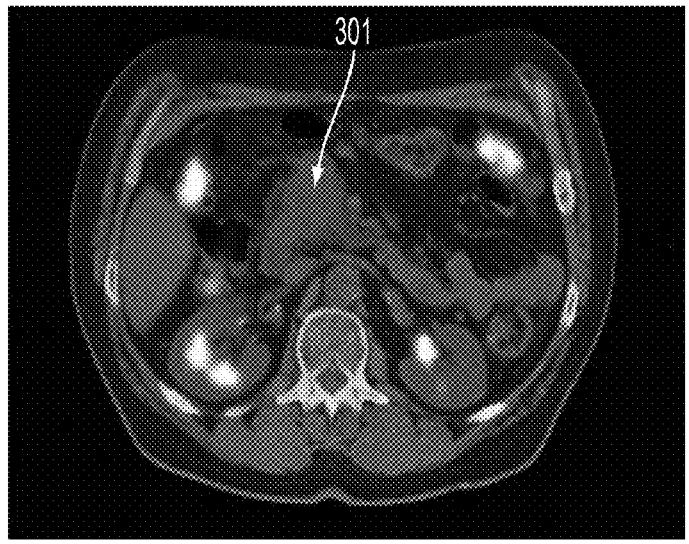
FIG. 30B shows an image obtained with the FDG probe.

FIG. 30 presents PET/CT scans of a 56 year old human male with chronic pancreatitis. The pancreas head 301 is visible. Microscopic examination of a biopsy sample showed a predominantly lymphocytic inflammatory infiltrate with associated degenerative small ducts. The clear accumulation of L-FAC (FIG. 30A) in the pancreatic inflammatory lesions indicates that this novel PET probe could be a better alternative to FDG (FIG. 30B) for diagnosis and management of such disorders in humans.

The PET probe compounds discussed herein that are dCK (deoxycytidine kinase) substrates can be used to predict resistance of cancerous cells to certain oncolytic prodrugs. As discussed above, cells that are resistant exhibit subnormal expression of dCK (see FIGS. 14 and 15). Because of the subnormal dCK expression, these resistant cells exhibit low uptake of the PET probe compounds that are dCK (deoxycytidine kinase) substrates. By contrast, cancerous cells that are not resistant express dCK and, therefore, exhibit higher uptake of the PET probe compounds that are dCK (deoxycytidine kinase) substrates. Thus, administration of the PET probe compounds to a subject or patient in conjunction with PET imaging can identify and locate oncolytic prodrug resistant cancer cells, facilitating the design of an appropriate course of treatment.

The PET probe compound [$^{18}$F]D-FAC discussed herein exhibits low retention in the brain and the myocardium. This is in contrast to the conventional PET probe FDG which substantially accumulates in the brain and the myocardium. Therefore, [$^{18}$F]D-FAC is superior to FDG for the imaging of biological processes and states in and near to the brain and heart. The much lower background of [$^{18}$F]D-FAC in the brain and heart allows for the visualization of biological processes and states of interest. For example, autoimmune and/or inflammatory processes such as may be associated with multiple sclerosis and atherosclerosis can be imaged with the use of [$^{18}$F]D-FAC.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

REFERENCES

1. Hamacher, K., Coenen, H. H., & Stocklin, G. (1986) *J Nucl Med* 27, 235-238.
2. Mangner, T. J., Klecker, R. W., Anderson, L., & Shields, A. F. (2003) *Nuclear Medicine and Biology* 30, 215-224.
3. Qi, J., Leahy, R. M., Cherry, S. R., Chatziioannou, A., & Farquhar, T. H. (1998) *Phys Med Biol* 43, 1001-1013.
4. Chow, P. L., Stout, D. B., Komisopoulou, E., & Chatziioannou, A. F. (2006) *Phys Med Biol* 51, 379-390.
5. Loening, A. M. & Gambhir, S. S. (2003) *Mol Imaging* 2, 131-137.
6. Dubey, P., Su, H., Adonai, N., Du, S., Rosato, A., Braun, J., Gambhir, S. S., & Witte, O. N. (2003) *Proc Natl Acad Sci USA* 100, 1232-1237.
7. Li, C. & Wong, W. H. (2001) *Proc Natl Acad Sci USA* 98, 31-36.
8. Kanehisa, M. & Goto, S. (2000) *Nucleic Acids Research* 28, 27-30.

We claim:
1. A PET probe comprising a compound having a formula comprising:

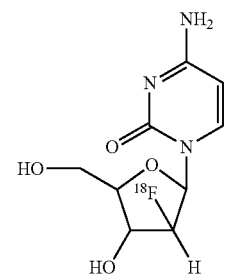

[18F]D-FAC
{D-18F-FAC; 2'-deoxy-2'-[18F]fluoro-β-D-arabinofuranosylcytosine};

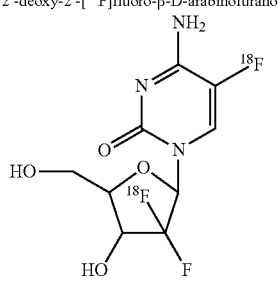

{2',2'-deoxy-2',2'-difluoro-β-D-arabinofuranosyl-5-[18F]fluorocytosine; 5-[18F]fluoro-2',2'-difluorodeoxycytidine};

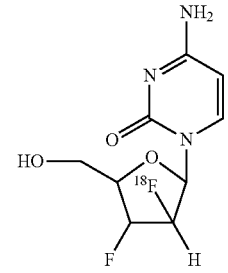

{2',3'-dideoxy-2'-[18F]fluoro-3'-fluoro-b-D-arabinofuranosylcytosine};

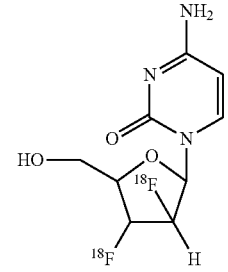

{2',3'-dideoxy-2'-fluoro-3'-[18F]fluoro-b-D-arabinofuranosylcytosine};

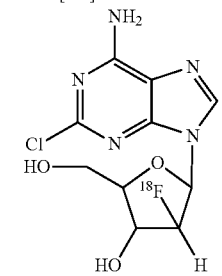

D-2-18F-CA {2-chloro-9-(2-[18F]fluoro-β-D-arabinofuranosyl)adenine};

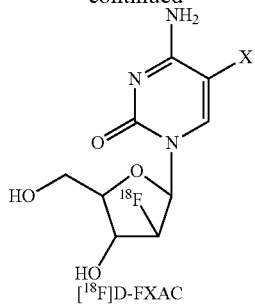

[18F]D-FXAC
{D-18F-FXAC;
2'-deoxy-2'-[18F]fluoro-5-halo-β-D-arabinofuranosylcytosine}
wherein X is halogen;

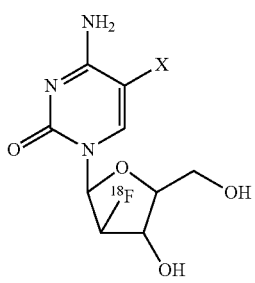

[18F]L-FXAC,
{L-18F-FXAC;
2'-deoxy-2'-[18F]fluoro-5-halo-β-D-arabinofuranosylcytosine};
wherein X is halogen;

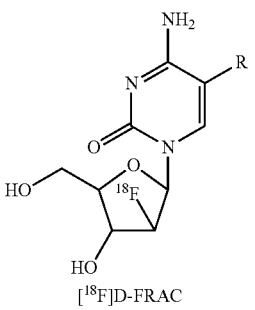

[18F]D-FRAC
{D-18F-FRAC;
2'-deoxy-2'-[18F]fluoro-5-alkyl-β-D-arabinofuranosylcytosine}
wherein R is alkyl having from 1 to 6 carbons;

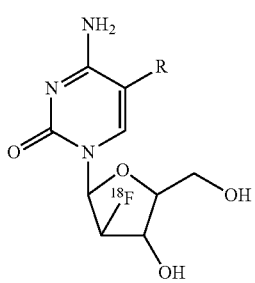

[18F]L-FRAC
{L-18F-FRAC;
2-deoxy-2-[18F]fluoro-5-alkyl-β-L-arabinofuranosylcytosine};
wherein R is alkyl having from 1 to 6 carbons;

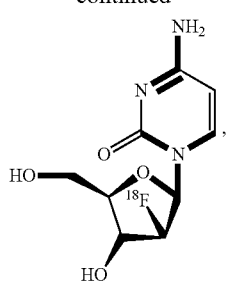

[18F]D-FAC
{D-18F-FAC; 2'-deoxy-2'-[18F]fluoro-β-D-arabinofuranosylcytosine};

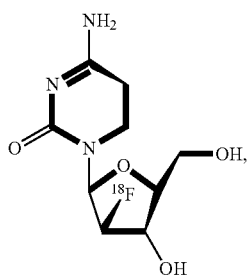

[18F]L-FAC
{L-18F-FAC; 2'-deoxy-2'-[18F]fluoro-β-L-arabinofuranosylcytosine};

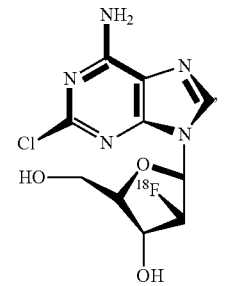

D-2-18F-CA
{2-chloro-9-(2-deoxy-2-[18F]fluoro-β-D-arabinofuranosyl)adenine};

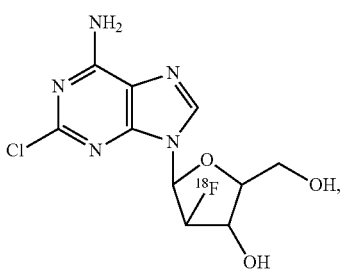

L-2-18F-CA
{2-chloro-9-(2-deoxy-2-[18F]fluoro-β-L-arabinofuranosyl)adenine};

-continued

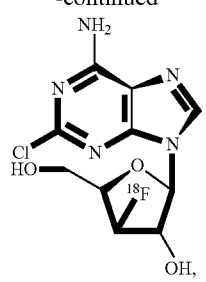

D-3-<sup>18</sup>F-CA
{2-chloro-9-(3-deoxy-3-[<sup>18</sup>F]fluoro-β-D-arabinofuranosyl)adenine};

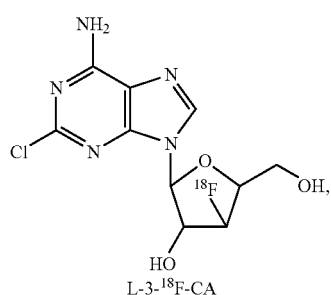

L-3-<sup>18</sup>F-CA
{2-chloro-9-(3-deoxy-3-[<sup>18</sup>F]fluoro-β-L-arabinofuranosyl)adenine};

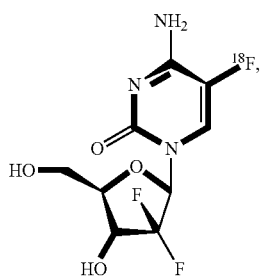

D-Compound #5
{2',2'-deoxy-2',2'-difluoro
β-D-arabinofuranosyl-5-[<sup>18</sup>F]fluorocytosine;
isomer of 5-[<sup>18</sup>F]fluoro-2',2'-difluorodeoxycytidine};

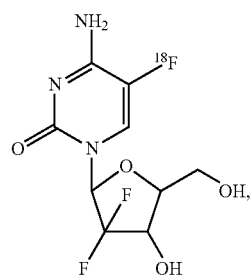

L-Compound #5
{2',2'-deoxy-2',2'-difluoro
β-L-arabinofuranosyl-5-[<sup>18</sup>F]fluorocytosine;
isomer of 5-[<sup>18</sup>F]fluoro-2,2-difluorodeoxycytidine};

-continued

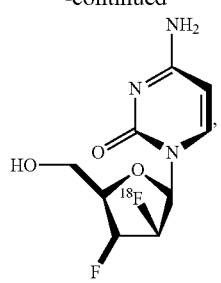

D-Compound #6
{2',3'-dideoxy-2'-[<sup>18</sup>F]fluoro-3'-fluoro-β-D-arabinofuranosylcytosine};

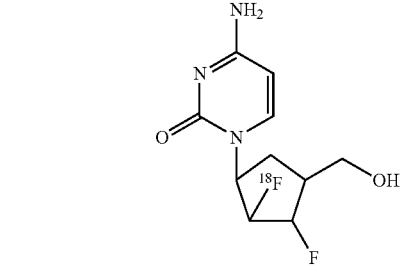

L-Compound #6
{2',3'-dideoxy-2'-[<sup>18</sup>F]fluoro-3'-fluoro-β-L-arabinofuranosylcytosine};

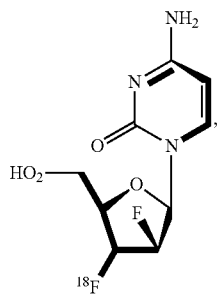

D-Compound #7
{2',3'-dideoxy-2'-fluoro-3'-[<sup>18</sup>F]fluoro-β-D-arabinofuranosylcytosine};

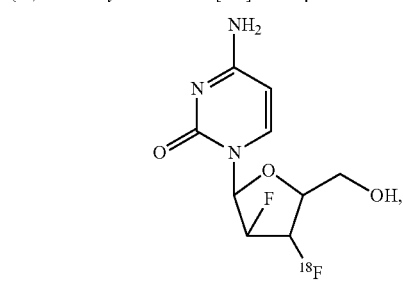

L-Compound #7
{2',3'-dideoxy-2'-fluoro-3'-[<sup>18</sup>F]fluoro-β-L-arabinofuranosylcytosine;

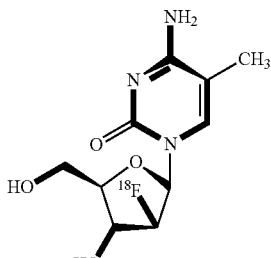

D-<sup>18</sup>F-FMAC
{2'-deoxy-2'-[<sup>18</sup>F]fluoro-5-methyl-β-D-arabinofuranosylcytosine;

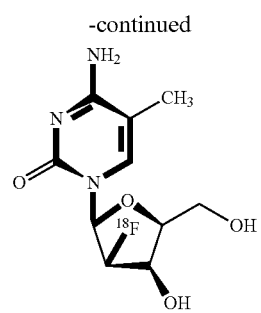

L-¹⁸F-FMAC
{2′-deoxy-2′-[¹⁸F]fluoro-5-methyl-β-L-arabinofuranosylcytosine};

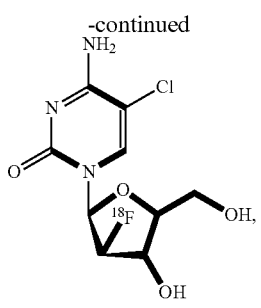

L-¹⁸F-FCAC
{2′-deoxy-2′-[¹⁸F]fluoro-5-chloro-β-L-arabinofuranosylcytosine};

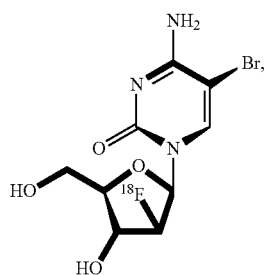

D-¹⁸F-FBAC
{2′-deoxy-2′-[¹⁸F]fluoro-5-bromo-β-D-arabinofuranosylcytosine};

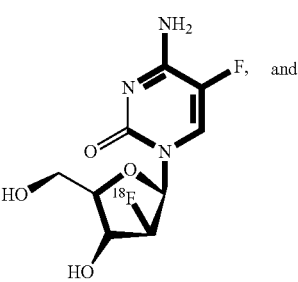

D-¹⁸F-FFAC
{2′-deoxy-2′-[¹⁸F]fluoro-5-fluoro-β-D-arabinofuranosylcytosine};

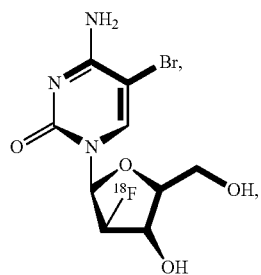

L-¹⁸F-FBAC
{2′-deoxy-2′-[¹⁸F]fluoro-5-bromo-β-L-arabinofuranosylcytosine};

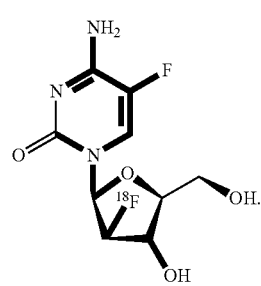

L-¹⁸F-FFAC
{2′-deoxy-2′-[¹⁸F]fluoro-5-fluoro-β-L-arabinofuranosylcytosine};

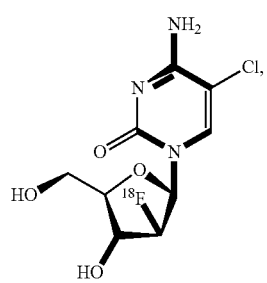

D-¹⁸F-FCAC
{2′-deoxy-2′-[¹⁸F]fluoro-5-chloro-β-D-arabinofuranosylcytosine};

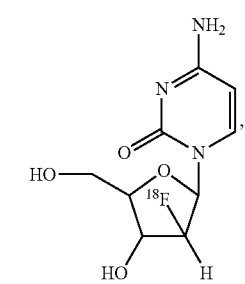

[¹⁸F]D-FAC{D-¹⁸F-FAC; 2′-deoxy-2′-[¹⁸F]fluoro-β-D-arabinofuranosylcytosine};

-continued

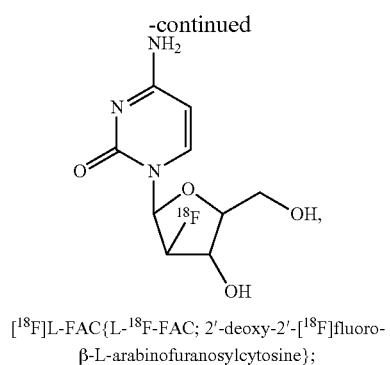

{[$^{18}$F]L-FAC{L-$^{18}$F-FAC; 2'-deoxy-2'-[$^{18}$F]fluoro-
β-L-arabinofuranosylcytosine};

{2-chloro-9-(2-deoxy-2-[$^{18}$F]fluoro-β-D-arabinofuranosyl)adenine; or

{[$^{18}$F]L-FMAC {2'-deoxy-2'-[$^{18}$F]fluoro-5-methyl-
β-L-arabinofuranosylcytosine}.

2. The PET probe of claim 1, the compound having Formula II:

Formula II

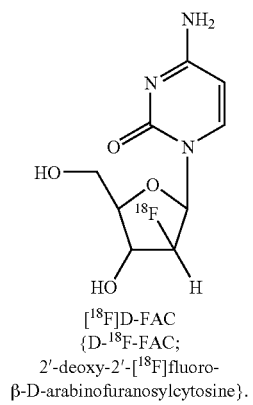

[$^{18}$F]D-FAC
{D-$^{18}$F-FAC;
2'-deoxy-2'-[$^{18}$F]fluoro-
β-D-arabinofuranosylcytosine}.

3. The PET probe of claim 1, the compound having Formula IV, V or V':

Formula IV

{2'-2'-deoxy-2',2'-difluoro-β-D-arabinofuranosyl-5-[$^{18}$F]fluorocytosine; 5-
[$^{18}$F]fluoro-2',2'-difluorodeoxycytidine}

Formula V

{2'-3'-dideoxy-2'-[$^{18}$F]fluoro-3'-fluoro-b-D-arabinofuranosylcytosine}

Formula V'

{2'-3'-dideoxy-2'-fluoro-3'-[$^{18}$F]fluoro-b-D-arabinofuranosylcytosine}.

4. The PET probe of claim 1, the compound having Formula VI:

Formula VI

D-2-$^{18}$F-CA {2-chloro-9-(2-deoxy-2-
[$^{18}$F]fluoro-β-D-arabinofuranosyl)adenine}.

5. The PET probe of claim 1, the compound having the formula

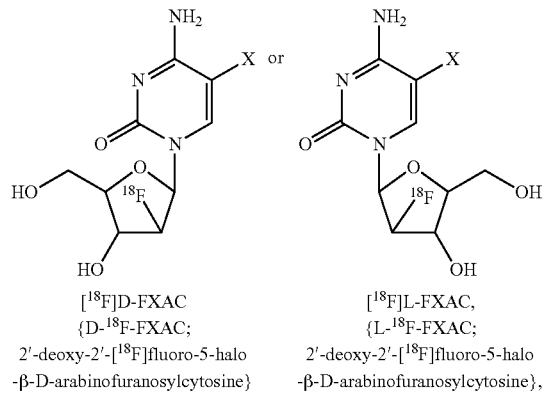

[¹⁸F]D-FXAC
{D-¹⁸F-FXAC;
2′-deoxy-2′-[¹⁸F]fluoro-5-halo
-β-D-arabinofuranosylcytosine}

[¹⁸F]L-FXAC,
{L-¹⁸F-FXAC;
2′-deoxy-2′-[¹⁸F]fluoro-5-halo
-β-D-arabinofuranosylcytosine}, wherein X is halogen.

6. The PET probe of claim 1, the compound having the formula

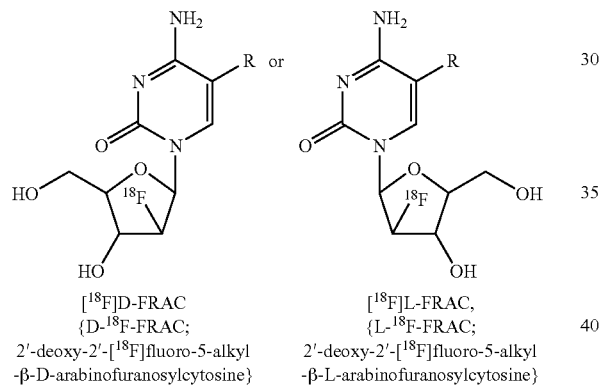

[¹⁸F]D-FRAC
{D-¹⁸F-FRAC;
2′-deoxy-2′-[¹⁸F]fluoro-5-alkyl
-β-D-arabinofuranosylcytosine}

[¹⁸F]L-FRAC,
{L-¹⁸F-FRAC;
2′-deoxy-2′-[¹⁸F]fluoro-5-alkyl
-β-L-arabinofuranosylcytosine} wherein R is alkyl having from 1 to 6 carbons.

7. The PET probe of claim 1, the compound selected from the group consisting of

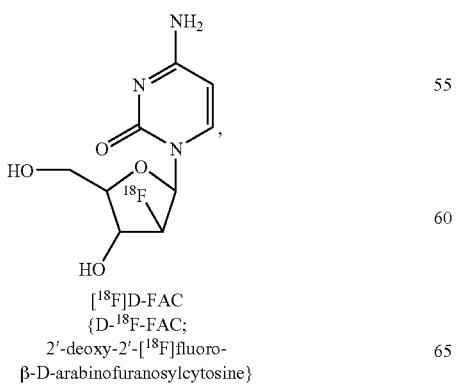

[¹⁸F]D-FAC
{D-¹⁸F-FAC;
2′-deoxy-2′-[¹⁸F]fluoro-
β-D-arabinofuranosylcytosine}

-continued

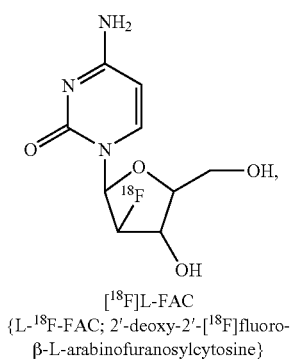

[¹⁸F]L-FAC
{L-¹⁸F-FAC; 2′-deoxy-2′-[¹⁸F]fluoro-
β-L-arabinofuranosylcytosine}

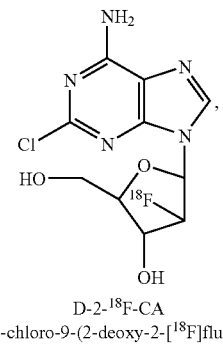

D-2-¹⁸F-CA
{2-chloro-9-(2-deoxy-2-[¹⁸F]fluoro-
β-D-arabinofuranosyl)adenine}

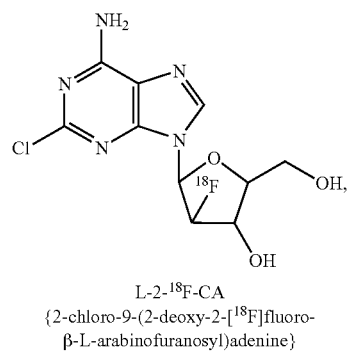

L-2-¹⁸F-CA
{2-chloro-9-(2-deoxy-2-[¹⁸F]fluoro-
β-L-arabinofuranosyl)adenine}

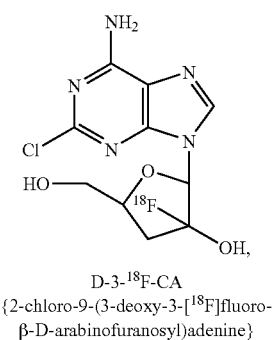

D-3-¹⁸F-CA
{2-chloro-9-(3-deoxy-3-[¹⁸F]fluoro-
β-D-arabinofuranosyl)adenine}

-continued

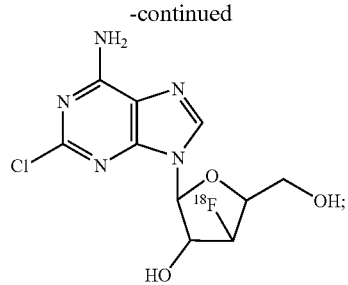

L-3-<sup>18</sup>F-CA
{2-chloro-9-(3-deoxy-3-[<sup>18</sup>F]fluoro-
β-L-arabinofuranosyl)adenine}

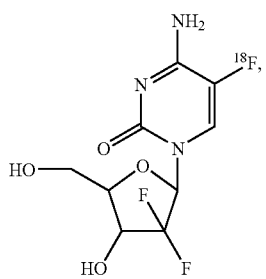

D-Compound #5
{2',2'-deoxy-2',2'-difluoro
β-D-arabinofuranosyl-
5-[<sup>18</sup>F]fluorocytosine;
isomer of 5-[<sup>18</sup>F]fluoro-
2',2'-difluorodeoxycytidine}

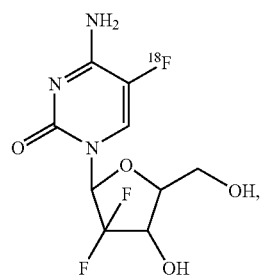

L-Compound #5
{2',2'-deoxy-2',2'-difluoro
β-L-arabinofuranosyl-
5-[<sup>18</sup>F]fluorocytosine;
isomer of 5-[<sup>18</sup>F]fluoro-
2',2'-difluorodeoxycytidine}

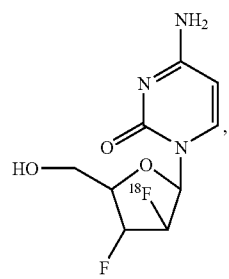

D-Compound #6
{2',3'-dideoxy-2'-[<sup>18</sup>F]fluoro-
3'-fluoro-β-D-arabinofuranosylcytosine}

-continued

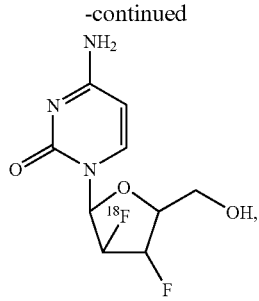

L-Compound #6
{2',3'-dideoxy-2'-[<sup>18</sup>F]fluoro-
3'-fluoro-β-L-arabinofuranosylcytosine}

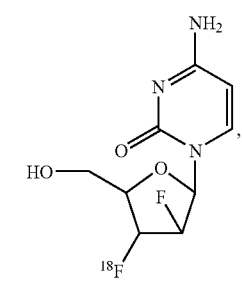

D-Compound #7
{2',3'-dideoxy-2'-fluoro-3'-[<sup>18</sup>F]fluoro-
β-D-arabinofuranosylcytosine}

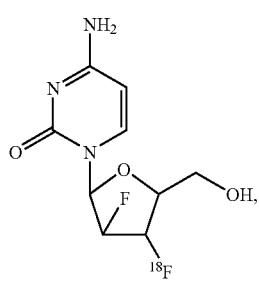

L-Compound #7
{2',3'-dideoxy-2'-fluoro-3'-[<sup>18</sup>F]fluoro-
β-L-arabinofuranosylcytosine}

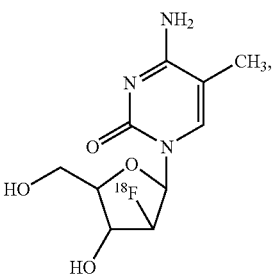

D-<sup>18</sup>F-FMAC
{2'-deoxy-2'-[<sup>18</sup>F]fluoro-5-methyl-
β-D-arabinofuranosylcytosine}

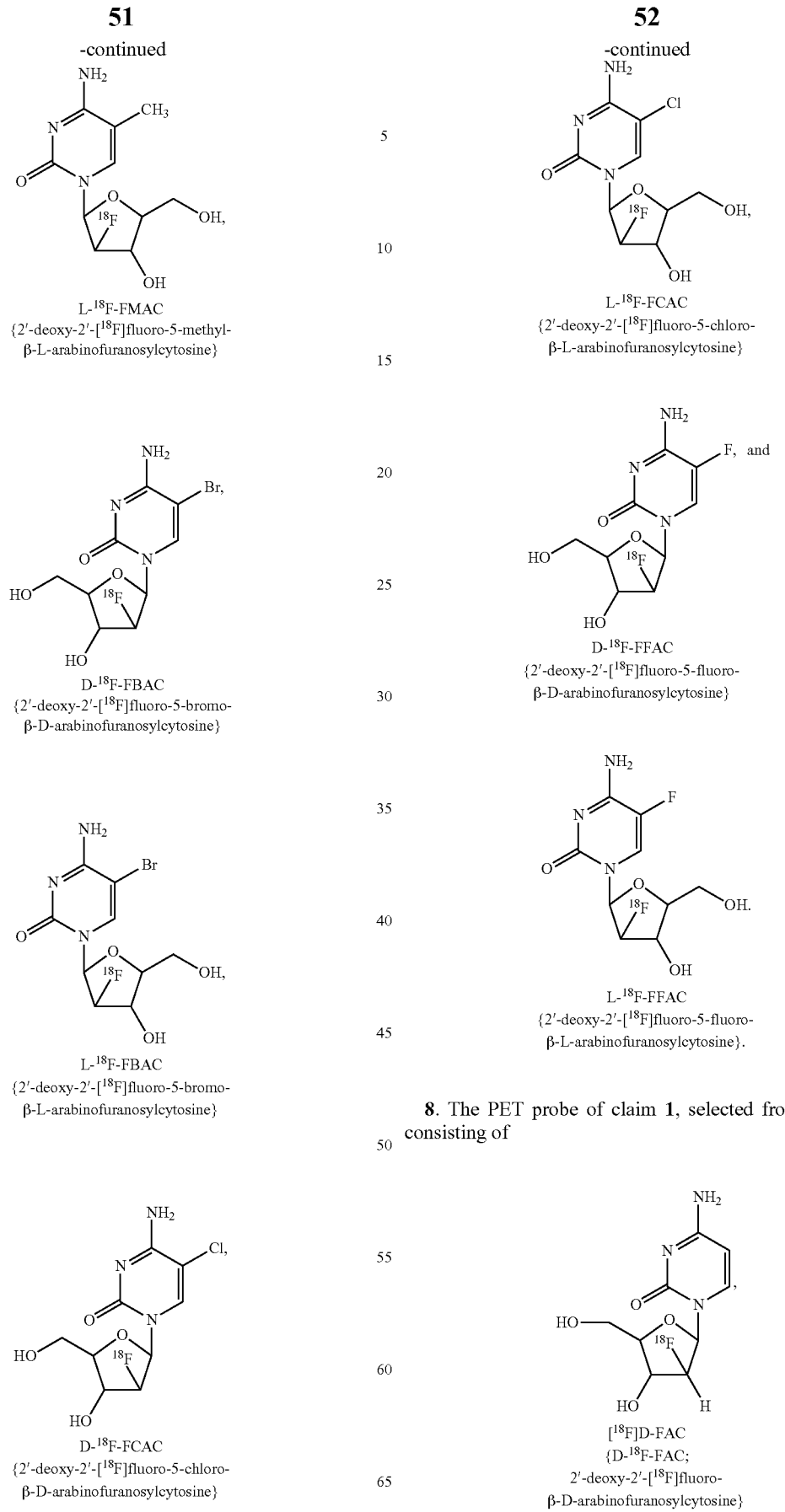
8. The PET probe of claim 1, selected from the group consisting of

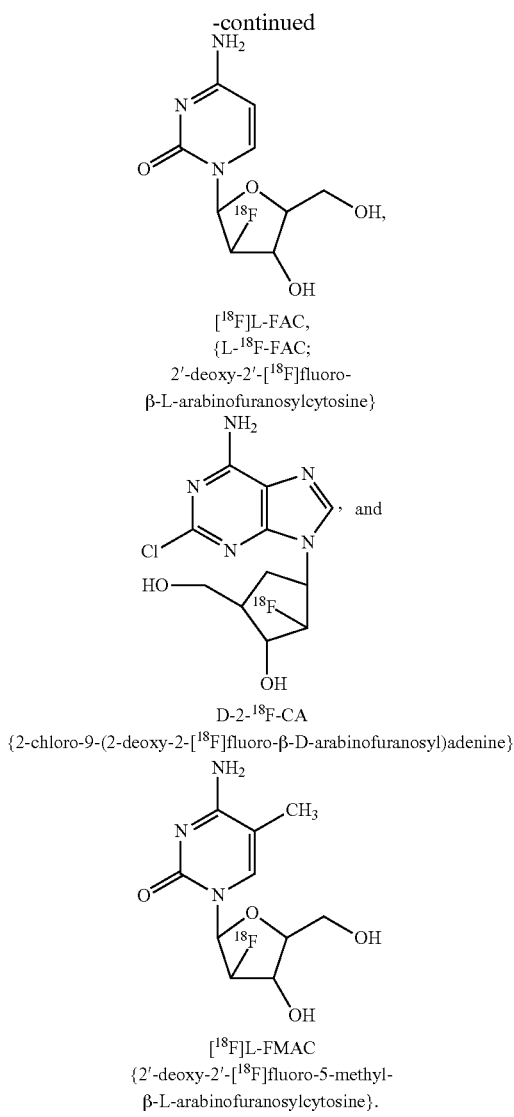

9. The PET probe of claim 1, wherein the compound is a dCK (deoxycytidine kinase) substrate.

10. The PET probe of claim 9, wherein the compound is resistant to deamination.

11. The PET probe of claim 9, wherein the compound is resistant to deamination by an enzyme selected from the group consisting of cytidine deaminase (CDA) and adenosine deaminase.

12. The PET probe of claim 9, wherein the compound is selected from the group consisting of [18F]L-FAC, [18F]L-FXAC, [18F]L-FRAC, D-2-18F-CA, L-2-18F-CA, D-3-18F-CA, and L-3-18F-CA.

13. The PET probe of claim 9, wherein the compound is selected from the group consisting of [18F]L-FAC, [18F]L-FBAC, [18F]L-FCAC, [18F]L-FFAC, [18F]L-FMAC, D-2-18F-CA, L-2-18F-CA, D-3-18F-CA, and L-3-18F-CA.

14. The PET probe of claim 9, wherein the compound is selected from the group consisting of [18F]L-FAC and [18F]F-CA.

15. The PET probe of claim 1, wherein the compound when administered to a subject does not accumulate to a high concentration in the brain or myocardium.

16. A method of predicting resistance to an oncolytic prodrug, comprising:
contacting the PET probe of claim 1 with a neoplasm;
using PET imaging to determine a local concentration of the PET probe compound in the neoplasm;
comparing the local concentration of the PET probe compound with a baseline level;
correlating a local concentration of the PET probe compound with the baseline level and with low dCK expression of the neoplasm;
correlating low dCK expression of the neoplasm with oncolytic nucleoside analog resistance, wherein the baseline level corresponds to a measured concentration of the PET probe compound in representative neoplastic cells that express dCK, concentration of the PET probe compound in representative neoplastic cells that do not express dCK, or a weighted average.

17. The method of claim 16, wherein the compound of the PET probe is selected from the group consisting of [18F]D-FAC, [18F]L-FAC, [18F]D-FXAC, [18F]L-FXAC, [18F]D-FRAC, [18F]L-FRAC, D-2-18F-CA, L-2-18F-CA, D-3-18F-CA, and L-3-18F-CA.

18. The method of claim 16, wherein the compound of the PET probe is selected from the group consisting of [18F]D-FAC, [18F]L-FAC, [18F]D-FFAC, [18F]L-FFAC, [18F]D-FCAC, [18F]L-FCAC, [18F]D-FBAC, [18F]L-FBAC, [18F]D-FMAC, [18F]L-FMAC, D-2-18F-CA, L-2-18F-CA, D-3-18F-CA, and L-3-18F-CA.

19. The method of claim 16, wherein compound of the PET probe is selected from the group consisting of [18F]D-FAC, [18F]L-FAC, D-2-18F-CA, D-3-18F-CA, and [18F]L-FMAC.

20. The method of claim 16, wherein the representative neoplastic cells are selected from the group consisting of leukemia, acute non-lymphocytic leukemia, acute lymphocytic leukemia, blast phase of chronic myelocytic leukemia, meningeal leukemia, pancreatic cancer, ovarian cancer, breast cancer, non-small cell lung cancer, B-cell chronic lymphocytic leukemia, hairy cell leukemia, relapsed acute lymphoblastic leukemia, and refractory acute lymphoblastic leukemia cells.

21. The method of claim 16, wherein the oncolytic prodrug is selected from the group consisting of cytosine arabinoside (Ara-C), fludarabine, cladribine, and clofarabine.

22. The method of claim 16, wherein the oncolytic prodrug is gemcitabine.

23. A method, comprising using the PET probe of claim 1 in the diagnosis and treatment of a condition by administering the PET probe to a subject and then visualizing the PET probe in the subject, wherein the condition is selected from the group consisting of rheumatoid arthritis, inflammatory bowel disease, type 1 diabetes, EAE (Experimental Autoimmune Encephalomyelitis), multiple sclerosis, atherosclerosis, an autoimmune disorder, and cancer.

24. A method, comprising using the PET probe of claim 1 by exposing the PET probe to cells and then visualizing the PET probe in the cells in order to evaluate the efficacy in the treatment of cancer of an anticancer agent that is taken up into cells via nucleoside transporters and deoxycytidine kinase (dCK)-mediated phosphorylation.

25. The method of claim 24, wherein the anticancer agent is selected from the group consisting of cytarabine and 2'-difluorodeoxycytidine.

26. A method of imaging, comprising:
contacting a PET probe that is a cytosine or adenosine analog and a dCK substrate with a biological material;
using PET imaging to determine a local concentration of the PET probe compound in the biological material; and correlating the local concentration of the PET probe compound with a local immune response or the presence of neoplastic tissue.

27. The method of claim 26,
wherein contacting the PET probe with a biological material comprises administering a quantity of the PET probe to an animal or human; and
correlating the local concentration of the PET probe in the animal or human with a local immune response or neoplastic tissue in the animal or human.

28. The method of claim 27, further comprising using the local concentration of the PET probe to diagnose cancer and/or monitor cancer treatment.

29. The method of claim 27, wherein the animal or human has a condition selected from the group consisting of cancer, an autoimmune disorder, a development disorder, viral infection, bacterial infection, parasitical infection, infection, a metabolic disease, and inflammation.

30. The method of claim 27, wherein the animal or human has a condition selected from the group consisting of lymphadenopathy, melanoma, leukemia, and glioma.

31. The method of claim 27, wherein the animal or human has a condition selected from the group consisting of rheumatoid arthritis, inflammatory bowel disease, Experimental Autoimmune Encephalomyelitis (EAE), multiple sclerosis, type 1diabetes, and atherosclerosis.

32. The method of claim 27, wherein the animal or human is undergoing a therapy selected from the group consisting of cancer immunotherapy, immunotherapy, interferon therapy, vaccination, radiation therapy, chemotherapy, and antibiotic therapy.

33. The method of claim 26,
wherein contacting the PET probe with a biological material comprises administering a quantity of the PET probe to an animal or human; and
correlating the local concentration of the PET probe in the animal or human with abnormal activity in an organ or portion of the lymphatic system, for example, a lymph node or the spleen.

34. The method of claim 33, further comprising correlating the local concentration of the PET probe with a lymphoma lesion or a malignant lymphoid disease.

35. The method of claim 26, wherein the local immune response is the accumulation of activated T lymphocytes.

36. The method of claim 35, wherein the activated T lymphocytes take up more PET probe per cell than non-activated T lymphocytes.

37. A method of imaging, comprising administering the PET probe of claim 1 to a subject and using PET imaging to provide an image of the local concentration of the probe compound.

38. A method of synthesizing a PET probe compound, comprising:
reacting 2-O-[(trifluoromethyl)sulfonyl]-1,3,5-tri-O-benzoyl-α-Q-ribofuranose with [$^{18}$F]fluoride ion to form 2-deoxy-2-[$^{18}$F]fluoro-1,3,5-tri-O-benzoyl-α-Q-arabinofuranose as a first radiolabeled intermediate;
reacting the first radiolabeled intermediate with hydrogen bromide to form 2-deoxy-2-[$^{18}$F]fluoro-3,5-di-O-benzoyl-α-Q-arabinofuranosyl bromide as a second radiolabeled intermediate;
reacting the second radiolabeled intermediate with 5-Z-4-N-(trimethylsilyl)-2-O-(trimethylsilyl) pyrimidine-4-amine or 2-chloroadenine to form 5-Z-1-(2-deoxy-2-[$^{18}$F]fluoro-3,5-di -O-benzoyl-β-Q-arabinofuranosyl)cytosine or 2-chloro-9-(4-benzoyloxymethyl-3-benzoyloxy-2-deoxy-2-[18F]fluoro-β-Q-arabinofuranosyl)adenine as a third radiolabeled intermediate;
reacting the third radiolabeled intermediate with an alkoxide to form the PET probe compound 5-Z-1-(2-deoxy-2-[$^{18}$F]-β-Q-arabinofuranosyl)cytosine or 2-chloro-9-(2-deoxy-2-[$^{18}$F]fluoro-β-Q-arabinofuranosyl)adenine,
wherein Z is hydrogen, halogen, or lower alkyl,
wherein lower alkyl is an alkyl having from 1 to 6 carbons, and
wherein Q is D or L of the D,L-system for naming enantiomers.

39. The method of claim 38, wherein the alkoxide is selected from the group consisting of an alkali methoxide and sodium methoxide.

40. The method of claim 38, wherein Z is selected from the group consisting of hydrogen, fluorine, chlorine, bromine, and methyl.

41. A method of synthesizing an [$^{18}$F]-CA PET probe compound, comprising:
reacting Q-2-chloroadenosine and monomethoxytrityl chloride to form a first intermediate;
reacting the first intermediate with trifyl chloride to form a second intermediate;
reacting the second intermediate with [$^{18}$F]fluoride ion to form 2-chloro-9-(2-deoxy-2-[$^{18}$F]fluoro-β-Q-arabinofuranosyl)adenine and 2-chloro-9-(3-deoxy-3-[$^{18}$F]fluoro-β-Q-arabinofuranosyl) adenine as the [$^{18}$F]-CA PET probe compound,
wherein Q is D or L of the D,L-system for naming enantiomers.

* * * * *